(12) United States Patent
O'Neil et al.

(10) Patent No.: US 9,115,072 B2
(45) Date of Patent: *Aug. 25, 2015

(54) COMPOUNDS AND METHOD FOR REDUCING URIC ACID

(71) Applicant: WELLSTAT THERAPEUTICS CORPORATION, Gaithersburg, MD (US)

(72) Inventors: James Dennen O'Neil, Frederick, MD (US); Michael K Bamat, Potomac, MD (US); Reid W von Borstel, Potomac, MD (US); Shalini Sharma, Gaithersburg, MD (US); Ramachandran Arudchandran, Germantown, MD (US)

(73) Assignee: Wellstat Therapeutics Corporation, Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 13/890,789

(22) Filed: May 9, 2013

(65) Prior Publication Data

US 2013/0259850 A1 Oct. 3, 2013

Related U.S. Application Data

(63) Continuation of application No. 12/920,555, filed as application No. PCT/US2009/037128 on Mar. 13, 2009, now Pat. No. 8,829,058.

(60) Provisional application No. 61/036,294, filed on Mar. 13, 2008.

(51) Int. Cl.
  *A01N 31/14* (2006.01)
  *A61K 31/075* (2006.01)
  *A01N 35/00* (2006.01)
  (Continued)

(52) U.S. Cl.
  CPC .............. *C07C 59/68* (2013.01); *A61K 31/192* (2013.01); *A61K 31/216* (2013.01); *A61K 45/06* (2013.01); *C07C 59/66* (2013.01); *C07C 59/84* (2013.01); *C07C 59/88* (2013.01); *C07C 59/90* (2013.01); *C07C 61/39* (2013.01); *C07C 69/716* (2013.01);
  (Continued)

(58) Field of Classification Search
  None
  See application file for complete search history.

(56) References Cited

U.S. PATENT DOCUMENTS 6,677,473 B1  1/2004  Madison et al.
6,858,602 B2  2/2005  Sharma et al.
(Continued)

FOREIGN PATENT DOCUMENTS

EP  180515 A1  8/2007
WO  02100341 A2  12/2002
(Continued)

OTHER PUBLICATIONS

Gustafsson et al., BMC Nephrology, 2013, vol. 14, pp. 164-172.*
(Continued)

*Primary Examiner* — Jeffrey S Lundgren
*Assistant Examiner* — Stephanie Springer
(74) *Attorney, Agent, or Firm* — Lewis J. Kreisler

(57) ABSTRACT

Uric acid in mammalian subjects is reduced and excretion of uric acid is increased by administering a compound of Formula I or a pharmaceutically acceptable salt thereof.

(I)

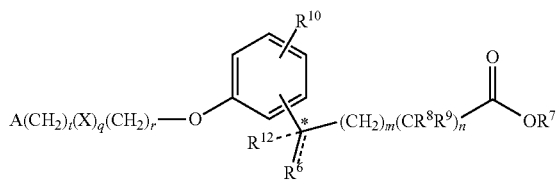

In Formula I m is 0, 1, 2, 3 or 4; n is 0 or 1; m+n is not more than 4;
t is 0 or 1; q is 0 or 1; and r is 0, 1 or 2. $R^6$ is hydrogen, methyl or ethyl and $R^{12}$ is hydrogen or methyl, or $R^6$ is hydroxy and $R^{12}$ is hydrogen, or $R^6$ is O and $R^{12}$ is absent, or $R^6$ and $R^{12}$ together are —$CH_2CH_2$—. $R^7$ is hydrogen or alkyl having from 1 to 3 carbon atoms. One of $R^8$ and $R^9$ is alkyl having from 1 to 3 carbon atoms, and the other is hydrogen or alkyl having from 1 to 3 carbon atoms. $R^{10}$ is hydrogen, halo, alkyl having from 1 to 3 carbon atoms or alkoxy having from 1 to 3 carbon atoms. X is C(O) and r is 0 and t is 0; or X is NH($R^{11}$) wherein $R^{11}$ is hydrogen or alkyl having from 1 to 3 carbon atoms. A is phenyl, unsubstituted or substituted by 1 or 2 groups selected from halo, hydroxy, methyl, ethyl, perfluoromethyl, methoxy, ethoxy, and perfluoromethoxy; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl. The uric acid-lowering effects of the Compounds of Formula I are used to treat or prevent a variety of conditions including gout, hyperuricemia, elevated levels of uric acid that do not meet the levels customarily justifying a diagnosis of hyperuricemia, renal dysfunction, kidney stones, cardiovascular disease, risk for developing cardiovascular disease, tumor-lysis syndrome, and cognitive impairment.

14 Claims, 6 Drawing Sheets

(51) Int. Cl.

| | |
|---|---|
| *A61K 31/12* | (2006.01) |
| *A01N 31/08* | (2006.01) |
| *A61K 31/05* | (2006.01) |
| *A01N 37/10* | (2006.01) |
| *A61K 31/195* | (2006.01) |
| *C07C 59/68* | (2006.01) |
| *A61K 31/192* | (2006.01) |
| *C07C 59/66* | (2006.01) |
| *C07C 59/84* | (2006.01) |
| *C07C 59/88* | (2006.01) |
| *C07C 61/39* | (2006.01) |
| *C07C 69/716* | (2006.01) |
| *A61K 31/216* | (2006.01) |
| *A61K 45/06* | (2006.01) |
| *C07C 59/90* | (2006.01) |
| *C07C 69/734* | (2006.01) |
| *C07C 69/738* | (2006.01) |

(52) U.S. Cl.
CPC ............. *C07C 69/734* (2013.01); *C07C 69/738* (2013.01); *C07C 2101/02* (2013.01)

(56) References Cited

U.S. PATENT DOCUMENTS

| | | | |
|---|---|---|---|
| 6,916,848 | B2 | 7/2005 | Sharma |
| 6,924,314 | B2 | 8/2005 | Sharma et al. |
| 6,946,491 | B2 | 9/2005 | Sharma et al. |
| 7,012,071 | B2 | 3/2006 | Sharma et al. |
| 7,041,659 | B2 | 5/2006 | Sharma |
| 7,045,541 | B2 | 5/2006 | Sharma |
| 7,101,910 | B2 | 9/2006 | Sharma et al. |
| 7,323,480 | B2 | 1/2008 | Zhu et al. |
| 7,329,782 | B2 | 2/2008 | Sharma |
| 7,494,537 | B2 | 2/2009 | Ono et al. |
| 7,514,555 | B2 | 4/2009 | Hodge et al. |
| 7,547,802 | B2 | 6/2009 | Sharma |
| 7,605,181 | B2 | 10/2009 | Hodge et al. |
| 7,615,575 | B2 | 11/2009 | Hodge et al. |
| 7,622,491 | B2 | 11/2009 | Zhu et al. |
| 7,645,772 | B2 | 1/2010 | Hodge et al. |
| 7,851,494 | B2 | 12/2010 | Sharma et al. |
| 7,863,475 | B2 | 1/2011 | Sharma |
| 7,932,290 | B2 | 4/2011 | Hodge et al. |
| 8,410,154 | B2 | 4/2013 | O'Neil et al. |
| 8,829,058 | B2 | 9/2014 | O'Neil |
| 2003/0220399 | A1 | 11/2003 | Luskey et al. |
| 2005/0090555 | A1 | 4/2005 | Sharma et al. |
| 2005/0256333 | A1 | 11/2005 | Sharma et al. |
| 2007/0010670 | A1 | 1/2007 | Hirate et al. |
| 2007/0099846 | A1 | 5/2007 | Chang |
| 2007/0105958 | A1 | 5/2007 | Sharma et al. |
| 2007/0197512 | A1 | 8/2007 | Inoue et al. |
| 2007/0197650 | A1 | 8/2007 | Coop et al. |
| 2007/0244172 | A1 | 10/2007 | Sharma et al. |
| 2008/0015254 | A1 | 1/2008 | Hodge et al. |
| 2013/0331452 | A1 | 12/2013 | Sharma et al. |

FOREIGN PATENT DOCUMENTS

| | | | |
|---|---|---|---|
| WO | 2004041165 | A2 | 5/2004 |
| WO | 2004073611 | A2 | 9/2004 |
| WO | 2004091486 | A2 | 10/2004 |
| WO | 2004098496 | A2 | 11/2004 |
| WO | 2007056771 | A2 | 5/2007 |
| WO | 2007087506 | A2 | 8/2007 |
| WO | 2007146768 | A2 | 12/2007 |
| WO | 2009091732 | A1 | 7/2009 |

OTHER PUBLICATIONS

Yamamoto, Y., et al "Allopurinol Reduces Neointimal Hyperplasia in the Carotid Artery Ligation Model in Spontaneously Hypertensive Rats," Hypetens. Res, 29(11): 915-921, (2006).

Zoccali, C., et al., "Uric Acid and Endothelial Dysfunction in Essential Hypertension," J Am Soc Nephrol., 17(5): 1466-71, (2006).

Фармакология: учебник для ВУЗов, под ред. Р.Н. Аляутдина, 2-е

издание, исправленное, М. ГЭОТАР-МЕД, 2004 (in Russian only); Farmakologija: uchebnik dlja VUZov, pod red. R.N. Aljautdin, 2-e izdanie, ispravlennoe, M. GJeOTAR-MED, 2004.

Office action dated Sep. 27, 2013 in U.S. Appl. No. 13/783,680.

PubChem Public Chemical Database, CID 10517300, created Oct. 25, 2006, (online), NCBI, <URL: http://pubchem.ncbi.nlm.nih.gov/summary/summary.cgi?cid=10517300> [Retrieved Jun. 4, 2012].

Pending claims in U.S. Appl. No. 14/004,928 (as of Sep. 13, 2013).

Anzai et al., "The Multivalent PDZ Domain-containing Protein PDZK1 Regulates Transport Activity of Renal Urate Anion Exchanger URAT1 via Its C Terminus", J. Biol. Chem., 279(44): 45942-45950 (2004).

Armstrong, K.A. et al., "Does Uric Acid Have a Pathogenetic Role in Graft Dysfunction and Hypertension in Renal Transplant Patients?," Transplantation, 80(11):1565-1571 (2005).

Arnoldi, et al., "Synthesis of 3-Aryl-1,4-benzoxathianes: Application to the preparation of a sweet compound", Journal of the Chemical Society, Perkin Transactions, 1:1241-1244 (1994).

Avaram, V., and E. Krishnan, "Hyperuricemia—Where Nephrology Meets Rheumatology," Rheumatology (Oxford), 47(7): 960-964, (2008).

Bainbridge. S.A. and Roberts, J.M., "Uric Acid as a Pathogenic Factor in Preeclampsia," Placenta 29, Supplement A, Trophoblast Research, vol. 22: S67-S72, (2008).

Benigni et al., "Synthesis of two new metabolites of catecholamines: 3,4-dihydroxyphenylethylene glycol and 4-hydroxy-3-methoxyphenylethyleneglycol", Journal of Medicinal Chemistry, 6(5):.607-608 (1963).

Bieber, et al., "Gout: On the Brink of Novel Therapeutic Options for an Ancient Disease", Arthritis & Rheumatism, 50(8): 2400-2414 (Aug. 2004).

Bos et al., "Uric Acid is a Risk Factor for Myocardial Infarction and Stroke: the Rotterdam Study," Stroke. 37(6): 1503-7 (Jun. 2006).

Brown, et al., "Use of ethoxy-homologs as internal standards for determination of urinary vanillylmandelic acid and normetanephrine in man by high performance liquid chromatography", Journal of Liquid Chromatography, 9(4): 831-843 (1986).

Cengel A., et al., "Serum uric Acid Levels as a Predictor of In-hospital Death in Patients Hospitalized for Decompensated Heart Failure," Acta Cardiol, 60(5): 489-492, (Oct. 2005).

Chien, K-L, et al., "Plasma Uric Acid and the Risk of Type 2 Diabetes in a Chinese Community," Clin. Chem. 54(2): 310-316, (2008).

Ciofi-Baffoni, et al, "Synthesis of oligomeric mimics of lignin", Journal of the Chemical Society, Perkin Transactions, Organic and Bio-Organic Chemistry, 1: 3207-3218 (1998).

Cirillo et al., "Uric Acid. The Metabolic Syndrome, and Renal Disease," J Am Soc Nephrol. 17:S165-8, (2006).

Coutinho et al "Associations of Serum Uric Acid with Markers of Inflammation, Metabolic Syndrome. and Subclinical Coronary Atherosclerosis," Amer. J. Hypertens, 20: 83-89 (2007).

Feig, D.I., and Johnson, R.J., "The Role of Uric Acid in Pediatric Hypertension," J Ren Nutrition 17(1): 79-83. (2007).

Feig, D.I., et al., "Effect of Allopurinol on Blood Pressure of Adolescents With Newly Diagnosed Essential Hypertension" JAMA 300(8): 924-932.(2008).

Halevy et al., "Allopurinol is the Most Common Cause of Stevens-Johnson Syndrome and Toxic Epidermal Necrolysis in Europe and Israel," J Am Acad Dermatol. 58(1):25-32, (2008).

Inokuchi, T., et al., "Plasma IL-18 and Other Inflammatory Cytokines in Patients With Gouty Arthritis and Monosodium Urate Monohydrate Crystal-Induced Secretion of IL-18," Cytokine. 33(1): 21-27, (2006).

Ioachimescu, A.G. et al. "Serum Uric Acid, Mortality and Glucose Control in Patients With Type 2 Diabetes Mellitus: a Precis Database Study," Diabet. Med. 24 (12) 1369-1374 (2007).

(56) References Cited

OTHER PUBLICATIONS

Ishizaka, N., et al., "Association Between Serum Uric Acid, Metabolic Syndrome, and Carotid Atherosclerosis in Japanese Individuals," Arterioscler Thromb Vase Biol., 25: 1038-44 (2005).

Jee, S.A., et al. "Serum Uric Acid and Risk of Death From Cancer. Cardiovascular Disease or All Causes in Men," Eur. J. Cardiovascular Prey. Rehab., 11(3):185-191 (2004).

Kanellis, J., and Kang, D-H., "Uric Acid as a Mediator of Endothelial Dysfunction, Inflammation, and Vascular Disease," Semin Nephrol., 25(1); 39-42 (2005).

Kang, D-H., et al., "Uric Acid Causes Vascular Smooth Muscle Cell Proliferation by Entering Cells Via a Functional Urate Transporter," Am J Nephrol. 2005 25(5):425-33 (2005).

Kappe, et al., Synthes of potentieller metaboliten of 2-amino-N-(β-hydroxy-2,5-dimethoxyphenethyl)-acetamids (Midodrin), Archiv der Pharmazie (Weinheim, Germany), 308(5):339-346, (1975)(German language).

Kappe, et al., Accession No. 83:178502, Synthesis of potential metabolites of 2-amino-N-(β-hydroxy-2,5-dimethoxyphenethyl)acetamide (Midodrine), Archiv der Pharmazie (Weinheim, Germany), 308(5):339-346 (1975).

Khosla, UM, et al., "Hyperuricemia Induces Endothelial Dysfunction," Kidney Int. 67(5):1739-42, (2005).

Krishnan, E., et al. "Gout in Ambulatory Care Settings in the United States," Journal of Rheumatology, 35(3): 498-501 (2008).

Lehto, S., et al., "Serum Uric Acid is a Strong Predictor of Stroke in Patients With Non-Insulin Dependent Diabetes Mellitus," Stroke 29: 635-639(1998).

Leyva, F., et al., "Uric Acid in Chronic Heart Failure: A Marker of Chronic Inflammation", Eur. Heart J., 19(12): 1814-1822, (1998).

Mikuls, T.R., et al. "Gout Epidemiology; Results from the UK General Practice Research Database, 1990-1999." Annals of the Rheumatic Diseases, 64:267-272, (2005).

Pascual-Figal, D.A., et al., "Hyperuricaemia and Long-Term Outcome After Hospital Discharge in Acute Heart Failure Patients," Eur J Heart Fail., 9:518-524, (2007).

Perlstein, T.S., et al., "Uric Acid and the State of the Intrarenal Renin-Angiotensin System in Humans," Kidney International. 66: 1465-1470, (2004).

Perry. I.J. et al., "Prospective Study of Risk Factors for Development of Non-Insulin Dependent Diabetes in Middle Aged British Men," BMJ, 310 (6979) 560-564, (1995).

Price, K.L., et al., "Human Vascular Smooth Muscle Cells Express a Urate Transporter," J Am Soc Nephrol. 17(7): 1791-1795, (2006).

Reidel, A. A., et al. "Compliance with Allopurinol Therapy Among Managed Care Enrollees with Gout: A Retrospective Analysis of Administrative Claims," Journal of Rheumatology, 31:1575-1581, (2004).

Ruggiero, C., et al., "Uric Acid and Inflammatory Markers," European Heat Journal, 27: 1174-1181, (2006).

Saito. H., et al., "Tissue Hypoxia in Sleep Apnea Syndrome Assessed by Uric Acid and Adenosine," Chest, 122: 1686-1694, (2002).

Sautin, Y. Y., et al., "Adverse Effects of the Classic Antioxidant Uric Acid in Adipocytes: NADPH Oxidase-Mediated Oxidative/Nitrosative Stress," Am. J. Physiol. Cell Physiol., 293: C584-C596, (2007).

Schretlen. DJ. et al., "Serum Uric Acid and Cognitive Function in Community-Dwelling Older Adults", Neuropsychology, 21(1): 136-140, (Jan. 2007).

Shankar, A. et al., "Association Between Serum Uric Acid Level and Peripheral Artery Disease," Atherosclerosis, doi 10: 1016, (Epub 2007), vol. 196(2): 74-755 (2008).

Stamp, L., et al. "Gout in Solid Organ Transplantation: A Challenging Clinical Problem", Drugs, 65(18):2593-2611, (2005).

Strasak. AM et al., "Serum Uric Acid and Risk of Cancer Mortality in a Large Prospective Male Cohort," Cancer Causes Control, 18(9): 1021-1029, (2007).

Strasak, AM et al., "The Role of Serum Uric Acid as an Antioxidant Protecting Against Cancer: Prospective Study in More Than 28,000 Older Austrian Women," Annals Oncol., 18(11): 1893-1897, (2007).

Strasak. A.M. et al., "Serum Uric Acid and Risk of Cardiovascular Mortality; A Prospective, Long-Term Study of 83,683 Austrian Men," Clin Chem. 54 (2) 273-284, (2008).

Sundström, J., et al., "Relations of Serum Uric Acid to Longitudinal Blood Pressure Tracking and Hypertension Incidence," Hypertension, 45(1):28-33, (2005).

Syamala, S. et al. "Association Between Serum Uric Acid and Prehypertension Among US Adults," J. Hypertens., 25(8): 1583-1589. (2007).

Tseng, CH, "Independent Association of Uric Acid Levels With Peripheral Artery Disease in Taiwanese Patients With Type 2 Diabetes." Diabet. Med., 21(7):724-729, (2004).

Verhulst, S.L., et al., "Sleep-Disordered Breathing and Uric Acid in Overweight and Obese Children and Adolescents," Chest, 132: 76-80, (2007).

Wallace, K. L., et al., "Increasing Prevalence of Gout and Hyperuricemia over 10 Years Among Older Adults in a Managed Care Population," Journal of Rheumatology, 31:1582-1587, (2004).

Watanabe, S., et al. "Cerebral Oxidative Stress and Mitochondrial Dysfunction in Oxonate-Induced Hyperuricemie Mice", J. Health Science, 52(6): 730-737, (2006).

\* cited by examiner

COMPOUNDS AND METHOD FOR REDUCING URIC ACID

BACKGROUND OF THE INVENTION

Diseases caused by elevated levels of uric acid fall into two major categories: disorders caused by precipitation of uric acid crystals and diseases related to pathological effects of soluble uric acid. Gouty arthritis is the classic example of the former. Deposition of urate crystals in the kidney is also a common cause of renal dysfunction. Elevated levels of soluble uric acid are associated with a variety of disorders, including cardiovascular and renal diseases.

Gout is most commonly manifested as inflammation of one or more of the joints in the body resulting in mild to severe pain. These events may be episodic and/or chronic. Over time gout can result in the destruction of cartilage and bone, development of uric acid crystal deposits, kidney pain and dysfunction as well as kidney stones. Gout can affect other organs as well.

Gout is caused by hyperuricemia and the consequent formation and deposition of uric acid crystals in tissues, joints, kidneys and other organs. The uric acid comes from normal cell metabolism and from some types of foods and beverages. The excessive levels of uric acid are the result of too much uric acid production, impaired clearance by the kidneys (or a combination of excess production and impaired clearance), and also by some forms of medications taken for other health conditions. (Examples include diuretics, pyrazinamide, cyclosporine, low-dose aspirin, nicotinic acid and levodopa). Many types of health conditions can also contribute to hyperuricemia and gout, including alcoholism, leukemia, lymphoma, lung cancer, tumor-lysis syndrome, smoking, psoriasis, obesity, kidney dysfunction, congestive heart failure, starvation, anemia, high blood pressure, diabetes, immobility, Lesch-Nyhan Syndrome, Down syndrome, and thyroid and parathyroid dysfunctions.

Gout is generally divided into four categories based upon progressively more severe symptoms:
1) Asymptomatic. Elevated uric acid levels in the blood, but no overt symptoms.
2) Acute gouty arthritis: Sudden onset of symptoms, often in a single joint (commonly a big toe), and then involving other joints. Symptoms include pain, swelling, redness and fever.
3) Intercritical gout: Asymptomatic phases between gout attacks.
4) Chronic tophaceous gout: A chronic condition that may include frequent attacks, constant mild pain and inflammation of joints, destruction of cartilage and bone, development of uric acid crystal deposits, kidney dysfunction and kidney stones.

Medications currently used to treat the acute symptoms of gout include nonsteroidal anti-inflammatory drugs, colchicine and corticosteroids. All of these medications can produce mild to severe side effects. Other treatments for these acute symptoms are being studied, including antibodies and antagonists to inflammatory cytokines such as Interleukin 1.

Other types of medication are used in order to try to reduce the incidence or severity of future attacks by reducing levels of uric acid. The three principal classes of medication are xanthine oxidase inhibitors (for example, allopurinol), which reduce production of uric acid from xanthine; uricosuric agents (for example, sulfinpyrazone, probenecid, benzbromarone and losartan), which are intended to improve excretion of uric acid by inhibiting reuptake of secreted uric acid in the renal tubules via inhibition of uric acid transporter 1 (URAT1) (See also US Patent Application Publication No. 2007/0010670, published Jan. 11, 2007 (Japan Tobacco Inc.)) or other elements of uric acid reuptake; and uricases, for example a pegylated-uricase such as PURICASE (Savient's pegylated recombinant mammalian uricase). These medications also often result in significant and undesirable side effects. For example, allopurinol has been reported to cause at least 100 cases of Stevens-Johnson/Toxic Epidermal Necrolysis and approximately 30 deaths each year in Europe (Halevy et al., Allopurinol is the most common cause of Stevens-Johnson syndrome and toxic epidermal necrolysis in Europe and Israel. J Am Acad Dermatol. 58(1):25-32, 2008). Probenicid and benzbromarone have been taken off the market in a number of countries due to undesirable side effects, such as liver failure in the case of benzbromarone. Patient compliance in taking these drugs is reportedly very poor (A. A. Reidel et al. "Compliance with Allopurinol Therapy among Managed Care Enrollees with Gout: A Retrospective Analysis of Administrative Claims." Journal of Rheumatology 2004; 31:1575-1581), presumably because of the side effects and/or lack of benefit.

More than 5 million people in the U.S. have gout (National Health and Nutrition Examination Survey 111, 1988-1994). The prevalence of hyperuricemia and gout in the U.S. in 1999 was reported to be 41 per 1,000 and 14 per 1,000 in the U.K. (T. R. Mikuls et al., "Gout Epidemiology: Results for the UK General Practice Research Database, 1990-1999." Annals of the Rheumatic Diseases 2005; 64:267-272). Subsequent reports indicate that the prevalence in the U.S., U.K. and other countries has been climbing steadily. (K. L. Wallace et al., "Increasing Prevalence of Gout and Hyperuricemia over 10 Years Among Older Adults in a Managed Care Population." Journal of Rheumatology 2004; 31: 1582-1587). More recent data suggest that far more than 5 million Americans now have diagnosable gout. (E. Krishnan et al., "Gout in Ambulatory Care Settings in the United States." Journal of Rheumatology 2008; 35(3): 498-501)

Hyperuricemia and gout are particularly significant issues in organ transplant recipients (Stamp, L., et al, "Gout in solid organ transplantation: a challenging clinical problem", Drugs (2005) 65(18): 2593-2611). Uric acid is often elevated in patients with renal transplants, and common immunosupressive drugs such as cyclosporine can cause particularly severe hyperuricemia. In transplant patients, allopurinol is contraindicated due to interactions with some immunosupressants such as azathioprine, and due to bone marrow failure caused by the combination. Furthermore, elevated uric acid may contribute to graft failure (Armstrong, K. A. et al., "Does Uric Acid Have a Pathogenetic Role in Graft Dysfunction and Hypertension in Renal Transplant Patients?" Transplantation (2005) 80(11): 1565-1571). Therefore, there is a particularly acute need for safe agents that reduce hyperuricemia in transplant recipients.

Diseases related to elevated soluble uric acid often involve vascular problems: hypertension (Sundstrom et al., Relations of serum uric acid to longitudinal blood pressure tracking and hypertension incidence. Hypertension. 45(1):28-33, 2005), prehypertension (Syamela, S. et al., Association between serum uric acid and prehypertension among US adults. J Hypertens. 25 (8) 1583-1589, (2007), atherosclerosis (Ishizaka et al., Association between serum uric acid, metabolic syndrome, and carotid atherosclerosis in Japanese individuals. Arterioscler Thromb Vasc Biol. (5):1038-44, 2005), peripheral artery disease (Shankar, A. et al., Association between serum uric acid level and peripheral artery disease. Atherosclerosis doi 10: 1016, 2007), vascular inflammation (Zoccali et al., Uric acid and endothelial dysfunction in essential hypertension. J Am Soc Nephrol. 17(5):1466-71, 2006), heart failure (Strasak, A. M. et al., Serum uric acid and risk of cardiovascular mortality: A prospective, long-term study of 83,683 Austrian men, Clin Chem. 54 (2) 273-284, 2008; Pascual-Figal, Hyperuricaemia and long-term outcome after hospital discharge in acute heart failure patients. Eur J Heart Fail. 2006 Oct. 23; [Epub ahead of print]; Cengel, A., et al., "Serum uric Acid Levels as a Predictor of In-hospital Death in Patients Hospitalized for Decompensated Heart Failure." Acta Cardiol. (October 2005) 60(5): 489-492), myocardial infarctions (Strasak, A. M. et al.; Bos et al., Uric acid is a risk factor for myocardial infarction and stroke: the Rotterdam study. Stroke. 2006 June; 37(6):1503-7), renal dysfunction (Cirillo et al., Uric Acid, the metabolic syndrome, and renal disease. J Am Soc Nephrol. 17(12 Suppl 3):5165-8, 2006; Z. Avram and E. Krishnan, Hyperuricemia—where nephrology meets rheumatology. Rheumatology (Oxford), 47(7): 960-964, 2008), and strokes (Bos et al., 2006). Uric acid directly causes endothelial dysfunction (Kanellis, et al., Uric acid as a mediator of endothelial dysfunction, inflammation, and vascular disease. Semin Nephrol. 25(1):39-42, 2005; Khosla et al, Hyperuricemia induces endothelial dysfunction. Kidney Int. 67(5):1739-42, 2005). In children and adolescents, early-onset essential hypertension is associated with elevated serum uric acid, and reduction of uric acid with allopurinol reduces blood pressure in these patients (Feig and Johnson, The role of uric acid in pediatric hypertension. J Ren Nutrition 17(1): 79-83, 2007; D. I. Feig et al., Effect of allopurinol on blood pressure of adolescents with newly diagnosed essential hypertension. JAMA 300(8): 924-932, 2008. Feig et al. also state that this is a new therapeutic approach but that the side effects of existing drugs to lower uric acid may limit or prevent their use. Hyperuricemia is an independent risk factor in all of these conditions.

Elevated soluble uric acid is also associated with or directly induces inflammatory responses. For example, uric acid is transported into vascular smooth muscle cells via organic acid transporters, especially the urate transporter URAT1, and then stimulates vascular smooth muscle cells to produce C-reactive protein, MCP-1 and other cytokines, thereby stimulating proliferation and other changes associated with atherosclerosis (Price et al., Human vascular smooth muscle cells express a urate transporter. J Am Soc Nephrol. 17(7): 1791-5, 2006; Kang et al., Uric acid causes vascular smooth muscle cell proliferation by entering cells via a functional urate transporter. Am J Nephrol. 2005 25(5):425-33 (2005); Yamamoto et al., Allopurinol reduces neointimal hyperplasia in the carotid artery ligation model in spontaneously hypertensive rats. Hypertens. Res. 29 (11) 915-921, 2006), stimulates human mononuclear cells to produce IL-1β, IL-6 and TNF-α, causes marked increases in TNF-α when infused into mice, activates endothelial cells and platelets, and increases platelet adhesiveness (Coutinho et al., "Associations of Serum Uric Acid with Markers of Inflammation, Metabolic Syndrome, and Subclinical Coronary Atherosclerosis", Amer. J. Hypertens. (2007) 20: 83-89; Levya, F., et al., "Uric Acid in Chronic Heart Failure: A Marker of Chronic Inflammation", Eur. Heart J. (1998) 19(12): 1814-1822). Uric acid has also been shown to inhibit bioavailability of endothelial nitric oxide and activate the renin-angiotensin system. (T. S. Perlstein et al., Uric acid and the state of the intrarenal renin-angiotensin system in humans. Kidney International. 66:1465-1470, 2004). Inokuchi et al. have shown that Interleukin 18 (IL-18) and other inflammatory agents reflect local inflammation associated with gout and that urate crystals accelerate activation of IL-18 (T. Inokuchi et al., Plasma IL-18 and other inflammatory cytokines in patients with gouty arthritis and monosodium urate monohydrate crystal-induced secretion of IL-18. Cytokine. 33(1): 21-27, 206), which appears to have a causative role in renal failure. IL-18 and other cytokines are also significantly elevated in people who do not have gout per se but who merely have elevated uric acid levels (C. Ruggiero et al. Uric acid and inflammatory markers. (C. Ruggiero et al., Uric acid and inflammatory markers. European Heart Journal. 27: 1174-1181, 2006)

Hyperuricemia is also associated with cognitive impairment and other forms of central nervous system dysfunction. (Schretlen, D. J. et al., "Serum Uric Acid and Cognitive Function in Community-Dwelling Older Adults", Neuropsychology (January 2007) 21(1): 136-140; Watanabe, S., et al., "Cerebral Oxidative Stress and Mitochondrial Dysfunction in Oxonate-Induced Hyperuricemic Mice", J. Health Science (2006) 52: 730-737).

Elevated serum uric acid levels are also associated with increased risk of cancer and cancer mortality. (Strasak, A M et al. (2007) Serum uric acid and risk of cancer mortality in a large prospective male cohort. Cancer Causes Control 18 (9) 1021-1029; Strasak, A M et al. (2007) The role of serum uric acid as an antioxidant protecting against cancer: prospective study in more than 28,000 older Austrian women. Annals Oncol 18 (11) 1893-1897; Jee, S A et al. (2004) Serum uric acid and risk of death from cancer, cardiovascular disease or all causes in men Eur. J. Cardiovascular Prev. Rehab. 11 (3) 185-191)

Elevated levels of uric acid are associated with prediabetes, insulin resistance, the development of Type 2 diabetes, and an increased probability of a variety of undesirable conditions in people with diabetes, such as peripheral artery disease, strokes, and increased mortality risk, (Ioachimescu, A. G. et al. (2007) Serum uric acid, mortality and glucose control in patients with Type 2 diabetes mellitus: a PreCIS database study Diabet. Med. 24 (12) 1369-1374; Perry, I. J. et al (1995) Prospective study of risk factors for development of non-insulin dependent diabetes in middle aged British men BMJ 310 (6979) 560-564; Chien, K-L et al. (2008) Plasma uric acid and the risk of Type 2 diabetes in a Chinese community Clin. Chem. 54 (2) 310-316; Sautin, Y.Y. et al. (2007) Adverse effects of the classic antioxidant uric acid in adipocytes: NADPH oxidase-mediated oxidative/nitrosative stress Am. J. Physiol. Cell Physiol. 293: C584-0596; Tseng, C. H. (2004) Independent association of uric acid levels with peripheral artery disease in Taiwanese patients with Type 2 diabetes Diabet. Med. 21 (7) 724-729; Lehto, S. et al. (1998) Serum uric acid is a strong predictor of stroke in patients with non-insulin dependent diabetes mellitus Stroke 29: 635-639.

Elevated levels of uric acid are a defining feature of Lesch-Nyhan Syndrome. People with sleep apnea or sleep-disordered breathing also have elevated of uric acid (Saito, H. et al., Tissue hypoxia in sleep apnea syndrome assessed by uric acid and adenosine. Chest 122: 1686-1694, 2002; Verhulst, S. L., et al., Sleep-disordered breathing and uric acid in overweight and obese children and adolescents. Chest 132: 76-80, 2007)

Elevated uric acid is associated with preeclampsia (Bainbridge, S. A. and Roberts, J. M., Uric acid as a pathogenic factor in preeclampsia. Placenta Dec. 17, 2007 epub ahead of print).

There is a significant medical need for new medications that can safely, conveniently and effectively treat and prevent disorders related to elevation of blood uric acid, whether such diseases are due to crystallization of uric acid or to effects of supranormal (whether by an individual or a population-based standard) levels of soluble uric acid.

SUMMARY OF THE INVENTION

This invention concerns certain therapeutic uses of a Compound of Formula I or a pharmaceutically acceptable salt thereof.

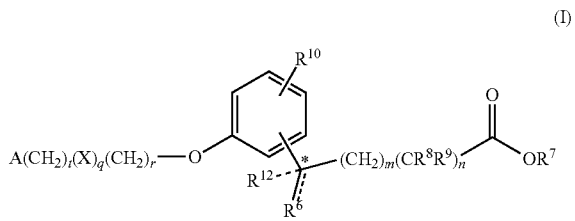

In Formula I, m is 0, 1, 2, 3 or 4; n is 0 or 1; m+n is not more than 4; t is 0 or 1; q is 0 or 1; and r is 0, 1 or 2. $R^6$ is hydrogen, methyl or ethyl and $R^{12}$ is hydrogen or methyl, or $R^6$ is hydroxy and $R^{12}$ is hydrogen, or $R^6$ is O and $R^{12}$ is absent, or $R^6$ and $R^{12}$ together are —$CH_2CH_2$—. $R^7$ is hydrogen or alkyl having from 1 to 3 carbon atoms. One of $R^8$ and $R^9$ is alkyl having from 1 to 3 carbon atoms, and the other is hydrogen or alkyl having from 1 to 3 carbon atoms. $R^{10}$ is hydrogen, halo, alkyl having from 1 to 3 carbon atoms or alkoxy having from 1 to 3 carbon atoms. X is C(O) and r is 0 and t is 0; or X is NH($R^{11}$) wherein $R^{11}$ hydrogen or alkyl having from 1 to 3 carbon atoms. A is phenyl, unsubstituted or substituted by 1 or 2 groups selected from halo, hydroxy, methyl, ethyl, perfluoromethyl, methoxy, ethoxy, and perfluoromethoxy; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl. Esters and other prodrugs of compounds of Formula I are also included in this invention.

This invention provides a method of reducing the uric acid concentration in blood of, or increasing uric acid excretion from, a mammalian subject, comprising administering to the subject a Compound of Formula I or a pharmaceutically acceptable salt thereof in an amount effective to reduce the uric acid concentration in blood of, or increase uric acid excretion from, the subject. This invention provides the use of a biologically active agent in the manufacture of a medicament for reducing the uric acid concentration in blood of, or increasing uric acid excretion from, a mammal wherein the agent is a Compound of Formula I or a pharmaceutically acceptable salt thereof and is formulated for administration in an amount effective to reduce the uric acid concentration in blood of, or increase uric acid excretion from, the subject. This invention provides a pharmaceutical composition for use in reducing the uric acid concentration in blood of, or increasing uric acid excretion from, a mammalian subject comprising a Compound of Formula I or a pharmaceutically acceptable salt thereof in an amount effective to reduce the uric acid concentration in blood of, or increase uric acid excretion from, the subject. This invention provides a kit comprising one or more unit oral doses of a Compound of Formula I or a pharmaceutically acceptable salt thereof, and instructions for administering the Compound of Formula I or pharmaceutically acceptable salt thereof to reduce the uric acid concentration in blood of, or increasing uric acid excretion from, a mammalian subject.

Reducing uric acid as described herein can be used to treat or prevent a variety of conditions including gout (any or all of: asymptomatic gout, acute gouty arthritis, intercritical gout, and chronic tophaceous gout), hyperuricemia, elevated levels of uric acid that do not meet the levels customarily justifying a diagnosis of hyperuricemia, renal dysfunction, kidney stones, cardiovascular disease, risk for developing cardiovascular disease and other consequences of hyperuricemia, cognitive impairment, and early-onset essential hypertension.

This invention is based on the observation that a compound of Formula I that was administered to humans reduced the level of uric acid in the blood of human patients and increased excretion of uric acid, as described in Examples 1 through 5. The in vivo experiments utilized a compound in which $R^6$ is O. Because Compounds CF and CR are metabolites of Compound BI, it is believed that Compounds of Formula I in which $R^6$ is hydrogen or hydroxy will also reduce in vivo blood levels of uric acid and increase excretion of uric acid. This invention is also based on the observation that compounds of Formula I, including compounds in which $R^6$ is O, hydrogen or hydroxy, inhibited URAT1 in vitro, as shown in Example 6 Inhibition of URAT1 is an established in vitro model for lowering uric acid in vivo.

This invention also provides the following compounds, their pharmaceutically acceptable salts, esters and prodrugs:
DQ 2-(3-(2,6-Dimethylbenzyloxy)-4-methoxyphenyl)acetic acid;
EB Methyl 3-(3-(2,6-dimethylbenzyloxy)phenyl)-3-oxopropanoate;
DR 2-(3-(2,6-Difluorobenzyloxy)phenyl)acetic acid;
DS 4-(3-(2,6-Dichlorobenzyloxy)phenyl)-4-oxobutanoic acid;
DT 2-(3-(2,6-Dimethylbenzyloxy)phenyl)propanoic acid;
DU 2-(3-(4-Trifluoromethyl)benzyloxy)phenyl)acetic acid;
DV 2-(3-(2,6-Dimethylbenzyloxy)phenyl)butanoic acid;
DW 2-(3-(3,5-Dimethylbenzyloxy)phenyl)acetic acid;
DX 2-(3-(2,4-Dimethylbenzyloxy)phenyl)acetic acid;
DY 2-(3-(2,6-Dimethoxylbenzyloxy)phenyl)butanoic acid;
DZ 2-(3-(Benzyloxy)phenyl)acetic acid; and
EA 2-(2-(2,6-Dimethylbenzyloxy)phenyl)acetic acid.
EC 2-(3-(2,6-Dimethylbenzyloxy)phenyl)propanoic acid
ED 2-(3-(2,6-Dimethylbenzyloxy)phenyl)butanoic acid
EE 2-(3-(2,6-Dimethylbenzyloxy)phenyl)-2-methylpropanoic acid
EF 1-(3-(2,6-Dimethylbenzyloxy)phenyl)cyclopropanecarboxylic acid
EG 2-(3-(2-Chloro-6-methylbenzyloxy)phenyl)acetic acid
EH 2-(3-(2,6-Dimethylbenzyloxy)-4-methylphenyl)acetic acid
EI 2-(3-(2,6-Dimethylbenzyloxy)-4-fluorophenyl)acetic acid

DETAILED DESCRIPTION OF THE INVENTION

Definitions

Figure 1:
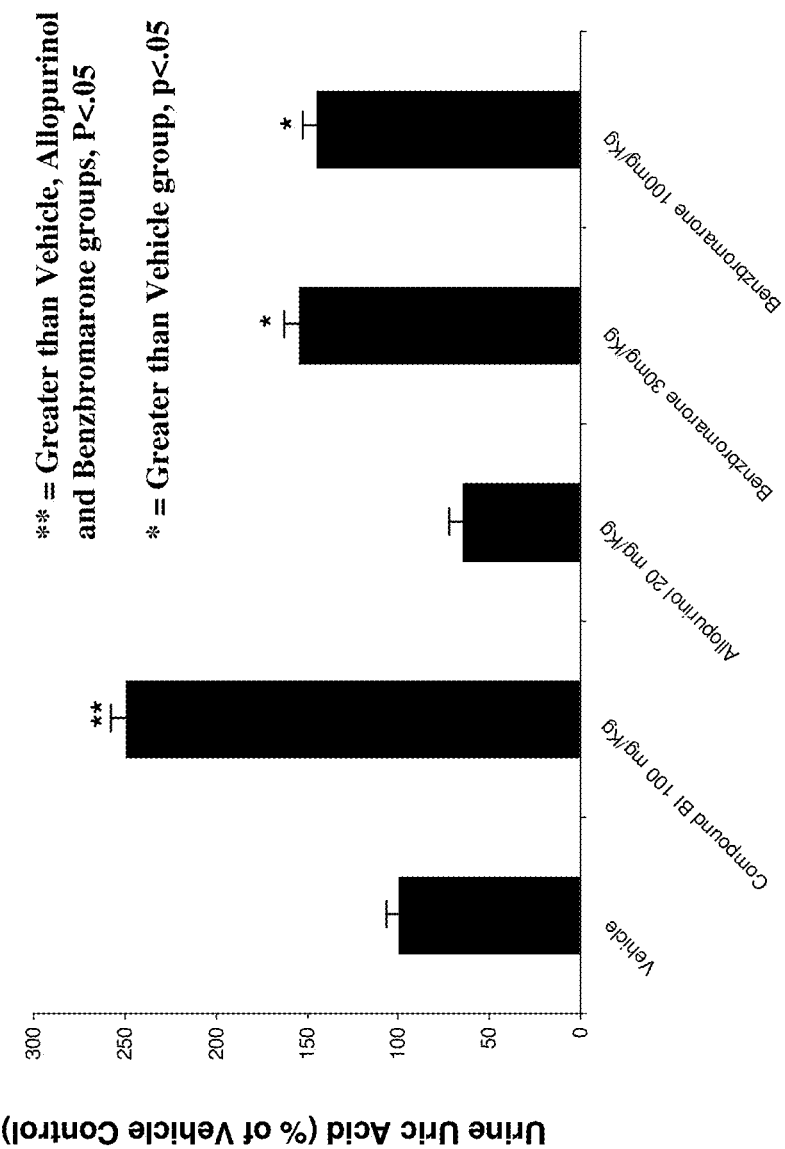
FIG. 1: Compound BI increases excretion of uric acid in urine of mice treated with the uricase inhibitor potassium oxonate.

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, and bromo.

As used herein the term "perfluoro" as in perfluoromethyl or perfluoromethoxy, means that the group in question has fluorine atoms in place of all of the hydrogen atoms.

The bond between $R^6$ and the carbon atom to which it is directly bonded is depicted in Formula I above by a solid line together with a dashed line. This depiction reflects that the bond in question can be either a single bond, when $R^6$ is hydrogen, methyl, ethyl or hydroxy, or a double bond, when $R^6$ is O.

The asterisk in the depiction of Formula I above indicates a possible chiral center, and that carbon is chiral when $R^6$ and $R^{12}$ are different, i.e., when $R^6$ is hydroxy, methyl or ethyl and $R^{12}$ is hydrogen or when $R^6$ is hydrogen, hydroxy or ethyl and $R^{12}$ is methyl. In such cases, this invention provides the racemate, the (R) enantiomer, and the (S) enantiomer, of the Compounds of Formula I, all of which are believed to be active. In the synthesis examples a racemate is indicated by a wavy bond. Mixtures of these enantiomers can be separated by using HPLC, for example as described in Chirality 11:420-425 (1999).

The term "prodrug(s)" of a compound of interest refers to other compounds that are cleaved, typically in vivo, to yield the compound of interest.

Certain chemical Compounds are referred to herein by their chemical name or by the two-letter code shown below. The compounds listed below are included within the scope of Formula I shown above.

BI 4-(3-(2,6-Dimethylbenzyloxy)phenyl)-4-oxobutyric acid
CF 3-(2,6-Dimethylbenzyloxy)phenylacetic acid
CR 4-(3-(2,6-Dimethylbenzyloxy)-phenyl)-4(R)-hydroxybutanoic acid
DQ 2-(3-(2,6-Dimethylbenzyloxy)-4-methoxyphenyl)acetic acid
AN 4-(3-(2-Methylbenzyloxy)phenyl)-4-oxobutanoic acid
AW 4-(3-(2,6-Difluorobenzyloxy)phenyl)-4-oxobutanoic acid
BJ 4-(3-(2-Fluoro-6-methylbenzyloxy)phenyl)-4-oxobutanoic acid
BP 4-(3-(2,6-Dimethylbenzyloxy)phenyl)-2,2-dimethyl-4-oxobutanoic acid
BS 4-(3-(2,6-Dimethylbenzyloxy)phenyl)butanoic acid
EB Methyl 3-(3-(2,6-dimethylbenzyloxy)phenyl)-3-oxopropanoate
CD 5-(3-(2,6-Dimethylbenzyloxy)phenyl)-5-oxopentanoic acid
CQ 2-(3-(2,6-Dimethylbenzyloxy)phenyl)-2-oxoacetic acid
CK 5-(3-(2,6-Dimethylbenzyloxy)phenyl)pentanoic acid
CM 3-(3-(2,6-Dimethylbenzyloxy)phenyl)propanoic acid
DR 2-(3-(2,6-Difluorobenzyloxy)phenyl)acetic acid
DS 4-(3-(2,6-Dichlorobenzyloxy)phenyl)-4-oxobutanoic acid
DT 2-(3-(2,6-Dimethylbenzyloxy)phenyl)propanoic acid
DU 2-(3-(4-Trifluoromethyl)benzyloxy)phenyl)acetic acid
DN 2-(3-(2,4-bis(trifluoromethyl)benzyloxy)phenyl)acetic acid
DV 2-(3-(2,6-Dimethylbenzyloxy)phenyl)butanoic acid
DW 2-(3-(3,5-Dimethylbenzyloxy)phenyl)acetic acid
DX 2-(3-(2,4-Dimethylbenzyloxy)phenyl)acetic acid
DY 2-(3-(2,6-Dimethoxylbenzyloxy)phenyl)acetic acid
DZ 2-(3-(Benzyloxy)phenyl)acetic acid
BH 4-(3-(Cyclopropylmethoxy)phenyl)-4-oxobutanoic acid
DP 4-(3-(2,6-Dimethylbenzoyloxy)phenyl)-4-oxobutanoic acid
AB 4-(4-(2-Methoxybenzyloxy)phenyl)-4-oxobutanoic acid
AF 4-oxo-4-(4-(pyridin-2-ylmethoxy)phenyl)butanoic acid
AG 4-(4-(Benzyloxy)phenyl)-4-oxobutanoic acid
AH 4-(4-(2,6-Difluorobenzyloxy)phenyl)-4-oxobutanoic acid
AI 4-(4-(2-Chlorobenzyloxy)phenyl)-4-oxobutanoic acid
AM 4-(4-(2-((2-Fluorobenzyl)(methyl)amino)ethoxy)phenyl)-4-oxobutanoic acid hydrochloride
AT 4-(4-(2,5-Dimethylbenzyloxy)phenyl)-4-oxobutanoic acid
AY 4-(4-(2-Trifluoromethylbenzyloxy)phenyl)-4-oxobutanoic acid
BM 4-(4-(2,6-Dimethylbenzyloxy)phenyl)-4-oxobutanoic acid
BT 4-(4-(2,6-Dimethylbenzyloxy)-3-methoxyphenyl)-4-oxobutanoic acid
DO 2-(4-(2,6-Dimethylbenzyloxy)phenyl)acetic acid
EA 2-(2-(2,6-Dimethylbenzyloxy)phenyl)acetic acid
EC 2-(3-(2,6-Dimethylbenzyloxy)phenyl)propanoic acid
ED 2-(3-(2,6-Dimethylbenzyloxy)phenyl)butanoic acid
EE 2-(3-(2,6-Dimethylbenzyloxy)phenyl)-2-methylpropanoic acid
EF 1-(3-(2,6-Dimethylbenzyloxy)phenyl)cyclopropanecarboxylic acid
EG 2-(3-(2-Chloro-6-methylbenzyloxy)phenyl)acetic acid
EH 2-(3-(2,6-Dimethylbenzyloxy)-4-methylphenyl)acetic acid
EI 2-(3-(2,6-Dimethylbenzyloxy)-4-fluorophenyl)acetic acid As used herein the transitional term "comprising" is open-ended. A claim utilizing this term can contain elements in addition to those recited in such claim.

As used in the claims the word "or" means "and/or" unless such reading does not make sense in context. So for example the phrase "reducing the uric acid concentration in blood of or increasing uric acid excretion from, a mammalian subject" is equivalent to "reducing the uric acid concentration in blood of and/or increasing uric acid excretion from, a mammalian subject."

Compounds of the Invention

In an embodiment of the invention described in the Summary above, A is substituted (as defined above) or unsubstituted phenyl, for example 2,6-dimethylphenyl. In other embodiments r is 1, t is 0, and q is 0. In another embodiment $R^{10}$ is methoxy.

The two bulky substituents (i.e. other than $R^{10}$) around the central phenyl ring can be located in the ortho, meta or para position with respect to one another. Preferably they are in the meta position with respect to one another.

In an embodiment of Formula I, A is substituted (as defined above) or unsubstituted phenyl, t is 0, q is 0, r is 1, $R^{10}$ is hydrogen, n is 0, m is 0, 2 or 4. In a more specific embodiment A is 2,6-dimethylphenyl.

In an embodiment of this invention the Compound is represented by Formula IA. In a more specific embodiment the Compound is represented by Formula IA1. In Formula IA the variables are as defined above. In Formula IA1 two of $R^1$, $R^2$, $R^3$, $R^4$ and $R^5$ are selected from the group consisting of hydrogen, halo, hydroxy, methyl, ethyl, perfluoromethyl, methoxy, ethoxy and perfluoromethoxy, the remainder are hydrogen; and the other variables are as defined above. In more specific embodiments A is 2,6-dimethylphenyl, i.e. $R^1$ is methyl and $R^5$ is methyl. Nonlimiting examples of compounds of Formula I include Compounds AF, AG, AH, AT, BM, BT, DO and EA. Nonlimiting examples of compounds of Formula IA include Compounds BH, DP and EG. Nonlimiting examples of compounds of Formula IA1 include Compounds BI, CF, CR, DQ, AN, AW, BJ, BP, BS, EB, CD, CQ, CK, CM, DR, DS, DT, DU, DN, DV, DW, DX, DY and DZ, EB, EC, ED, EF, EH and EI.

In an embodiment of Formula IA1, $R^{10}$ is hydrogen, m is 0, 2 or 4; and n is 0. Preferably $R^1$ is methyl and $R^5$ is methyl.

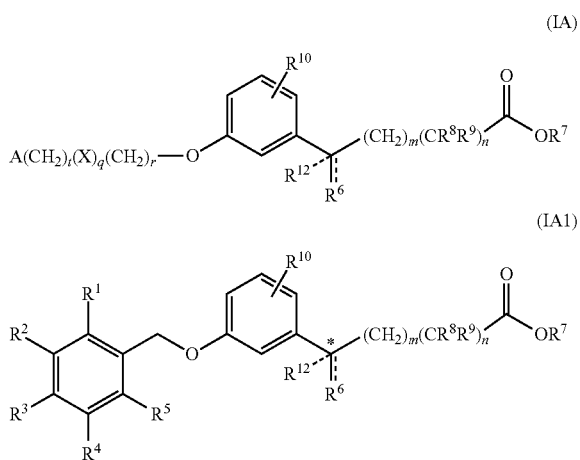

The compounds of Formula I can be made in accordance with the reaction schemes below. In addition, many of the compounds of Formula I can be made according to methods described in WO 02/100341, WO 04/073611, WO 04/091486, WO 04/098496, WO 07/087,506, WO 07/146,768, and PCT/US2009/030845, the contents of which are incorporated herein by reference.

Reaction Schemes

The compound of formula I where m is 0, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is hydrogen or methyl, or ethyl and $R^{12}$ is hydrogen or methyl or $R^6$ and $R^{12}$ together are —$CH_2CH_2$—. One of $R^8$ and $R^9$ is alkyl having from 1 to 3 carbon atoms, and the other is hydrogen or alkyl having from 1 to 3 carbon atoms, and X is C(O), r is 0 and t is 0; X is NH($R^{11}$) wherein $R^{11}$ is hydrogen or alkyl having 1 to 3 carbon atoms. $R^7$ is hydrogen or alkyl having from 1 to 3 carbon atoms, i.e. compounds of formula:

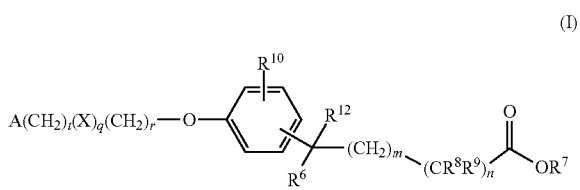

wherein A is described as above, can be prepared via reaction scheme of Scheme 1.

In the reaction scheme of Scheme 1, A, q, t, m, n, r, $R^6$, $R^7$, $R^{10}$ and $R^{12}$ are as above. $R^{13}$ is alkyl group having 1 to 2 carbon atoms. $R^{17}$ is alkyl group having 1 to 3 carbon atoms or benzyl group. $R^{14}$ is chloro or bromo and Y is a halide.

The compound of formula II can be alkylated with the compound of formula III or with the compound of formula (IV) via reaction of step (a). The reaction is carried out in a suitable solvent, such as tetrahydrofuran, tetrahydrofuran/1,3-dimethyl-3,4,5,6-tetrahydro-2 (1H)-pyrimidinone, toluene, N,N-dimethylformamide, tetrahydrofuran/hexamethylphosphoramide and the like. Generally, the reaction is carried out in the presence of 2 to 3 molar equivalents of base to produce the compound of formula V where $R^6$ is alkyl having 1 to 2 carbon atoms and $R^{12}$ is hydrogen or 4 to 6 molar equivalents of base to produce the compounds of formula V where $R^6$ and $R^{12}$ are alkyl having 1 to 2 carbon atoms or together are —$CH_2CH_2$—. The conventional base for this purpose can be sodium hydride, potassium hydride, sodium hydroxide, tetrabutylammonium hydroxide, potassium bis(trimethylsilyl)amide, lithium bis(trimethylsilyl)amide, lithium diisopropylamide and the like. In carrying out this reaction it is generally preferred to utilize aq. solution of tetrabutylammonium hydroxide and aq. sodium hydroxide. The reaction can be carried out at temperatures from –78° C. to 25° C. for 6 to 72 hours. The conventional techniques such as extraction, evaporation, chromatography and recrystallization can be utilized to purify the product. In the case where $R^6$ and $R^{12}$ are hydrogens, the compound of Formula II can be converted to the compound of Formula VI by hydrolysis of nitriles to acid without the alkylation step A.

The compound of formula V can be converted to the compound of formula VI via reaction step (b) by acid or base hydrolysis. In carrying out this reaction it is generally preferred to utilize basic hydrolysis, for example aqueous sodium hydroxide. Any of the conditions conventionally used in hydrolysis of nitrile to produce carboxylic acid can be utilized to carry out the reaction of step (b).

The compound of formula VI can be converted to the compound of formula VII by esterification of compound of formula VI with methanol, ethanol or propanol. The reaction can be carried out either by using catalyst for example $H_2SO_4$, TsOH and the like or by using dehydrating agent for example dicyclohexylcarbodiimide and the like. Any of the conditions conventional in such esterification reactions can be utilized to carry out the reaction of step (c).

In the case where X is C(O), the compound of formula VI can be reacted with the benzyl bromide in the presence of base for example, triethylamine, potassium carbonate to produce the compound of formula VII. Any conditions conventional in such reactions can be utilized to carry out the reaction of step (c). The compound of formula VII can be converted to the compound of formula XI first by de-alkoxylation by utilizing lewis acid for example $BBr_3$ or $BCl_3$ in dichloromethane or chloroform at low temperature for example –78° C. Any of the conditions conventional in such reactions can be utilized to carry out the reaction via the reaction of step (d).

In the second step, the product of reaction step (d) can be converted to the compound of formula XI via reaction of step (e) using Mitsunobu condensation with IX utilizing triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (e).

In the case where X is C(O), the compound of formula VII can be reacted with the compound of formula IX in the presence of dehydrating agent for example dicyclohexylcarbodiimide. Any conditions conventional in such reactions can be utilized to carry out the reaction of step (e).

The compound of formula XI can also be prepared by etherifying or alkylating the hydroxyl from step (d) with the compound of formula X via reaction of step (e). In the compound of formula X, Y, include but are not limited to mesyloxy, tosyloxy, chloro, bromo, iodo, and the like. Any conventional method of etherifying of a hydroxyl group by reaction with a leaving group can be utilized to carry out the reaction of step (e).

In the case where X is C(O), the compound of formula VII can be reacted with the compound of formula X where Y is chloro. Generally, the reaction is carried out in the presence of base for example pyridine. Any conditions conventional in such reactions can be utilized to carry out the reaction of step (e). The compound of formula XI is the compound of formula I where m is 0, n is 0 and $R^7$ is alkyl having 1 to 3 carbon atoms. The compound of formula XI can be converted to the compound of formula XII via reaction of step (f) where m is 0, n is 0 and $R^7$ is H by ester hydrolysis. Any conventional method of ester hydrolysis will produce the compound of formula I where $R^7$ is H.

In the case where X is C(O), the benzyl group can be removed by catalytic hydrogenation to give the compound of formula I where $R^7$ is H. Any conditions conventional for catalytic hydrogenation reactions can be utilized to produce the compound of formula I.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

atoms, and X is C(O), r is 0 and t is 0; X is NH($R^{11}$) wherein $R^{11}$ is hydrogen or alkyl having 1 to 3 carbon atoms. $R^7$ is hydrogen or alkyl having from 1 to 3 carbon atoms, i.e. compounds of formula:

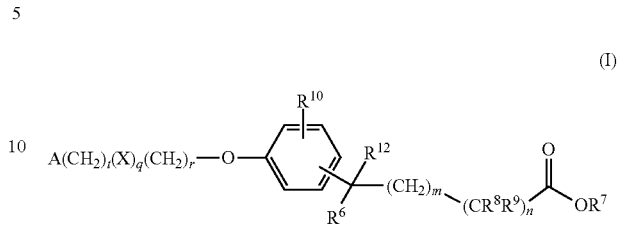

(I)

wherein A is described as above, can be prepared via reaction scheme of Scheme 2. In the reaction scheme of Scheme 2, A, q, t, m, r, $R^6$, $R^7$, $R^{10}$ and $R^{12}$ are as above, and Y is a halide. $R^{17}$ is alkyl group having 1 to 3 carbon atoms or benzyl group.

The compound of formula VII can be reduced to the compound of formula XIII via reaction of step (g). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (g).

The compound of formula XIII can be converted to the compound of formula XIV by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (h).

Reaction Scheme 1

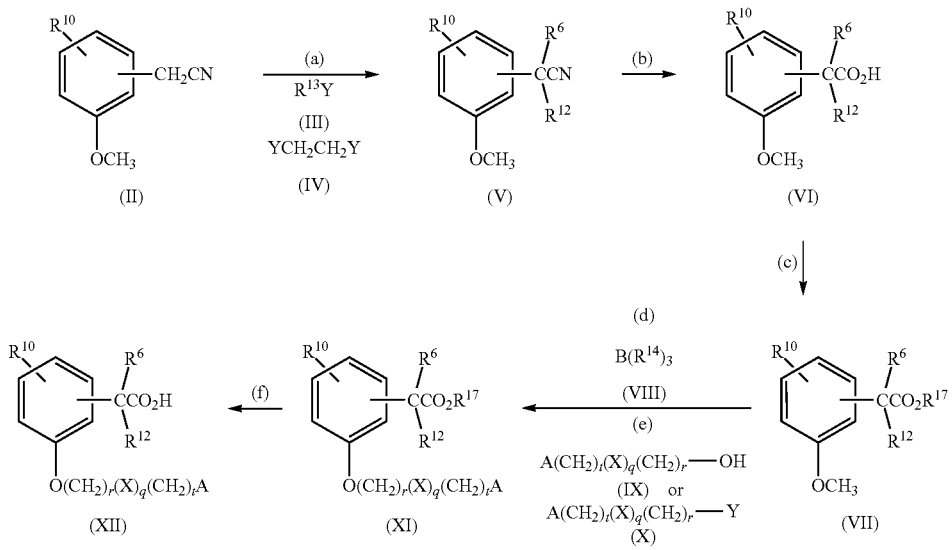

The compound of formula I where m is 1 to 4, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is hydrogen or methyl, or ethyl and $R^{12}$ is hydrogen or methyl or $R^6$ and $R^{12}$ together are —$CH_2CH_2$—. One of $R^8$ and $R^9$ is alkyl having from 1 to 3 carbon atoms, and the other is hydrogen or alkyl having from 1 to 3 carbon The compound of formula XIV can be converted to the compound of formula XV by reacting Y with an alkali metal cyanide for example sodium, potassium or copper cyanide. The reaction is carried out in a suitable solvent, such as ethanol, dimethyl sulfoxide and the like. Any of the conditions conventionally used in the preparation of nitriles can be utilized to carry out the reaction of step (i).

The compound of formula XV can be converted to the compound of formula XVI via reaction step (j) by acid or base hydrolysis. In carrying out this reaction it is generally preferred to utilize basic hydrolysis, for example aqueous sodium hydroxide in ethanol, tetrahydrofuran: water and the like. Any of the conditions conventionally used in hydrolysis of nitrile can be utilized to carry out the reaction of step (j).

The compound of formula XVI can be converted to the compound of formula XVII via reaction of step (k) in the same manner as described hereinbefore in connection with the reaction of step (c).

The compound of formula XVII can be converted to the compound of formula XVIII via reaction of step (l) in the same manner as described hereinbefore in connection with the reaction of step (d) and reaction of step (e).

The compound of formula XVIII is the compound of formula I where m is 1, n is 0 and $R^7$ is alkyl group having 1 to 3 carbon atoms.

The compound of formula XVIII can be converted to the compound of formula I where m is 1, n is 0 and $R^7$ is H in the same manner as described hereinbefore in connection with the reaction of step (f).

The compound of formula XIV can be reacted with diethyl malonate utilizing a suitable base for example sodium hydride to give the compound of formula XIX. The reaction is carried out in suitable solvent, such as N,N-dimethylformamide, tetrahydrofuran and the like. Any of the conditions conventional in such alkylation reactions can be utilized to carry out the reaction of step (m).

The compound of formula XIX can be hydrolyzed and decarboxylated utilizing sodium hydroxide in suitable solvent, such as ethanol-water to give the compound of formula XX. Any of the conditions conventional in such reactions can be utilized to carry out the reaction of step (n). The compound of formula XX can be converted to the compound of formula XXI via reaction of step (o) in the same manner as described hereinbefore in connection with the reaction of step (c). The compound of formula XXI can be converted to the compound of formula XXII via reaction of step (p) in the same manner as described hereinbefore in connection with the reaction of step (d) and reaction of step (e).

The compound of formula XXII is the compound of formula I where m is 2, n is 0 and $R^7$ is alkyl group having 1 to 3 carbon atoms. The compound of formula XXII can be converted to the compound of formula I where m is 2, n is 0 and $R^7$ is H in the same manner as described hereinbefore in connection with the reaction of step (f).

The compound of formula XX can be reduced to give the compound of formula XXIII via reaction of step (q). This reaction can be carried out in the same manner as described hereinbefore in the reaction of step (g).

The compound of formula XXIII can be converted to the compound of formula XXIV via reaction of step (r) in the same manner as described hereinbefore in connection with the reaction of step (h).

The compound of formula XXIV can be converted to the compound of formula XXV via reaction of step (s) in the same manner as described hereinbefore in connection with the reaction of step (i).

The compound of formula XXV can be converted to the compound of formula XXVI via reaction of step (t) in the same manner as described hereinbefore in connection with the reaction of step (j).

The compound of formula XXVI can be converted to the compound of formula XXVII via reaction of step (u) in the same manner as described hereinbefore in connection with the reaction of step (c).

The compound of formula XXVII can be converted to the compound of formula XXVIII via reaction of step (v) in the same manner as described hereinbefore in connection with the reaction of step (d) and reaction of step (e). The compound of formula XXVIII is the compound of formula I where m is 3, n is 0 and $R^7$ is alkyl group having 1 to 3 carbon atoms. The compound of formula XXVIII can be converted to the compound of formula I where m is 3, n is 0 and $R^7$ is H in the same manner as described hereinbefore in connection with the reaction of step (f).

The compound of formula XXIV can be converted to the compound of formula XXIX via reaction of step (w) in the same manner as described hereinbefore in connection with the reaction of step (m).

The compound of formula XXIX can be converted to the compound of formula XXX via reaction of step (x) in the same manner as described hereinbefore in connection with the reaction of step (n).

The compound of formula XXX can be converted to the compound of formula XXXI via reaction of step (y) in the same manner as described hereinbefore in connection with the reaction of step (c).

The compound of formula XXXI can be converted to the compound of formula XXXII via reaction of step (z) in the same manner as described hereinbefore in connection with the reaction of step (d) and reaction of step (e).

The compound of formula XXXII is the compound of formula I where m is 4, n is 0 and $R^7$ is alkyl group having 1 to 3 carbon atoms.

The compound of formula XXXII can be converted to the compound of formula I where m is 4, n is 0 and $R^7$ is H in the same manner as described hereinbefore in connection with the reaction of step (f).

The products in all the steps can be isolated and purified by techniques such as extraction, evaporation, chromatography, and recrystallization.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 2

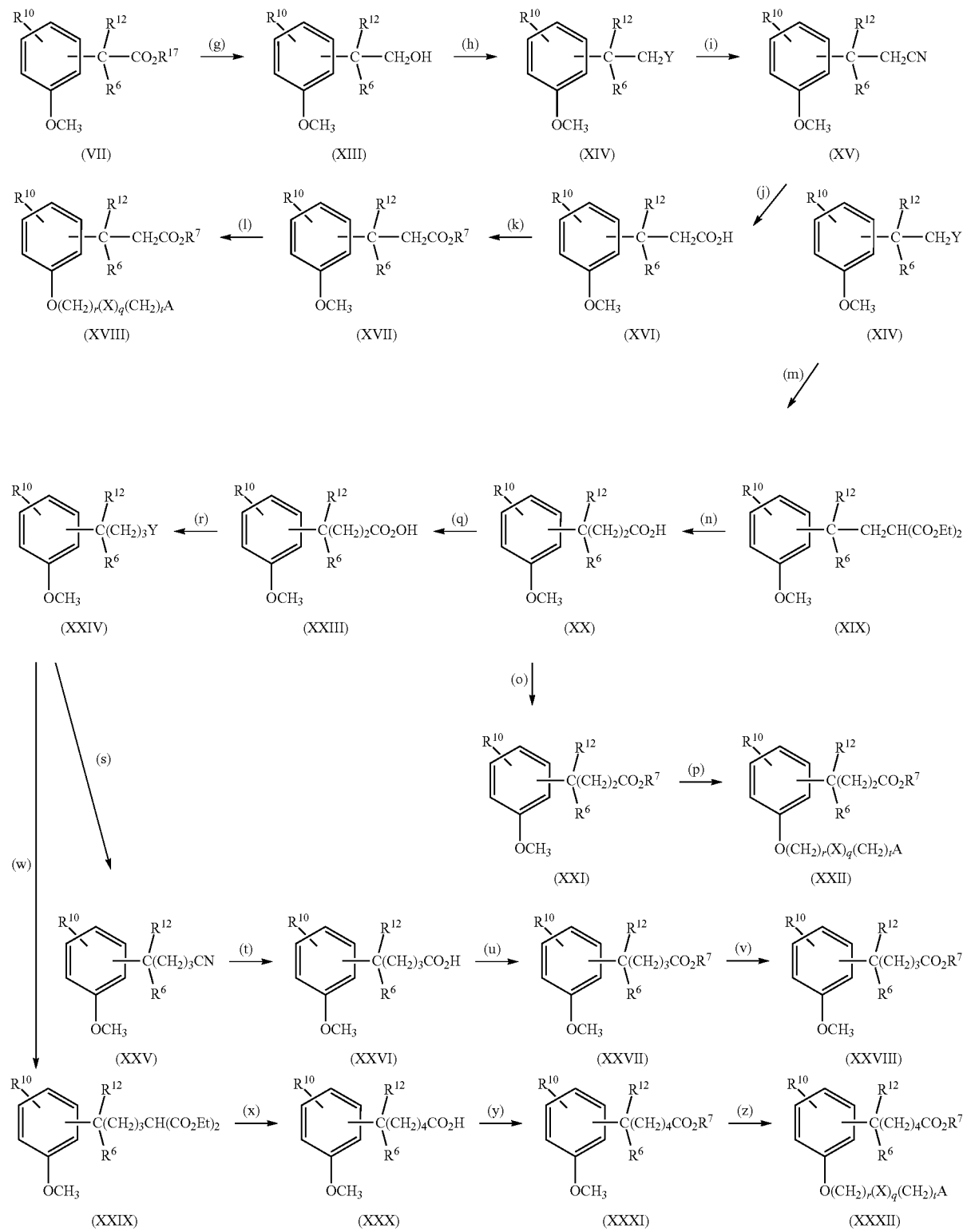

The compound of formula I where m is 0 to 3, q is 0 or 1, t is 0 or 1, and r is 0, 1 or 2, n is 1, $R^{10}$ is hydrogen, halo, alkoxy having from 1 to 3 carbon atoms or alkyl having from 1 to 3 carbon atoms, $R^6$ is hydrogen or methyl, or ethyl and $R^{12}$ is hydrogen or methyl or $R^6$ and $R^{12}$ together are —$CH_2CH_2$—. One of $R^8$ and $R^9$ is alkyl having from 1 to 3 carbon atoms, and the other is hydrogen or alkyl having from 1 to 3 carbon atoms, and X is C(O), r is 0 and t is 0; X is NH($R^{11}$) wherein $R^{11}$ is hydrogen or alkyl having 1 to 3 carbon atoms. $R^7$ is hydrogen or alkyl having from 1 to 3 carbon atoms, i.e. compounds of formula:

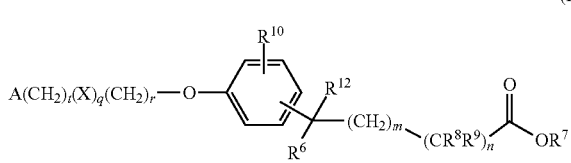

(I)

wherein A is described as above, can be prepared via reaction scheme of Scheme 3.

In the reaction scheme of Scheme 3, A, q, t, m, n, r, $R^7$, $R^8$, $R^9$ and $R^{10}$ are as above, p is 2 to 4, s is 1 to 3 and Y is a halide. $R^{13}$ is alkyl group having 1 to 3 carbon atoms. $R^{15}$ is alkyl group having 1 to 3 carbon atoms or benzyl group.

The compound of formula XXXIII can be converted to the compound of formula XXXV via reaction of step (a') using Wittig reaction by treating the compound of formula XXXIII with the compound of formula XXXIV. Any conventional method of reacting an aldehyde with a triarylphosphine hydrohalide can be utilized to carry out the reaction of step (a'). Any of the conditions conventional in Wittig reactions can be utilized to carry out the reaction of step (a').

The compound of formula XXXV can be converted to the compound of formula XXXVI by reduction of alkene via catalytic hydrogenation in the presence of transition metal catalyst for example, raney nickel, palladium-on-charcoal, platinum metal or its oxide under hydrogen atmosphere. Any of the conditions conventional in such catalytic hydrogenation can be utilized to carry out the reaction of step (b').

The compound of formula XXXVI can be alkylated with the compound of formula III to produce the compound of formula XXXVII via reaction of step (c'). The reaction is carried out in a suitable solvent, such as tetrahydrofuran, tetrahydrofuran/1,3-dimethyl-3,4,5,6-tetrahydro-2 (1H)-pyrimidinone, terahydrofuran/hexamethylphosphoramide and the like. Generally, the reaction is carried out in the presence of 2 to 3 molar equivalents of base to produce the compound of formula XXXVII where one of $R^8$ and $R^9$ is alkyl having 1 to 3 carbon atoms other is hydrogen or 4 to 6 molar equivalents of base to produce the compound of formula XXXVII where $R^8$ and $R^9$ are alkyl having 1 to 3 carbon atoms. The conventional base can be potassium bis(trimethylsilyl)amide, lithium bis(trimethylsilyl)amide, lithium diisopropylamide and the like. Generally, the reaction is carried out at temperatures from −78° C. to 25° C. for 6 to 72 hours. The conventional techniques such as extraction, evaporation, chromatography and recrystallization can be utilized to purify the product.

In the compound of formula XXXVII, m is 0 to 3 and n is 1.

The compound of formula XXXVII can be converted to the compound of formula XXXVIII by de-alkoxylation by utilizing lewis acid for example BBr₃ or BCl₃ in dichloromethane or chloroform at low temperature for example −78° C. Any of the conditions conventional in such reactions can be utilized to carry out the reaction of step (d').

The compound of formula XXXVIII can be converted to the compound of formula XXXIX via reaction of step (e') in the same manner as described hereinbefore in connection with the reaction of steps (e).

The compound of formula XXXIX is the compound of formula I where m is 0 to 3, n is 1 and $R^7$ is an alkyl group having 1 to 3 carbon atoms. The compound of formula XXXIX can be converted to the compound of formula XL via reaction of step (f') in the same manner as described hereinbefore in connection with the reaction of steps (f). The compound of XL is the compound of formula I where m is 0 to 3, n is 1 and $R^7$ is H.

The conventional techniques such as extraction, evaporation, chromatography and recrystallization can be utilized to purify the products. If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected after the reaction of step (e') utilizing suitable deprotecting reagents such as those described in Protective Groups in Organic Synthesis by T. Greene.

Reaction Scheme 3

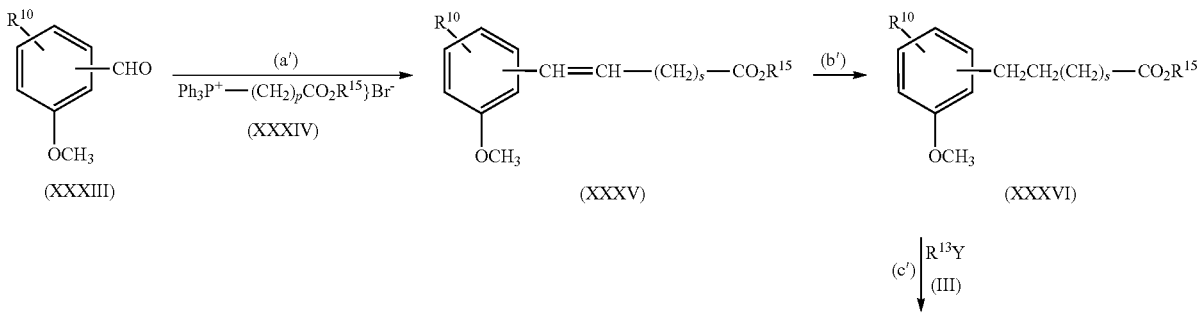

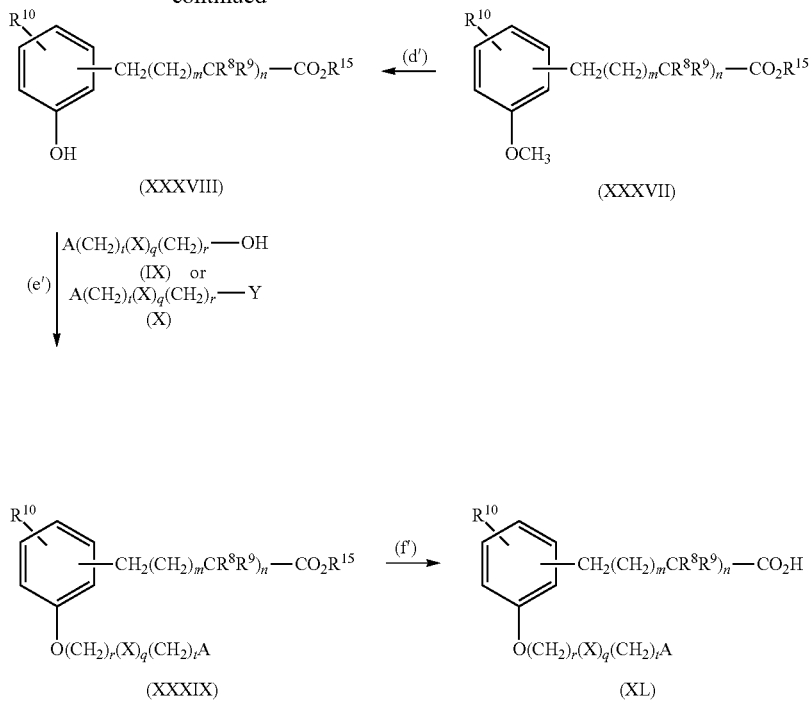

The compound of formula I where m is 0, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is O and $R^{12}$ is absent, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is NH($R^{11}$) wherein $R^{11}$ is hydrogen or alkyl having 1 to 3 carbon atoms, i.e. compounds of formula:

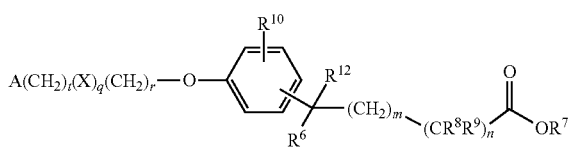

(I)

wherein A is described as above, can be prepared via reaction scheme of Scheme 4.

In the reaction scheme of Scheme 4, A, q, t, r, $R^7$ and $R^{10}$ are as above. Y is a leaving group. The compound of formula XLI can be converted to the compound of formula XLII via reaction of step (g') using Mitsunobu condensation of XLI with IX using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (g').

The compound of formula XLII can also be prepared by etherifying or alkylating the compound of formula XLI with the compound of formula X via the reaction of step (h') by using suitable base such as potassium carbonate, sodium hydride, triethylamine, pyridine and the like. In the compound of formula X, Y, include but are not limited to mesyloxy, tosyloxy, chloro, bromo, iodo, and the like. Any conventional conditions to alkylate a hydroxyl group with a leaving group can be utilized to carry out the reaction of step (h'). The reaction of step (h') is preferred over step (g') if compound of formula X is readily available. The compound of formula XLII can be converted to the compound of formula XLIV via reaction of step (i') by oxidation of methyl group with selenium dioxide (XLII) in the presence of pyridine. Generally the reaction is carried out at temperatures of from 25° C.-100° C. The product can be isolated and purified by techniques such as extraction, evaporation, chromatography, and recrystallization. The compound of formula XLIV is the compound of formula I where m is 0, n is 0, $R^6$ is O, $R^{12}$ is absent and $R^7$ is H.

The compound of formula XLIV can be converted to the compound of formula XLV by esterification of compound of formula XLIV with methanol, ethanol or propanol. The reaction can be carried out either by using catalyst for example $H_2SO_4$, TsOH and the like or by using dehydrating agent for example dicyclohexylcarbodiimide and the like. Any of the conditions conventional in such esterification reactions can be utilized to carry out the reaction of step (j').

The compound of formula XLV is the compound of formula I where m is 0, n is 0 and $R^7$ is an alkyl having 1 to 3 carbon atoms. The product can be isolated and purified by techniques such as extraction, evaporation, chromatography, and recrystallization.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 4

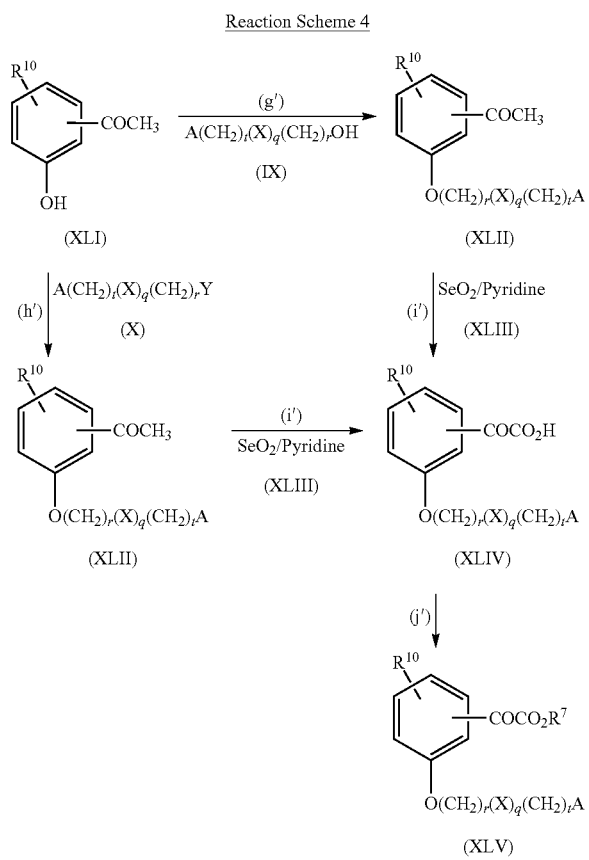

The compound of formula I where m is 1, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is O and $R^{12}$ is absent, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is $NH(R^{11})$ wherein $R^{11}$ is hydrogen or alkyl having 1 to 3 carbon atoms, i.e. compounds of formula:

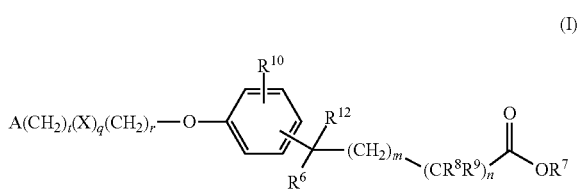

(I)

wherein A is described as above, can be prepared via reaction scheme of Scheme 5. In the reaction scheme of Scheme 5, A, q, t, r, $R^7$ and $R^{10}$ are as above. Y is a leaving group.

The compound of formula XLII (prepared in the same manner as described in the reaction of scheme 4) can be reacted with dialkyl carbonate via reaction of step (k') in the presence of a suitable base such as sodium hydride and the like. The reaction can be carried out in conventional solvents such as N,N'-dimethylformamide, tetrahydrofuran, dichloromethane and the like followed by addition of dialkyl carbonate such as dimethyl or diethyl or dipropyl carbonate to produce the corresponding compound of formula XLVI. Any conditions conventional in such alkylation reactions can be utilized to carry out the reaction of step (k'). The compound of formula XLVI is the compound of formula I where m is 1, n is 0, $R^6$ is O, $R^{12}$ is absent and $R^7$ is alkyl having 1 to 3 carbon atoms. The compound of formula XLVI can be converted to the compound of formula XLVII via reaction step (l') in the same manner as described hereinbefore in connection with the reaction of step (f). The compound of XLVII is the compound of formula I where m is 1, n is 0 and $R^7$ is H. The conventional techniques such as extraction, evaporation, chromatography and recrystallization can be utilized to purify the products.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 5

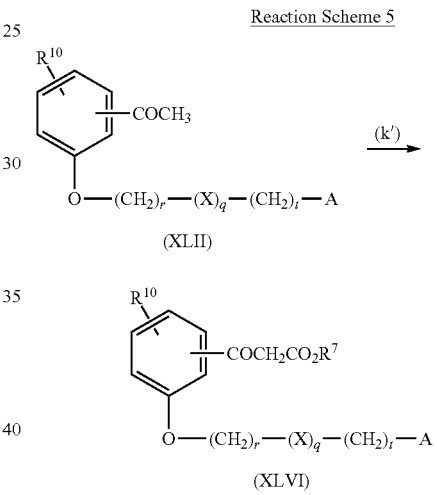

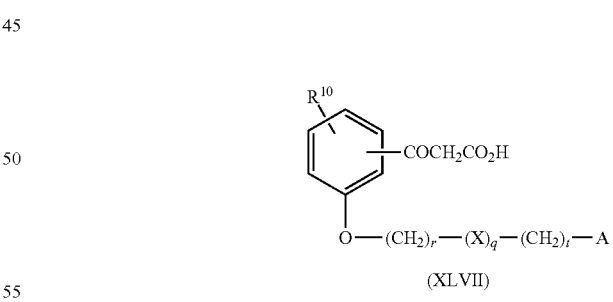

The compound of formula I where m is 2 to 4, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is O and $R^{12}$ is absent, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is $NH(R^{11})$ wherein $R^{11}$ is hydrogen or alkyl having 1 to 3 carbon atoms, i.e. compounds of formula:

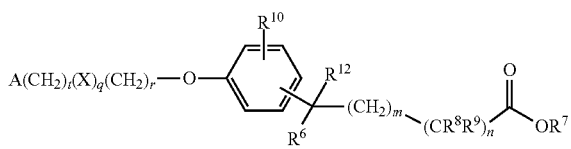

wherein A is described as above, can be prepared via reaction scheme of Scheme 6.

In the reaction scheme of Scheme 6, A, t, r, q, $R^7$ and $R^{10}$ are as above. $R^{16}$ is alkyl group having 1 to 2 carbon atoms or benzyl group and p is 1 to 3. The compound of formula XLII (prepared in the same manner as described in the reaction of scheme 4) can be converted to the compound of formula XLIX via the reaction of step (m') by alkylating the compound of formula XLII with the compound of formula XLVIII. This reaction can be carried out in the presence of approximately a molar equivalent of a conventional base that converts acetophenone to 3-keto ester (i.e. gamma-keto ester). In carrying out this reaction it is generally preferred but not limited to utilize alkali metal salts of hexamethyldisilane such as lithium bis-(trimethylsilyl) amide and the like. Generally this reaction is carried out in inert solvents such as tetrahydrofuran: 1,3-Dimethyl-3,4,5,6-tetrahydro-2 (1H)-pyrimidinone. Generally the reaction is carried out at temperatures of from −65° C. to 25° C. Any of the conditions conventional in such alkylation reactions can be utilized to carry out the reaction of step (m').

The compound of formula XLIX can be converted to the compound of formula L via reaction of step (n') where X is $NH(R^{11})$ wherein $R^{11}$ is hydrogen or alkyl having 1 to 3 carbon atoms and $R^7$ is H by ester hydrolysis or compound of formula L where X is C(O) and r is 0 and t is 0 and $R^7$ is H by catalytic hydrogenation. Any conventional methods of ester hydrolysis and catalytic hydrogenation to remove benzyl group can be utilized to produce the compound of formula L. The compound of formula L is the compound of formula I where m is 2 to 4, n is 0, $R^6$ is O, $R^{12}$ is absent and $R^7$ is H.

The compound of formula L can be converted to the compound of formula LI via reaction of step (o') where $R^7$ is alkyl having 1 to 3 carbon atoms in the same manner as described in the reaction of step (c). The compound of formula LI is the compound of formula I where m is 2 to 4, n is 0 and $R^7$ is alkyl having 1 to 3 carbon atoms.

The conventional techniques such as extraction, evaporation, chromatography and recrystallization can be utilized to purify the products.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 6

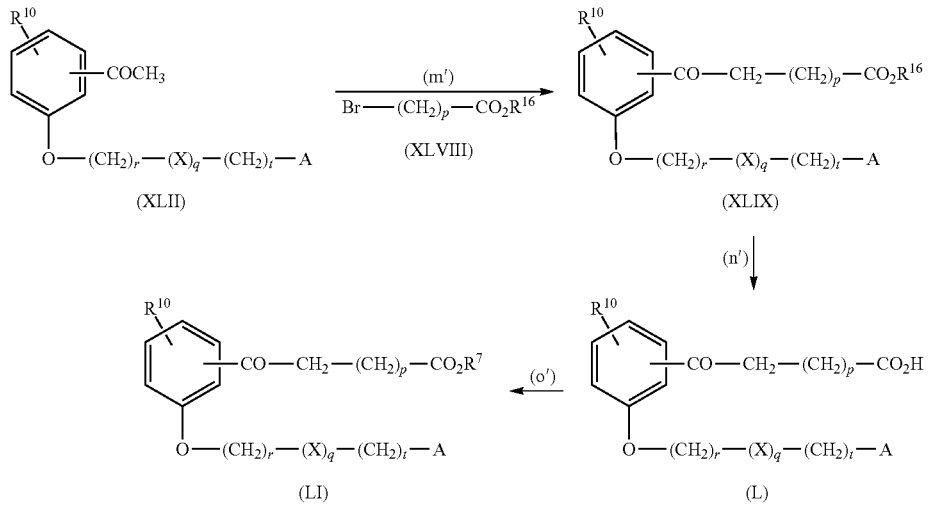

The compound of formula I where m is 0 to 3, q is 0 or 1, t is 0 or 1, and r is 0, 1 or 2, n is 1, $R^{10}$ is hydrogen, halo, alkoxy having from 1 to 3 carbon atoms or alkyl having from 1 to 3 carbon atoms, $R^6$ is O and $R^{12}$ is absent, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is $NH(R^{11})$ wherein $R^{11}$ is hydrogen or alkyl having 1 to 3 carbon atoms, i.e. compounds of formula:

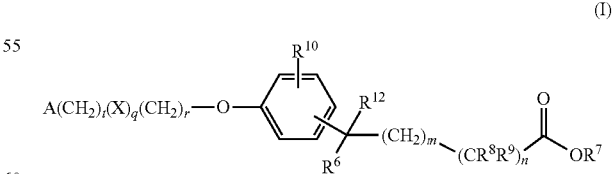

wherein A is described as above, can be prepared via reaction scheme of Scheme 7.

In the reaction scheme of Scheme 7, A, t, r, m, n, q, $R^7$, $R^8$, $R^9$ and $R^{10}$ are as above and u is 1 to 4. $R^{16}$ is alkyl group having 1 to 3 carbon atoms or benzyl group. $R^{13}$ is alkyl group having 1 to 3 carbon atoms, and Y is a halide.

The compound of formula LII can be converted to the compound of formula LIII in the same manner as described hereinbefore in the reaction of (c'). The compound of LIII is the compound of formula I where m is 0 to 3, n is 1 and $R^7$ is alkyl group having 1 to 3 carbon atoms. The compound of formula LIII can be converted to the compound of formula LIV via reaction of step (q') where X is $NH(R^{11})$ wherein $R^{11}$ is hydrogen or alkyl having 1 to 3 carbon atoms and $R^7$ is H by ester hydrolysis or compound of formula LIV where X is C(O) and r is 0 and t is 0 and $R^7$ is H by catalytic hydrogenation. Any conventional methods of ester hydrolysis and catalytic hydrogenation can be utilized to produce the compound of formula LIV.

The compound of formula LIV is the compound of formula I where m is 0 to 3, n is 1, $R^6$ is O, $R^{12}$ is absent and $R^7$ is H. The conventional techniques such as extraction, evaporation, chromatography and recrystallization can be utilized to purify the products.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 7

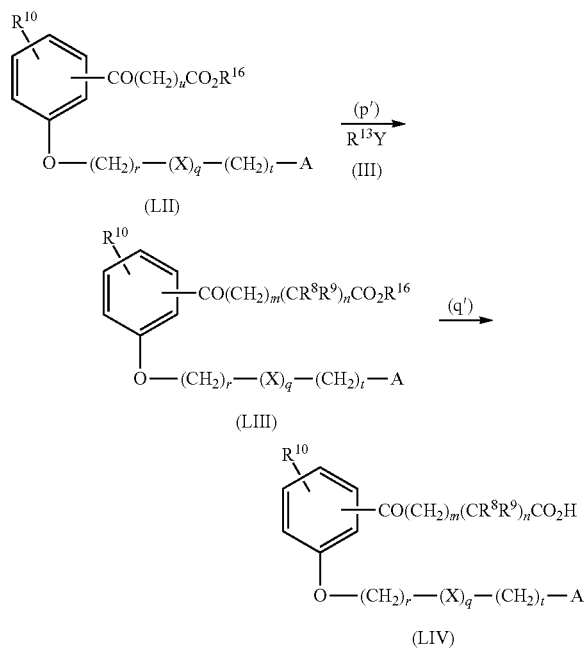

The compound of formula I where m is 0, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is hydroxy and $R^{12}$ is hydrogen, $R^7$ is hydrogen or alkyl having from 1 to 3 carbon atoms, and one of $R^8$ and $R^9$ is alkyl having from 1 to 3 carbon atoms, and the other is hydrogen or alkyl having 1 to 3 carbon atoms, and X is C(O), r is 0 and t is 0; X is $NH(R^{11})$ wherein $R^{11}$ is hydrogen or alkyl having 1 to 3 carbon atoms, i.e. compounds of formula:

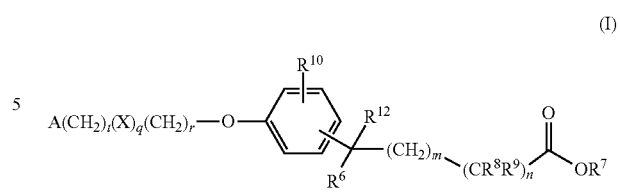

(I)

wherein A is described as above, can be prepared via reaction scheme of Scheme 8. In the reaction of Scheme 8, A, t, r, q, $R^6$, $R^7$, and $R^{10}$ are as above.

The compound of formula XLV (prepared in the same manner as described in the reaction of scheme 4) can be converted to the compound of formula LV via reaction of step (r') by hydrogenation of alpha-keto acid using catalyst for example rhodium-{amidophosphine-phosphinite} (Tetrahedron: Asymmetry, Vol 8, No. 7, 1083-1099, 1997), $[Ru_2Cl_4(BINAP)_2](NEt_3)$ (EP-A-0 295 890) and the like. Any conditions conventional in such hydrogenations can be utilized to carry out the reaction of step (r'). Using HPLC can separate racemic mixtures of formula LV. (Chirality 11:420-425 (1999). The compound of formula LV is the compound of formula I where m is 0, n is 0, $R^6$ is hydroxyl, $R^{12}$ is hydrogen and $R^7$ is alkyl group having 1 to 3 carbon atoms. The compound of formula LV can be converted to the compound of formula LVI where $R^7$ is H in the same manner as described in the reaction of step (f).

The compound of formula LVI is the compound of formula I where m is 0, n is 0 and $R^7$ is H. The product can be isolated and purified by techniques such as extraction, evaporation, chromatography, and recrystallization.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 8

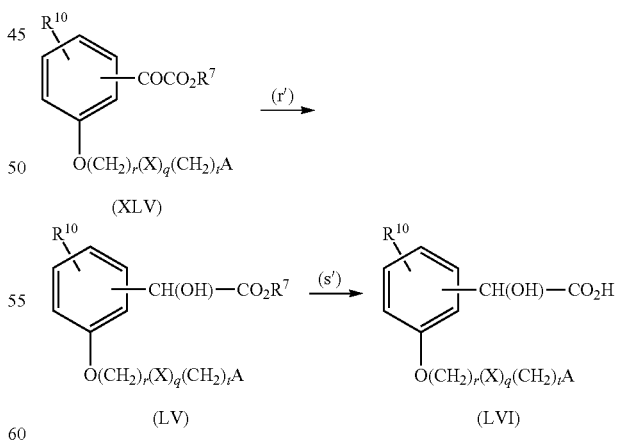

The compound of formula I where m is 1, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is hydroxy and $R^{12}$ is hydrogen, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is NH($R^{11}$) wherein $R^{11}$ is hydrogen or alkyl having 1 to 3 carbon atoms, i.e. compounds of formula:

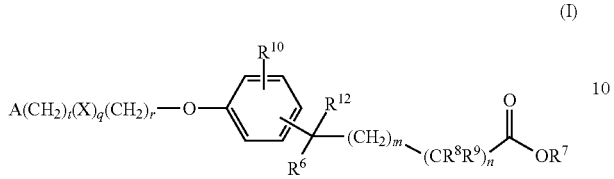

(I)

wherein A is described as above, can be prepared via reaction scheme of Scheme 9. In the reaction of Scheme 9, A, t, r, q, $R^7$, and $R^{10}$ are as above.

The compound of formula XLVI (prepared in the same manner as described in the reaction of scheme 5) can be converted the compound of formula LVII via reaction of step (t') by reducing the beta-keto group to an alcohol group. The reaction can be carried out by utilizing a conventional reducing agent that converts ketone to an alcohol for example, the reaction can be carried out by hydrogenation using a Raney nickel catalyst that had been treated with tartaric acid (Harada, T.; Izumi, Y. Chem Lett. 1978, 1195-1196) or hydrogenation with a chiral homogeneous ruthenium catalyst (Akutagawa, S.; Kitamura, M.; Kumobayashi, H.; Noyori, R.; Ohkuma, T.; Sayo, N.; Takaya, M. J. Am. Chem. Soc. 1987, 109, 5856-5858). The reduction can also be carried out by utilizing sodium borohydride in solvents such as methanol, ethanol and the like. Generally the reaction is carried out at temperatures from 0° C. to 25° C. Racemic mixtures of formula LVII can be separated by using HPLC. (Chirality 11:420-425 (1999).

The compound of formula LVII is the compound of formula I where m is 1, n is 0, $R^6$ is hydroxyl, $R^{12}$ is hydrogen and $R^7$ is alkyl having from 1 to 3 carbon atoms.

The compound of formula LVII can be converted to compound of formula LVIII via reaction of step (u') where $R^7$ is H in the same manner as described in the reaction of step (f). The compound of formula LVIII is the compound of formula I where m is 1, n is 0 and $R^7$ is H. The product can be isolated and purified by techniques such as extraction, evaporation, chromatography, and recrystallization.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 9

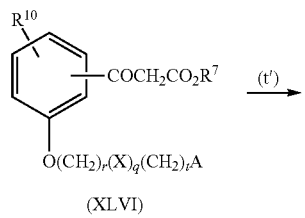

(XLVI)

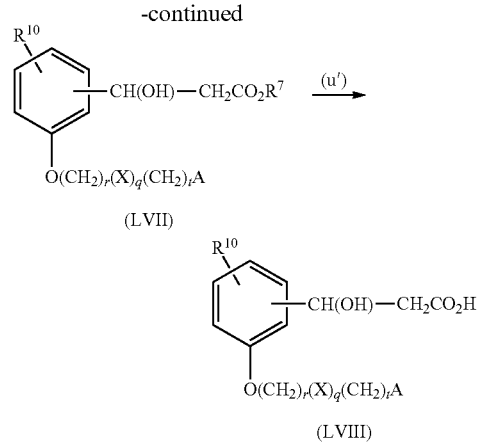

The compound of formula I where m is 2 to 4, q is 0 or 1, t is 0 or 1, and r is 0, 1 or 2, n is 0, $R^{10}$ is hydrogen, halo, alkoxy having from 1 to 3 carbon atoms or alkyl having from 1 to 3 carbon atoms, $R^6$ is hydroxy and $R^{12}$ is hydrogen, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is NH($R^{11}$) wherein $R^{11}$ is hydrogen or alkyl having 1 to 3 carbon atoms, i.e. compounds of formula:

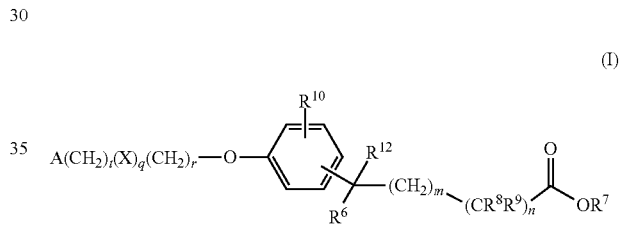

(I)

wherein A is described as above, can be prepared via reaction scheme of Scheme 10. In the reaction of Scheme 10, A, t, r, q, $R^7$, and $R^{10}$ are as above. $R^{16}$ is alkyl group having 1 to 3 carbon atoms or benzyl group and p is 1 to 3.

The compound of formula XLIX (prepared in the same manner as described in the reaction of scheme 6) can be converted to the compound of formula LIX via reaction of step (v') by reducing the ketone group to an alcohol group. The reaction can be carried out by utilizing a conventional reducing agent that converts ketone to alcohol. In carrying out this reaction it is generally preferred but not limited to utilize sodium borohydride as the reducing agent. Generally this reaction is carried out in solvents such as methanol, ethanol and the like. Generally the reaction is carried out at temperatures of from 0° C. to 25° C. The product can be isolated and purified by techniques such as extraction, evaporation, chromatography, and recrystallization.

Racemic mixtures of formula LIX can be separated by using HPLC. (Chirality 11:420-425 (1999). The compound of formula LIX is the compound of formula I where m is 2 to 4, n is 0, $R^6$ is hydroxy, $R^{12}$ is hydrogen and $R^7$ is an alkyl group having from 1 to 3 carbon atoms.

The compound of formula LIX can be converted to the compound of formula LX where $R^7$ is H by ester hydrolysis or catalytic hydrogenation via reaction of step (w') in the same manner as described hereinbefore in connection with the reaction of step (f). Any conventional methods of ester hydrolysis or catalytic hydrogenation will produce the compound of formula I where $R^1$ is H. The product can be isolated and purified by techniques such as extraction, evaporation, chromatography, and recrystallization.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 10

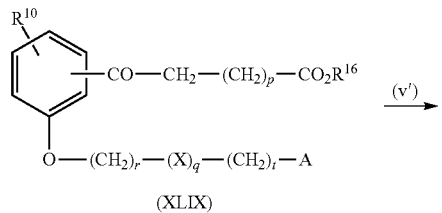

(XLIX)

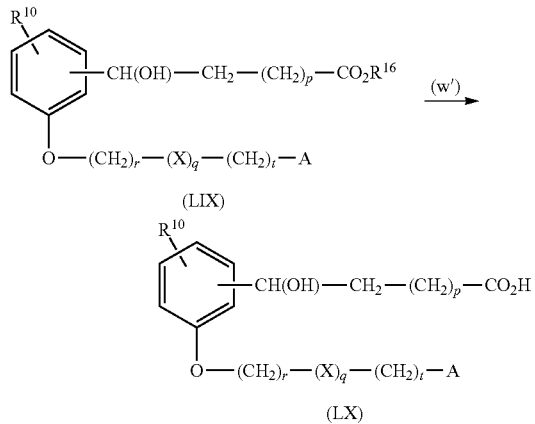

The compound of formula I where m is 0 to 3, q is 0 or 1, t is 0 or 1, and r is 0, 1 or 2, n is 1, $R^{10}$ is hydrogen, halo, alkoxy having from 1 to 3 carbon atoms or alkyl having from 1 to 3 carbon atoms, $R^6$ is hydroxy and $R^{12}$ is hydrogen, $R^7$ is hydrogen or alkyl having from 1 to 3 carbon atoms, and one of $R^8$ and $R^9$ is alkyl having from 1 to 3 carbon atoms, and the other is hydrogen or alkyl having from 1 to 3 carbon atoms, and X is C(O), r is 0 and t is 0; X is $NH(R^{11})$ wherein $R^{11}$ is hydrogen or alkyl having 1 to 3 carbon atoms, i.e. compounds of formula:

(I)

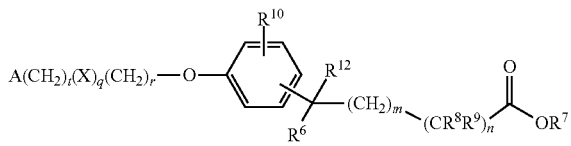

wherein A is described as above, can be prepared via reaction scheme of Scheme 11.

In the reaction of Scheme 11, A, t, r, q, $R^7$, $R^8$, $R^9$ and $R^{10}$ are as above.

The compound of formula LIII (prepared in the same manner as described in the reaction of scheme 7) can be converted to the compound of formula LXI via reaction of step (x') in the same manner as described hereinbefore in the reaction of step (v').

Racemic mixtures of formula LXI can be separated by using HPLC. (Chirality 11:420-425 (1999). The compound of formula LXI is the compound of formula I where m is 0 to 3, n is 1, $R^6$ is hydroxyl, $R^{12}$ is H and $R^7$ is alkyl group having from 1 to 3 carbon atoms.

The compound of formula LXI can be converted to the compound of formula LXII where $R^7$ is H via reaction of step (y') in the same manner as described hereinbefore in the reaction of step (f'). The compound of formula LXII is the compound of formula I where m is 0 to 3, n is 1, $R^6$ is hydroxyl, $R^{12}$ is H and $R^7$ is H.

The product can be isolated and purified by techniques such as extraction, evaporation, chromatography, and recrystallization. If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 11

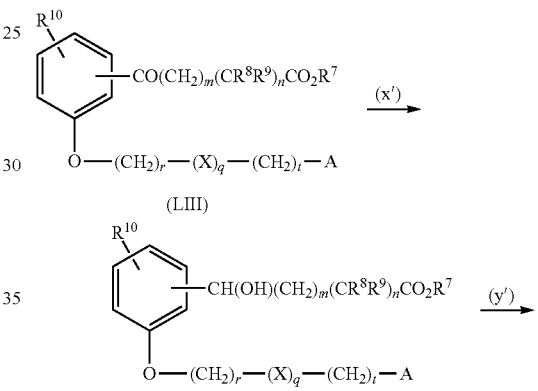

(LIII)

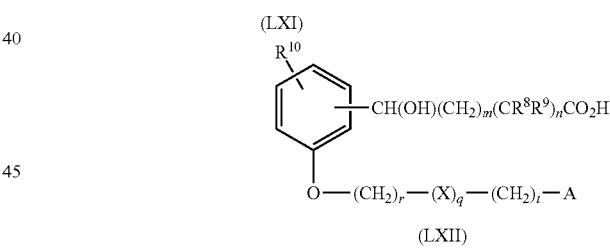

(LXI)

(LXII)

The compound of formula IX, where t is 0 or 1, r is 0, 1 or 2 and q is 0, i.e. compounds of formula:

A-$(CH_2)_t(X)_q(CH_2)_r$—OH  (IX)

and the compound of formula X, where t is 0 or 1, r is 0, 1 or 2 and q is 0, i.e. compounds of formula:

A-$(CH_2)_t(X)_q(CH_2)_r$—Y  (X)

can be prepared via reaction scheme of scheme 12.

In the reaction of Scheme 12, A is described as above. Y is a leaving group.

The compound of formula LXIII can be reduced to the compound of formula LXIV via reaction of step (z'). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (z'). The compound of formula LXIV is the compound of formula IX where t is 0 and r is 1.

The compound of formula LXIV can be converted to the compound of formula LXV by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (a").

The compound of formula LXV is the compound of formula X where t is 0 and r is 1.

The compound of formula LXV can be converted to the compound of formula LXVI by reacting LXV with an alkali metal cyanide for example sodium or potassium cyanide. The reaction is carried out in a suitable solvent, such as ethanol, dimethyl sulfoxide. Any of the conditions conventionally used in the preparation of nitrile can be utilized to carry out the reaction of step (b").

The compound of formula LXVI can be converted to the compound of formula LXVII via reaction step (c") by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (c").

The compound of formula LXVII can be reduced to give the compound of formula LXVIII via reaction of step (d"). This reaction can be carried out in the same manner as described hereinbefore in the reaction of step (z'). The compound of formula LXVIII is the compound of formula IX where t is 1 and r is 1.

The compound of formula LXVIII can be converted to the compound of formula LXIX via reaction of step (e") in the same manner as described hereinbefore in connection with the reaction of step (a"). The compound of formula LXIX is the compound of formula X where t is 1 and r is 1.

The compound of formula LXIX can be converted to the compound of formula LXX via reaction of step (f") in the same manner as described hereinbefore in connection with the reaction of step (b"). The compound of formula LXX can be hydrolyzed by acid or base to give the compound of formula LXXI via reaction of step (g").

The compound of formula LXXI can be converted to the compound of formula LXXII via reaction of step (h") in the same manner as described hereinbefore in connection with the reaction of step (z'). The compound of formula LXXII is the compound of formula IX where t is 1 and r is 2.

The compound of formula LXXII can be converted to the compound of formula LXXIII via reaction of step (i") in the same manner as described hereinbefore in connection with the reaction of step (a"). The compound of formula LXXIII is the compound of formula X where t is 1 and r is 2.

The product can be isolated and purified by techniques such as extraction, evaporation, chromatography, and recrystallization. If A is phenyl substituted by 1 or 2 hydroxyl groups, it is generally preferred to protect the hydroxyl groups. The suitable protecting group can be described in the Protective Groups in Organic Synthesis by T. Greene.

Reaction Scheme 12

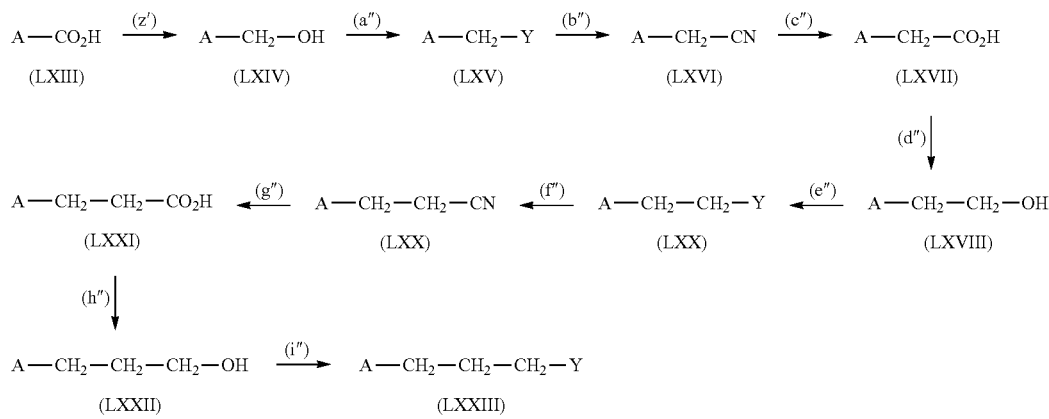

The compound of formula IX, where t is 0 or 1, r is 0, 1 or 2, q is 1 and X is $NH(R^{11})$ wherein $R^{11}$ is hydrogen or alkyl having 1 to 3 carbon atoms, i.e. compounds of formula:

$$A\text{-}(CH_2)_t(X)_q(CH_2)_r\text{---}OH \qquad (IX)$$

and the compound of formula X, where t is 0 or 1, r is 0, 1 or 2, q is 1 and X is $NH(R^{11})$ wherein $R^{11}$ is hydrogen or alkyl having 1 to 3 carbon atoms, i.e. compounds of formula:

$$A\text{-}(CH_2)_t(X)_q(CH_2)_r\text{---}Y \qquad (X)$$

can be prepared via reaction scheme of scheme 13.

In the reaction scheme of Scheme 13, A, t, r, and $R^{11}$ are as above. Y is chloro or bromo. The compound of formula LXXIV can be mesylated to furnish the compound of formula LXXV via the reaction of step (j"). Any conventional conditions to carry out the mesylation reaction of a hydroxyl group can be utilized to carry out the step (j"). The compound of formula LXXV is then heated with the compound of formula LXXVI to produce the compound of formula LXXVII. Any of the conditions conventional to produce amino alcohols can be utilized to carry out the reaction of step (k"). The compound of formula LXXVII is the compound of formula IX.

In the compound of formula LXXVII, alcohol can be displaced by chloro or bromo by treating the compound of formula LXXVII with thionyl chloride, bromine, phosphorus tribromide, oxalyl chloride, carbon tetrabromide and the like to produce the compound of formula LXXVIII. Any conventional method to displace alcohol with chloro or bromo can be utilized to carry out the reaction of step (l"). The compound of formula LXXVIII is the compound of formula X.

If A is phenyl substituted by 1 or 2 hydroxyl groups, it is generally preferred to protect the hydroxyl groups. The suitable protecting group can be described in the Protective Groups in Organic Synthesis by T. Greene. The protecting group can be deprotected utilizing suitable deprotecting reagents such as those described in Protective Groups in Organic Synthesis by T. Greene.

Reaction Scheme 13

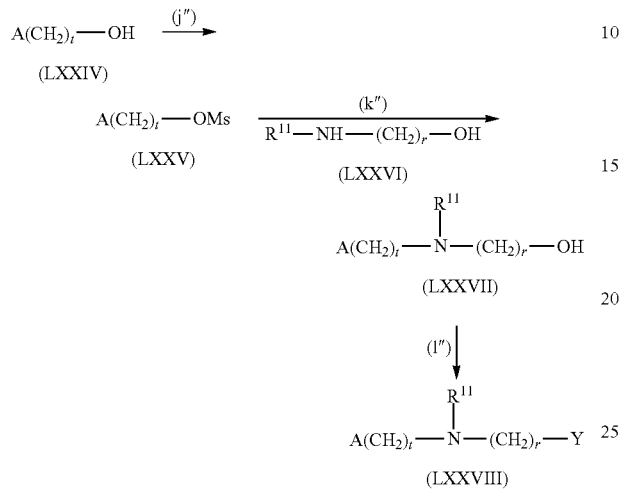

The compound of formula II where $R^{10}$ is hydrogen, halo, alkoxy having from 1 to 3 carbon atoms or alkyl having from 1 to 3 carbon atoms, i.e. compounds of formula:

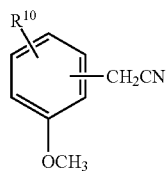

(II)

can be prepared via reaction scheme of scheme 14.

In the reaction scheme of Scheme 14, $R^{10}$ is as above. Y is a halide. The compound of formula LXXIX can be converted to the compound of formula LXXX via reaction of step (m") by alkylation of carboxylic acid and alcohol in the presence of base for example potassium carbonate by using methyl iodide in aprotic solvent for example N,N-dimethylformamide. Any conventional conditions of such alkylations can be utilized to carry out the reaction of step (m").

The compound of formula LXXX can be reduced to give the compound of formula LXXXI via reaction of step (n"). The reaction is carried out utilizing a conventional reducing agent for example alkali metal hydride such as lithium aluminum hydride. The reaction is carried out in a suitable solvent, such as tetrahydrofuran and the like. Any of the conditions conventional in such reduction reactions can be utilized to carry out the reaction of step (n").

The compound of formula LXXXI can be converted to the compound of formula LXXXII by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (o").

The compound of formula LXXXII can be converted to the compound of formula II by reacting LXXXII with alkali metal cyanide for example sodium, potassium, and copper cyanide. The reaction is carried out in a suitable solvent, such as ethanol, dimethyl sulfoxide. Any of the conditions conventionally used in the preparation of nitriles can be utilized to carry out the reaction of step (p").

Reaction Scheme 14

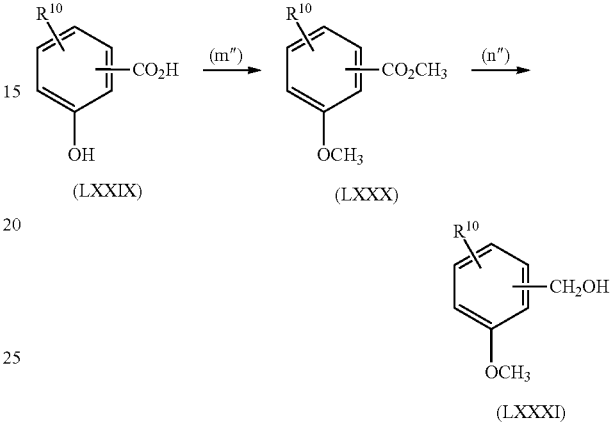

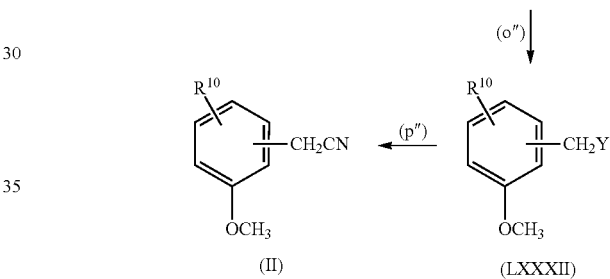

The compound of formula XXXIII where $R^{10}$ is hydrogen, halo, alkoxy having from 1 to 3 carbon atoms or alkyl having from 1 to 3 carbon atoms, i.e. compounds of formula:

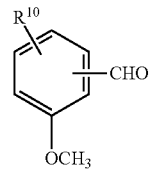

(XXXIII)

can be prepared via reaction scheme of scheme 15.

In the reaction scheme of Scheme 15, $R^{10}$ is as above. The compound of formula LXXXI can be converted to the compound of formula XXXIII via reaction of step (q") by oxidation of alcohol to the aldehyde. The reaction can be carried out utilizing a suitable oxidizing agent for example pyridinium chlorochromate, or dimethyl sulfoxide activated by 2,4,6-trichlorol-1,3,51-triazine (cyanuric chloride, TCT) under Swern oxidation conditions (J.O.C. 2001, 66, 7907-7909) and the like. Any of the conditions conventional in such oxidation reactions can be utilized to carry out the reaction of step (q").

Reaction Scheme 15

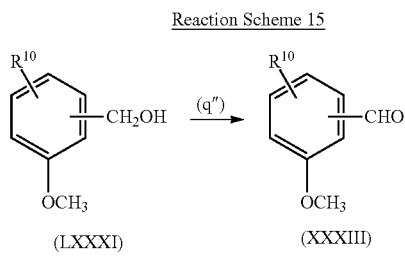

The compound of formula XXXIV where p is 2 to 4 and $R^{15}$ is alkyl group having 1 to 3 carbon atoms or benzyl group, i.e. compounds of formula:

can be prepared via reaction of scheme 16.

In the reaction scheme of Scheme 16, $R^{15}$ and p are as above. The compound of formula LXXXIII can be reacted with the compound of formula LXXXIV via the reaction of step (r″) to give compound of formula XXXIV. Any of the conditions conventionally used in reacting triphenylphosphine with hydrohalide can be utilized to carry out the reaction of step (r″).

Reaction Scheme 16

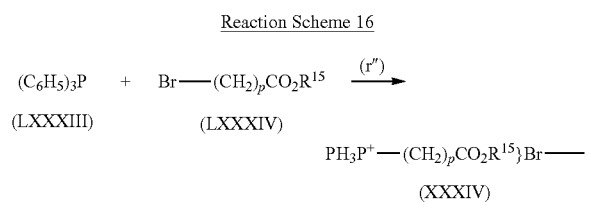

The compound of formula XLI where $R^{10}$ is hydrogen, halo, alkoxy having from 1 to 3 carbon atoms or alkyl having from 1 to 3 carbon atoms, i.e. compounds of formula:

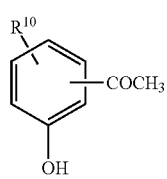

can be prepared via reaction scheme of scheme 17.

In the reaction scheme of Scheme 17, $R^{10}$ is as above. The compound of formula XLI can be synthesized according to the method of George M Rubottom et al., J. Org. Chem. 1983, 48, 1550-1552.

Reaction Scheme 17

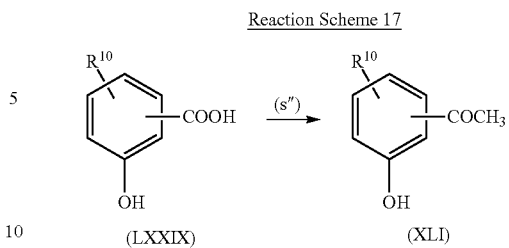

The compound of formula LXXIX where $R^{10}$ is halo, i.e. compounds of formula:

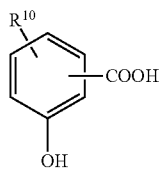

are either commercially available or can be prepared according to the methods described in the literature as follows:
1. 3-Br or F-2-OHC$_6$H$_3$CO$_2$H
  Canadian Journal of Chemistry (2001), 79(11) 1541-1545.
2. 4-Br-2-OHC$_6$H$_3$CO$_2$H
  WO 9916747 or JP 04154773.
3. 2-Br-6-OHC$_6$H$_3$CO$_2$H
  JP 47039101.
4. 2-Br-3-OHC$_6$H$_3$CO$_2$H
  WO 9628423.
5. 4-Br-3-OHC$_6$H$_3$CO$_2$H
  WO 2001002388.
6. 3-Br-5-OHC$_6$H$_3$CO$_2$H
  Journal of labelled Compounds and Radiopharmaceuticals (1992), 31 (3), 175-82.
7. 2-Br-5-OHC$_6$H$_3$CO$_2$H and 3-Cl-4-OHC$_6$H$_3$CO$_2$H
  WO 9405153 and U.S. Pat. No. 5,519,133.
8. 2-Br-4-OHC$_6$H$_3$CO$_2$H and 3-Br-4-OHC$_6$H$_3$CO$_2$H
  WO 20022018323
9. 2-Cl-6-OHC$_6$H$_3$CO$_2$H
  JP 06293700
10. 2-Cl-3-OHC$_6$H$_3$CO$_2$H
  Proceedings of the Indiana Academy of Science (1983), Volume date 1982, 92, 145-51.
11. 3-Cl-5-OHC$_6$H$_3$CO$_2$H
  WO 2002000633 and WO 2002044145.
12. 2-Cl-5-OHC$_6$H$_3$CO$_2$H
  WO 9745400.
13. 5-I-2-OHC$_6$H$_3$CO$_2$H and 3-I, 2-OHC$_6$H$_3$CO$_2$H
  Z. Chem. (1976), 16(8), 319-320.
14. 4-I-2-OHC$_6$H$_3$CO$_2$H
  Journal of Chemical Research, Synopses (1994), (11), 405.
15. 6-I-2-OHC$_6$H$_3$CO$_2$H
  U.S. Pat. No. 4,932,999.
16. 2-I-3-OHC$_6$H$_3$CO$_2$H and 4-I-3-OHC$_6$H$_3$CO$_2$H
  WO 9912928.
17. 5-I-3-OHC$_6$H$_3$CO$_2$H
  J. Med. Chem. (1973), 16(6), 684-7.
18. 2-I-4-OHC$_6$H$_3$CO$_2$H
  Collection of Czechoslovak Chemical Communications, (1991), 56(2), 459-77.
19. 3-I-4-OHC$_6$H$_3$CO$_2$,
  J.O.C. (1990), 55(18), 5287-91.

The compound of formula LXXIX, where $R^{10}$ is alkoxy having from 1 to 3 carbon atoms, i.e. compounds of formula:

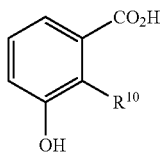
(LXXIX)

can be synthesized via the reaction of scheme 18.

In the reaction of scheme 18, $R^{15}$ is alkyl group having from 1 to 2 carbon atoms. P is a hydroxyl protecting group. The compound of formula LXXXV can be converted to the compound of formula LXXXVI via reaction of step (t") by protecting phenol group by suitable protecting group. The suitable conditions for the protecting group can be described in the Protective Groups in Organic Synthesis by T. Greene.

The compound of formula LXXXVI can be converted to the compound of formula LXXXVII by oxidation of aldehyde to carboxylic acid. The reaction can be carried out by using suitable oxidizing reagents for example, pyridinium chlorochromate, potassium permanganate, sodium permanganate and the like. Any of the conditions suitable in such oxidation reactions can be utilized to carry out the reaction of step (u").

The compound of formula LXXXVII can be converted to the compound of formula LXXIX via reaction of step (v") where $R^{10}$ is alkoxy having 1 carbon atom by deprotection of protecting group. The suitable deprotecting conditions can be described in the Protective Groups in Organic Synthesis by T Greene.

The compound of formula LXXXVII can be converted to the compound of formula LXXXVIII by treating the compound of formula LXXXVII with boron tribromide or boron trichloride using solvent for example dichloromethane for 4 to 48 hours at the temperature from −72° C. to 0° C. Any of the conditions conventional in such reactions can be utilized to carry out the reaction of step (w").

The compound of formula LXXXVIII can be converted to the compound of formula LXXXIX by esterification of compound of formula LXXXVIII with methanol or ethanol. The reaction can be carried out either by using catalysts for example $H_2SO_4$, TsOH and the like or by using dehydrating agent for example dicyclohexylcarbodiimide and the like. Any of the conditions conventional in such esterification reactions can be utilized to carry out the reaction of step (x").

The compound of formula LXXXIX can be converted to the compound of formula LXXXX by etherifying or alkylating the compound of formula LXXXIX with alkyl halide having 2 to 3 carbon atoms by using suitable base for example potassium carbonate, sodium hydride, pyridine and the like. The reaction can be carried out in conventional solvents, such as terahydrofuran, N,N-dimethylformamide, dichloromethane and the like. The reaction is generally carried out at temperatures from 0° C. to 40° C. Any of the conditions suitable in such alkylation reactions can be utilized to carry out the reaction of step (y").

The compound of formula LXXXX can be converted to the compound of formula LXXIX via reaction of step (z") where $R^{10}$ is alkoxy having 2 to 3 carbon atoms by deprotection of protecting group. The suitable deprotecting conditions can be described in the Protective Groups in Organic Synthesis by T Greene.

The product can be isolated and purified by techniques such as extraction, evaporation, chromatography, and recrystallization.

Reaction Scheme 18

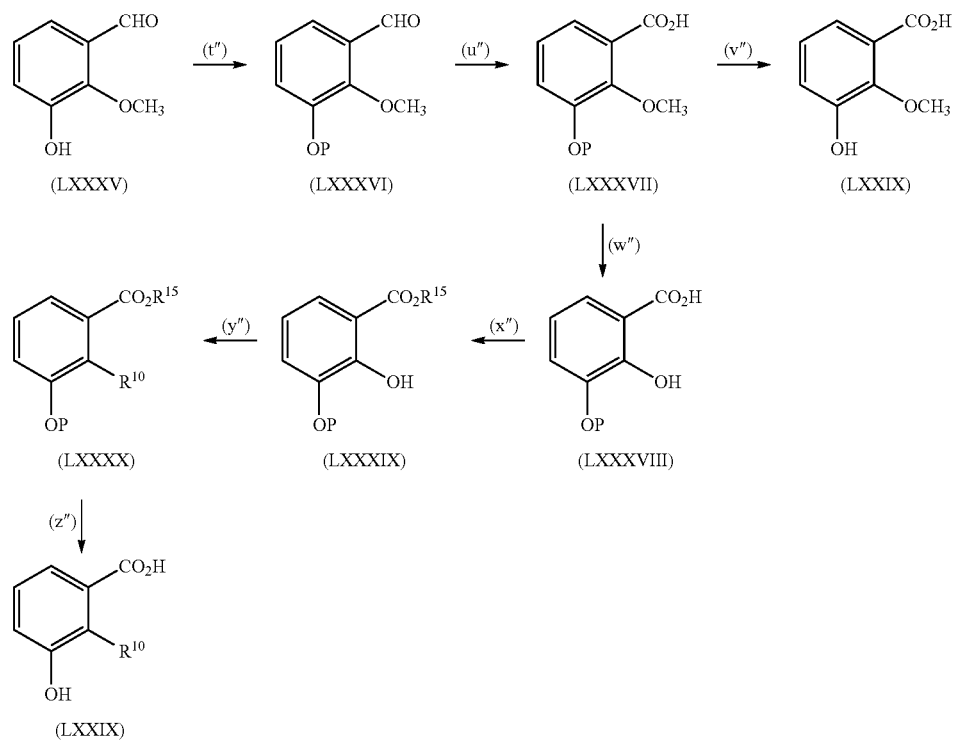

The compound of formula LXXIX, where $R^{10}$ is alkoxy having from 1 to 3 carbon atoms, i.e. compounds of formula:

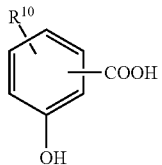

(LXXIX)

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24, 221-8.
JP 07070025.
7. 3-OEt-4-OHC$_6$H$_3$CO$_2$H
WO 9626176.
8. 3-OPr-2-OHC$_6$H$_3$CO$_2$H
JP 07206658, DE 2749518.
9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4-OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24, 221-8 by using propyl halide.
13. 4-OEt-3-OHC$_6$H$_3$CO$_2$H
Biomedical Mass Spectrometry (1985), 12(4), 163-9.
14. 3-OPr-5-OHC$_6$H$_3$CO$_2$H
Adapt synthesis from Taiwan Kexue (1996), 49(1), 51-56 by using propyl halide.

The compound of formula LXXIX, where $R^{10}$ is an alkyl having from 1 to 3 carbon atoms, i.e. compounds of formula:

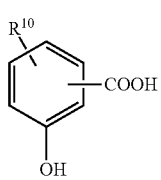

(LXXIX)

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem (1981), 24(10), 1245-49.
13. 2-n-Pr-3-OHC$_6$H$_3$CO$_2$H
WO 9509843 and WO 9628423.
14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.
16. 3-n-Pr-4-OHC$_6$H$_3$CO$_2$H
Polymer (1991), 32(11) 2096-105.
17. 2-n-Pr-4-OHC$_6$H$_3$CO$_2$H
3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
Adapt synthesis from J.O.C. 2001, 66, 7883-88 by using 2-Ethylacrolein and 2-Propylacrolein.

Use in Methods of Treatment

This invention provides a method for reducing uric acid levels in a mammalian subject or increasing uric acid excretion from a mammalian subject. The level of uric acid in a mammal can be determined using any conventional measure. Typically the level of uric acid in the blood is determined. Uric acid can also be deposited or precipitated in tissues, resulting in depots (e.g. tophi) that can be affected by raising or lowering blood uric acid concentrations, and which conversely can contribute to circulating uric acid. The method of this invention for reducing uric acid can be used to treat or prevent a variety of conditions including gout, hyperuricemia, elevated levels of uric acid that do not meet the levels customarily justifying a diagnosis of hyperuricemia, kidney stones, renal dysfunction, cardiovascular disease, cardiovascular risk factor, and cognitive impairment. By lowering uric acid levels, administration of the compounds of Formula I slows progression of kidney disease. An elevated uric acid level has been identified as a risk factor for cardiovascular disease. A significant correlation has been shown between elevated uric acid and cognitive impairment in older adults. (Schretlen, D. J. et al., "Serum Uric Acid and Cognitive Function in Community-Dwelling Older Adults", Neuropsychology (January 2007) 21(1): 136-140). Accordingly, the method of this invention for reducing uric acid can be used to treat or prevent cognitive impairment, including cognitive impairment in elderly adults. It is well known that people with Lesch-Nyhan Syndrome have elevated levels of uric acid and suffer the numerous consequences of this hyperuricemia, including gout. Thus, this invention for reducing blood levels and increasing elimination of uric acid can be used to treat people with Lesch-Nyhan Syndrome.

The normal range of uric acid in blood is between 3.4 mg/dL and 7.0 mg/dL in men, between 2.4 mg/dL and 6.0 mg/dL in premenopausal women, and from 2.5 mg/dL to 5.5 mg/dL in children. Urate crystal formation/precipitation typically occurs in men at levels of 6.6 mg/dL or higher and in women at levels of 6.0 mg/dL or higher. This illustrates that levels of uric acid that are within the so-called normal range can have undesirable health consequences, even producing gout. Also, what may be in the normal range for the population as a whole may be elevated for the individual. Cardiovascular and other consequences of elevated uric acid can occur with blood levels well within these "normal" ranges. Therefore, a diagnosis of hyperuricemia is not necessarily a prerequisite for the beneficial effects of the compounds of the invention.

This invention includes the treatment of hyperuricemia associated with gout, hypertension, vascular inflammation, heart failure, arterio-venous disorders, myocardial infarct, stroke, pre-eclampsia, eclampsia, sleep apnea, renal dysfunction (including renal failure, end stage renal disease [ESRD]), organ transplant, diuretics, thiazides, cyclosporine, aspirin, vitamin C, nicotinic acid, levodopa (L-DOPA), cytotosic drugs, and certain antibacterial agents (such as pyrozinamide), cirrhosis, thyroid dysfunction, parathyroid dysfunction, lung cancer, anemia, leukemia, lymphoma, multiple myeloma, tumor-lysis syndrome, thyroid or parathyroid dysfunction, Lesch-Nyhan Syndrome, smoking, alcohol consumption, and psoriasis. This invention includes the treatment of hyperuricemia that can lead to gout, formation of urate crystals, renal dysfunction, graft or organ failure following transplant, endothelial disorders (such as inflammation), chronic heart failure, arterio-venous disorders, pre-eclampsia, eclampsia, hypertension, and cognitive impairment. In embodiments of the method of this invention for treating gout, tissue deposits of uric acid, including but not limited to tophi, are reduced, and the incidence and severity of gout flares are also reduced.

The Compound of Formula I or salt thereof can be administered by any conventional route of systemic administration. Preferably they are administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any of the embodiments of the Compound of Formula I or pharmaceutically salts thereof. In the interest of avoiding unnecessary redundancy, each such agent and group of agents is not being repeated, but they are incorporated into this description of uses and methods of treatment as if they were repeated.

Both human and non-human mammalian subjects can be treated in accordance with the treatment method of this invention. The optimal dose of a particular active agent of the invention for a particular subject can be determined in the clinical setting by a skilled clinician. In the case of oral administration the Compound of Formula I or pharmaceutically acceptable salt thereof is generally administered to adults in a daily dose of from 1 mg to 2500 mg, more preferably from 1 mg to 1200 mg, more preferably from 400 mg to 1000 mg, more preferably from 600 mg to 800 mg, more preferably from 600 mg to 1000 mg, administered once or twice per day. The average body weight of a typical adult is 60 to 70 kilograms, so that appropriate dose ranges expressed as mg/kg are approximately from 0.015 to 42 mg/kg, more preferably from 0.015 to 20 mg/kg, more preferably from 6.6 to 13 mg/kg, more preferably from 10 to 13 mg/kg mg, more preferably from 10 to 16 mg/kg, administered once or twice per day. When treating children the optimal dose is determined by the patient's physician. In the case of oral administration to a mouse the Compound of Formula I or pharmaceutically acceptable salt thereof is generally administered in a daily dose from 1 to 300 mg of the agent per kilogram of body weight. In view of the potency of Compound EH (See Example 6, Table 6), the dosage ranges listed above should be decreased by a factor of about 10.

The Compound of Formula I or pharmaceutically acceptable salt thereof can be administered in combination with other uric acid lowering drugs. In such cases the dose of the Compound of Formula I or its salts is as described above. Any conventional or investigational uric acid lowering drug can be utilized in combination with the compounds of Formula I. Examples of such drugs include xanthine oxidase inhibitors such as allopurinol (from 100 mg/day to 1000 mg/day; more typically from 100 mg/day to 300 mg/day) febuxostat (from 40 mg/day to 120 mg/day; more specifically from 60 mg/day to 80 mg/day) and oxypurinol; Puricase/PEG-uricase (from 4 mg to 12 mg every two weeks by infusion); uricosuric agents such as sulfinpyrazone (from 100 mg/day to 800 mg/day), probenecid (500 mg/day), losartan (from 25 mg/day to 200 mg/day, more typically from 50 mg/day to 100 mg/day), fenofibrate, JTT-552 (a URAT-1 inhibitor), benzbromarone (from 70 mg/day to 150 mg/day), and statins such as atorvastatin (LIPITOR®). The other uric acid lowering drug can be administered in its usual amount or in an amount that is less than the usual amount, whether by administering lower doses of such other drug or by less frequent dosing with such other drug.

The compounds of Formula I and their pharmaceutically acceptable salts can be administered together with other drugs used to decrease the pain associated with gouty attacks, for example nonsteroidal antiinflammatory drugs (NSAIDs), colchicine, corticosteroids, and other analgesics.

In the course of lowering uric acid levels in the blood it is expected that the compounds of Formula I will increase the levels of uric acid in the urine. To increase the pH of the urine and thereby improve solubility of the uric acid, citrate or bicarbonate, for example, can be administered in conjunction with the compound of Formula I.

An admixture of the compound or salt of Formula I with one or more other uric acid lowering drugs, analgesics, and pH increasing agents, can be administered to the subject. Alternatively the compound or salt of Formula I and the one or more other uric acid lowering drugs, analgesics, and pH increasing agents are not mixed together to form an admixture but are administered independently to the subject. When the active ingredients are not mixed together to form a single admixture or composition it is convenient to provide them in the form of a kit comprising one or more unit oral doses of a Compound of Formula I or a pharmaceutically acceptable salt thereof, one or more unit oral doses of one or more other uric acid lowering drugs, analgesics, and pH increasing agents, and instructions for administering the Compound of Formula I or pharmaceutically acceptable salt thereof in combination with the other active ingredients. Preferably the components of the kit are packaged together, such as in a box or a blister pack.

Pharmaceutical Compositions

This invention provides a pharmaceutical composition comprising a compound of Formula I or a pharmaceutically acceptable salt thereof, and optionally a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 2500 mg, more preferably from 1 mg to 1200 mg, preferably from 400 mg to 1000 mg, more preferably from 600 mg to 800 mg, more preferably from 600 mg to 1000 mg, of the compound of Formula I or its salt. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The active ingredients can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

The invention will be better understood by reference to the following examples, which illustrate but do not limit the invention described herein.

EXAMPLES

Example 1

Five groups of 4 healthy, normal men and women received a single, oral administration of escalating doses of Compound BI (n=3 per group) or placebo capsules (n=1 per group) in a randomized, double blind clinical study. Blood uric acid levels were measured before and 24 hours after administration of study treatment. Compound BI was administered at doses of 50, 100, 200, 400 or 800 mg.

Administration of a single dose of Compound BI resulted in a significant, dose-dependent reduction in uric acid levels. Uric acid levels were elevated in subjects receiving placebo. (Table 1)

TABLE 1

| Study Treatment | (N) | Mean Percent Change |
|---|---|---|
| Placebo | (5) | +8.4 |
| BI 50 | (3) | −8.8 |
| BI 100 | (3) | −13.4 |
| BI 200 | (3) | −18.9 |
| BI 400 | (3) | −35.0 |
| BI 800 | (3) | −32.7 |

Example 2

Two groups of 8 healthy normal men and women received oral administration of either 800 mg Compound BI once per day (n=6 per group) or 400 mg Compound BI twice per day (n=6 per group) or placebo capsules (n=2 per group) in a randomized, double blind clinical study. Blood uric acid levels were measured before administration of study treatment, 24 hours after the first administration of study treatment and after 7 consecutive days of study treatment administration.

Administration of a single dose of Compound BI resulted in a significant reduction in uric acid levels in both groups of patients receiving Compound BI (Table 2), as did daily administration for 7 days (Table 3). Uric acid levels in patients receiving placebo capsules were elevated compared to baseline 24 hours after the first administration and unchanged after receiving placebo daily for 7 days.

TABLE 2

Percent Change in Uric Acid Levels Following a Single Administration of Study Treatment

| Study Treatment | (N) | Mean Percent Change |
|---|---|---|
| Placebo | (4) | +4.9 |
| BI 400 bid. | (6) | −54.0 |
| BI 800 qd | (6) | −45.3 |

TABLE 3

Percent Change in Uric Acid Levels Following a Daily Administration of Study Treatment for Seven Days

| Study Treatment | (N) | Mean Percent Change |
|---|---|---|
| Placebo | (4) | +0.5 |
| BI 400 bid. | (6) | −56.7 |
| BI 800 qd | (6) | −53.2 |

Example 3

Compound BI Increases Uric Acid Excretion in Urine of Mice Treated with the Uricase Inhibitor Potassium Oxonate The model to induce hyperuricemia involves the use of the uricase (urate oxidase) inhibitor potassium oxonate that causes a delay in the degradation of uric acid to allantoin. Humans have little or no uricase activity, so inhibition of this enzyme with potassium oxonate makes mouse uric acid processing more similar to that of humans. Male 11-week old C57/B16 mice (Harlan, Frederick, Md.) were used in the studies (8 per experimental group). Mice were receiving standard rodent chow that was removed one hour before administration of potassium oxonate. Mice were given an intraperitoneal injection (i.p.) of potassium oxonate (300 mg/kg) that was suspended in 0.5% hydroxypropylmethylcellulose (HPMC). After 90 minutes, mice received treatments by oral administration of allopurinol (20 mg/kg; Sigma, Saint Louis, Mo.), benzbromarone (30 or 100 mg/kg; Sigma) or Compound BI (100 mg/kg) or vehicle (1% HPMC) and urine collection was started. Urine collection was performed at 1, 3 and 5 hours after drug treatments and uric acid was measured with a colorimetric assay (BioVision Research Products, Mountain View, Calif.).

In urine collected between 3 and 5 hours after drug administration, Compound BI induced a significant increase in excreted uric acid versus the Oxonate control group. Benzbromarone at both doses also induced an increase in uric acid concentration in urine, though to lesser degree than Compound BI. Allopurinol, which inhibits uric acid synthesis in the liver and other tissues, reduced the concentration of uric acid in urine. (Table 4 and FIG. 1).

TABLE 4

| Experimental Group | Urine Uric Acid (mg/dL) |
|---|---|
| Oxonate 300 mg/kg i.p. (Control) | 118 ± 7 |
| Oxonate i.p + Cpd BI 100 mg/kg p.o. | 293 ± 13 ** |
| Oxonate i.p. + Allopurinol 20 mg/kg p.o. | 79 ± 5 |
| Oxonate i.p + Benzbromarone 30 mg/kg p.o. | 185 ± 12 * |
| Oxonate i.p + Benzbromarone 100 mg/kg p.o. | 173 ± 8 * |

\* = Greater than Oxonate group, $P < .05$
\*\* = Greater than Oxonate, Benzbromarone or Allopurinol groups, $P < .05$ Example 4

Plasma samples taken immediately prior to and at 1, 2, 4, 6, 12 and 24 hours after a single, oral administration of a test compound to 4 healthy, normal men and women in each of three groups as described above in Example 1 were analyzed to determine uric acid levels. Compound BI (n=3 per group) or placebo capsules (n=1 per group) were administered in a randomized, double blind clinical study. Plasma samples taken at the time points indicated from patients receiving Compound BI at doses of 200, 400 or 800 mg were stored at −70° C. and analyzed at a later time.

Figure 2:
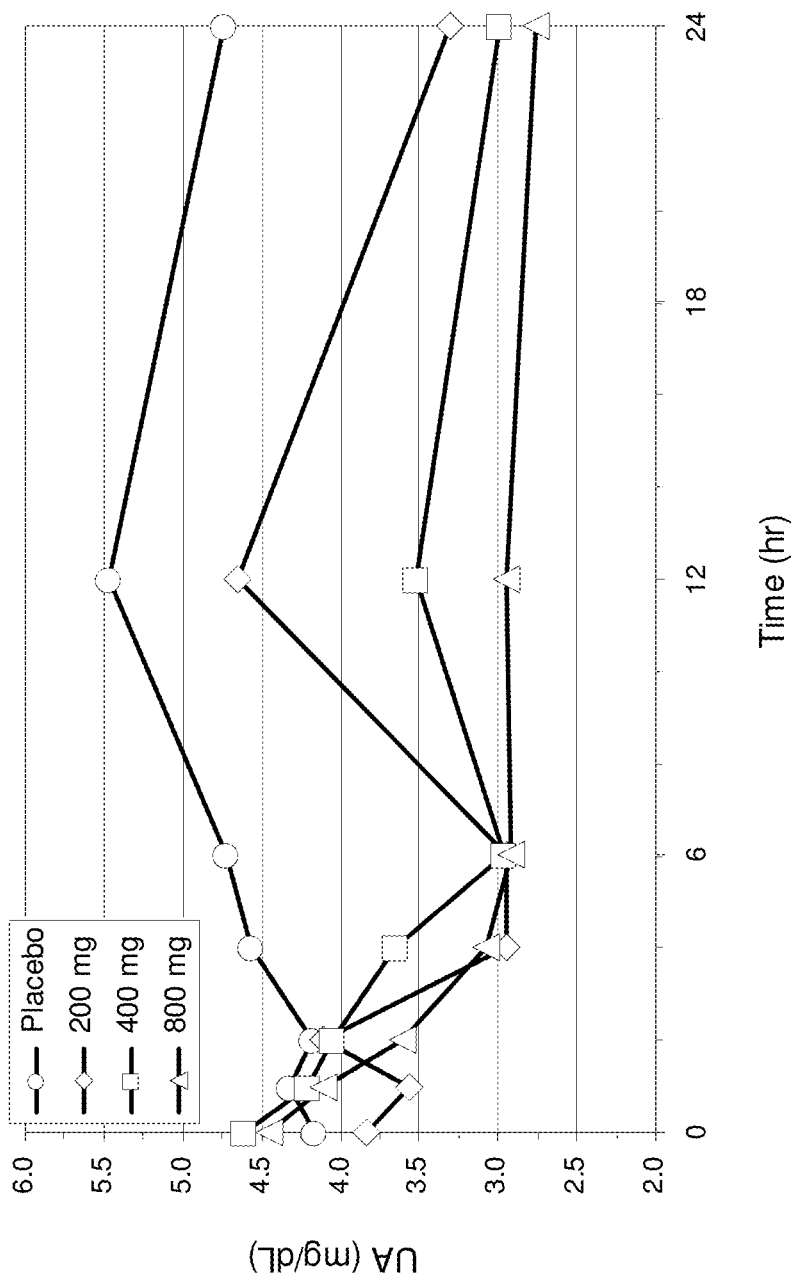
FIG. 2: Plasma UA (uric acid) levels over the initial 24-hour period in patients receiving various doses of Compound BI.

Administration of a single dose of Compound BI resulted in significant, dose-dependent reductions in uric acid levels in all three groups (FIG. 2). Uric acid levels were elevated compared to baseline values throughout the 24-hour period in subjects receiving placebo. Uric acid levels in the subjects receiving placebo steadily increased from baseline through 12 hours and then declined to near-baseline levels at 24 hours, reflecting a daily rhythm in serum uric acid levels. In contrast, uric acid levels in all subjects receiving Compound BI declined to or near to the lowest levels for each group through the 6-hour time point. Uric acid levels of the group receiving the highest dose of Compound BI were nearly identical at the 6 and 12-hour time points, and declined further between 12 and 24 hours.

These results indicate that administration of Compound BI can reduce the levels of uric acid throughout a 24-hour period compared to placebo administration and that administration of the highest single dose of Compound BI, 800 mg, resulted in the lowest levels of uric acid throughout the 24-hour period.

Example 5

Sixteen men and women participating in a clinical study were randomly assigned to receive either placebo capsules (n=4 subjects), 400 mg Compound BI twice per day (n=6 subjects), or 800 mg Compound BI once per day (n=6 subjects) for seven consecutive days. Plasma samples taken prior to (Time 0) and at 1, 2, 4, 9, 11, 13, 18 and 24 hours after the initial administration of the test article on Day 7 of the study were stored at −70° C. and later analyzed for uric acid. (This Example 5 is a continuation of the experiment described in Example 2.)

Uric acid levels in both groups of subjects receiving Compound BI were significantly reduced at Time 0 on Day 7 compared to Time 0 on the first day of the study and compared to placebo values throughout either day. Uric acid levels in the groups treated with Compound BI remained significantly below placebo values throughout Day 7 (FIG. 3).

Figure 3:
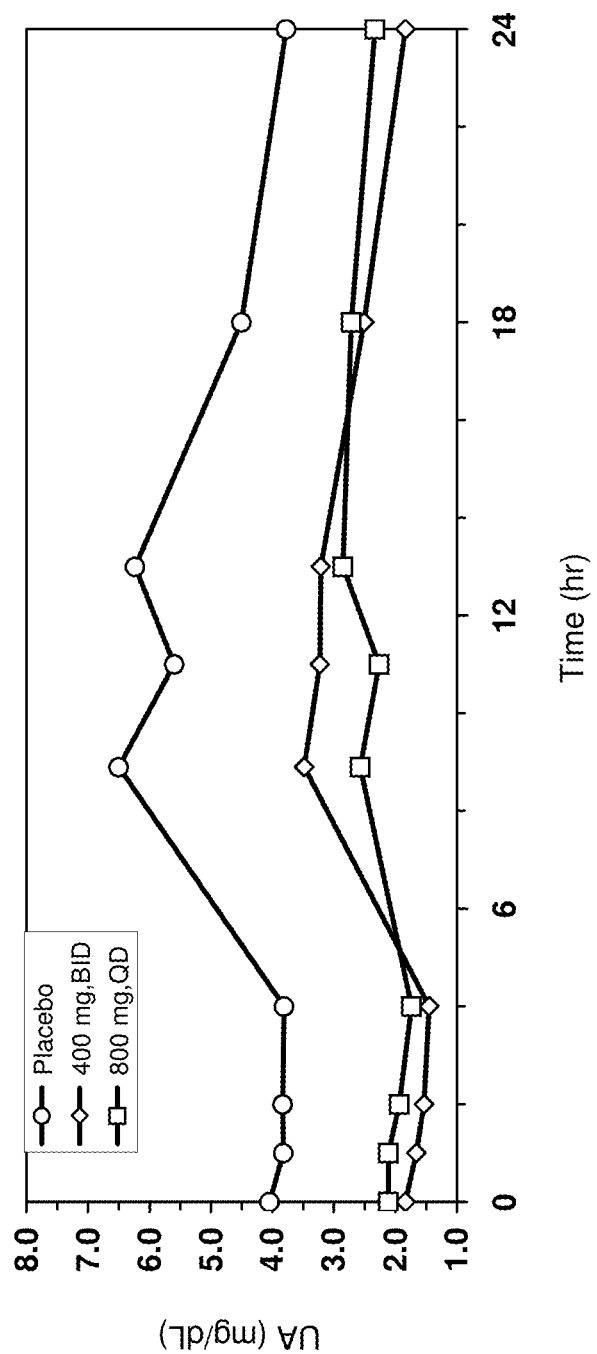
FIG. 3: Plasma UA (uric acid) levels over a 24-hour period on Day 7 of patients receiving various doses of Compound BI.

Uric acid levels throughout Day 7 in the subjects receiving placebo capsules daily over the 7-day course of the study were virtually unaffected by the placebo and were quite comparable to placebo values observed during the first 24-hour period of the study described in Example 4 as can be seen by comparing FIG. 3 with FIG. 2. (Example 4/FIG. 2 involved a different group of patients from Example 5/FIG. 3.)

These results show that daily administration of Compound BI for seven days reduced patient exposure to uric acid to an even greater extent than observed with a single day of treatment.

Example 6

URAT1 Inhibition Assay

URAT1 (Uric Acid Transporter 1) is expressed on the apical membrane in renal tubules. It mediates the re-uptake of uric acid from the urine into the blood Inhibition of URAT1 leads to increased excretion of uric acid in the urine, and is therefore a potential mode of action for drugs that lower serum uric acid concentrations. Probenecid and Benzbromarone, for example, have been used clinically for treatment of gout and hyperuricemia, and they both act on URAT1 to reduce uric acid reuptake. However, benzbromarone was withdrawn from the market due to liver toxicity via mechanisms independent of URAT1, and probenecid acts on numerous transporter proteins, resulting in interactions with a variety of other drugs.

An in vitro URAT1 assay is useful for identifying compounds with potential activity in lowering serum uric acid. A suitable assay involves transfection of cells (e.g. human embryonic kidney cells; "HEK") with a vector encoding human URAT1, followed by determination of the ability of transfected cells to take up radiolabeled uric acid. The activity of compounds as URAT1 inhibitors is evaluated by their ability to block uric acid uptake by transfected cells.

Test Compounds and Chemicals:

Benzbromarone (Sigma, Cat. No. B5774), Probenecid (Sigma, Cat. No. P8761)), DMSO (Sigma, Cat. No. D-2650), [8-$^{14}$C] Urate (50-60 mCi/mmol; American Radio Chemicals, Cat. No. ARC0513).

Subcloning of hURAT1 into the Expression Vector:

Plasmid vector pCMV6-XL5 containing hURAT1 cDNA (Cat. No. SC125624) and the expression vector pCMV6-Neo (Cat. No. pCMVNEO) were obtained from OriGene Technologies, Inc. The full-length hURAT1 cDNA was obtained from the vector pCMV6-XL5 and subcloned into the expression vector pCMV6-Neo to create the hURAT1 expression plasmid pCMV6-hURAT1. The sequences were verified by automatic DNA sequencing.

Cell Culture, Transfection of URAT1 Expressing Plasmids and the Establishment of Stably Expressing HEK Cells for hURAT1:

Human embryonic kidney 293 (HEK) cells (ATTCC, Cat No. CRL-1573) were cultured in EMEM supplemented with 10% FBS and 2 mM L-glutamine and incubated at 37° C. and 5% $CO_2$. For transfection experiments, cells were plated on 60 mm dishes in 1 ml media per dish. After an 18-24 hour incubation, cells were transfected with plasmid pCMV6-hURAT1 or the expression vector pCMV6-Neo, using the Lipofectin transfection agent following the manufacturer's instructions (Invitrogen, Cat. No. 18292). After transfection cells were grown in EMEM media for 72 hours and then by adding 1 mg/ml Geneticin (GIBCO, Cat. No 10131) stable transfectants were selected. Stable transfectants expressing hURAT1 (herein after referred as hURAT1-HEK cells) or cells having only the expression vector pCMV6-Neo (herein after referred as mock-HEK cells) were verified using reverse transcription polymerase chain reaction (RT-PCR) methods.

[8-$^{14}$C] Urate Uptake Assay:

hURAT1-HEK cells and mock-HEK cells were plated in poly-D-Lysine Cell culture 24 well plates (Becton Dickinson, Cat. No. 354414) at a concentration of $3\times10^5$ in EMEM medium and incubated overnight. Reaction solutions containing the [8-$^{14}$C] urate (55 mCi/mmol) at a final concentration of 50 μM were prepared with or without test compounds in Hanks' balanced salt solution (HBSS) containing 125 mM sodium gluconate, 4.8 mM potassium gluconate, 1.3 mM calcium, 5.6 mM glucose, 1.2 mM magnesium sulfate, 1.2 mM $KH_2PO_4$ and 25 mM HEPES (pH7.4). Before the uptake assay started, the culture medium was removed and the cells were incubated for 5 min in 0.6 ml of HBSS. After that HBSS was removed, the prepared reaction solutions were added into each well and incubated for 5 min at room temperature. Then the reaction solution was removed, cells were washed twice with 0.6 ml of cold HBSS and lysed with 0.2 ml of 0.1 M NaOH for 20 min. The cell lysates were transferred into the scintillation vials containing 1 ml of scintillation fluid (Opti Phase SuperMIX, PerkinElmer, Cat No. 1200-439) and the radioactivity was counted in the Microbeta counter (1450, Wallac Jet, PerkinElmer). Test compounds were dissolved in DMSO and the same concentration of DMSO was added into the wells of mock-HEK cells and the hURAT1-HEK cells that didn't contain test compounds. For each test compound, the uptake assay was performed 2 times and carried out in triplicate. Urate uptake of the cells for each test condition was presented as the average percent inhibition in comparison to the DMSO control. The radioactivity values obtained for the wells that contained DMSO were taken as 100% uptake of the cells. The observed concentration-percent inhibition data were fitted to a sigmoidal concentration-effect model, where:

$$IC50^\wedge Slope = [(100 * Conc^\wedge Slope)/\% \text{ Inhibition}] - Conc^\wedge Slope$$

$IC_{50}$ and slope estimates with their 95% confidence limits were determined by a non-linear, least-squares regression analysis using the Data Analysis Toolbox™ (MDL Information Systems, San Leandro, Calif., USA).

For assessment of activity of compounds as URAT1 inhibitors, the percent inhibition of uric acid uptake was typically assessed at a drug concentration of 10 micromolar (Table 5). Additional drug concentrations were tested for determination of IC-50 values for some compounds (Table 6).

TABLE 5

| Test Compound | % of Inhibition | S.D. |
|---|---|---|
| AB | 3.7 | 3.29 |
| AF | 41.30 | 7.97 |
| AG | 5.99 | 4.39 |
| AH | 26.78 | 2.97 |
| AI | 2.3 | 0.25 |
| AM | 0.0 | 0.0 |
| AN | 54.44 | 3.47 |
| AT | 7.95 | 2.60 |
| AW | 61.93 | 1.61 |
| AY | 8.9 | 2.14 |
| BH | 62.40 | 5.47 |
| BI | 86.07 | 0.46 |
| BJ | 81.76 | 1.41 |
| BM | 22.21 | 2.20 |
| BP | 76.50 | 4.63 |
| BS | 28.60 | 6.38 |
| BT | 51.80 | 2.55 |
| CF | 96.50 | 1.13 |
| EB | 21.57 | 0.48 |
| CD | 63.5 | 0.44 |
| CQ | 84.84 | 0.36 |
| DP | 60.51 | 1.24 |
| CK | 88.00 | 0.84 |
| CM | 88.96 | 1.18 |
| CR | 60.60 | 3.70 |
| DR | 68.30 | 0.47 |
| DS | 75.00 | 1.00 |
| DT | 89.12 | 0.48 |
| DU | 30.52 | 2.10 |
| DN | 45.38 | 0.79 |
| DV | 79.55 | 0.79 |
| DO | 80.30 | 0.29 |
| DQ | 99.40 | 1.01 |
| EA | 49.00 | 1.36 |
| DW | 54.00 | 4.34 |
| DX | 64.00 | 1.79 |
| DY | 85.20 | 1.73 |
| DZ | 26.90 | 6.22 |
| EC | 89.12 | 0.48 |
| ED | 79.55 | 0.79 |
| EE | 90.1 | 0.22 |
| EF | 90.35 | 0.09 |
| EG | 89.68 | 0.35 |
| EH | 95.86 | 0.11 |
| EI | 93 | 0.17 |

TABLE 6

| Compound | IC50 values (μM) |
|---|---|
| CQ | 1.33 |
| CM | 1.01 |
| CK | 2.69 |
| DT | 0.33 |
| DQ | 0.18 |
| DY | 1.88 |
| CF | 0.53 |
| BI | 0.95 |
| DV | 0.89 |
| BP | 4.39 |
| EC | 0.33 |
| ED | 0.89 |
| EF | 0.59 |
| EH | 0.08 |
| Benzbromarone | 0.75 |
| Probenecid | 174 |

Example 7

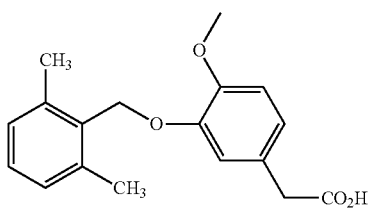 [SMILES: COc1ccc(CC(=O)O)cc1OCc1c(C)cccc1C]

2-(3-(2,6-Dimethylbenzyloxy)-4-methoxyphenyl)acetic acid

Step A: Preparation of Ethyl 2-(3-hydroxy-4-methoxyphenyl)acetate

The stirred solution of 2-(3-Hydroxy-4-methoxyphenyl)acetic acid (9.82 g, 53.90 mmol) and p-Toluenesulfonic acid monohydrate (1.15 g, 6.0 mmol) in abs ethanol (100 ml) was refluxed for 4 hours or until all the starting material is consumed. The reaction mixture was concentrated, diluted with ethyl acetate and washed with 1M HCl. The organic layer was dried over $Na_2SO_4$, filtered, concentrated, and purified by flash chromatography on a silica gel column (hex:ethyl acetate 2:1) to give the title compound.

$^1$H NMR (270 MHz, $CDCl_3$): 1.2 (t, 3H); 3.6 (s, 2H); 3.8 (s, 3H); 4.1 (q, 2H); 6.6-6.8 (m, 3H).

Step B: Preparation of Ethyl 2-(3-(2,6-dimethylbenzyloxy)-4-methoxyphenyl)acetate A solution of 2,6-Dimethylbenzyl alcohol (3.23 g, 23.7 mmol) and diisopropyl azodicarboxylate (DIAD, 5.23 g, 25.9 mmol) in THF (20 ml) was added drop wise to a solution of Ethyl 2-(3-Hydroxy-4-methoxyphenyl)acetate (Step A, 5.48 g, 26.12 mmol) and triphenylphosphine (6.79 g, 25.9 mmol) in THF (100 ml) at 0° C. The reaction mixture was stirred at room temperature for 4 hours, diluted with ether and washed with water and brine. The organic layer was dried over $Na_2SO_4$, filtered, concentrated, and purified by flash chromatography on a silica gel column (hex:ethyl acetate 4:1) to give the title compound.

$^1$H NMR (270 MHz, $CDCl_3$): 1.2 (t, 3H); 2.3 (s, 6H); 3.5 (s, 2H); 3.8 (s, 3H); 4.1 (q, 2H); 5.1 (s, 2H); 6.9 (m, 2H); 7.15-7.35 (m, 4H).

Step C: Preparation of 2-(3-(2,6-Dimethylbenzyloxy)-4-methoxyphenyl)acetic acid To a stirred solution of Ethyl 2-(3-(2,6-dimethylbenzyloxy)-4-methoxyphenyl)acetate (Step B, 7.86 g, 24 mmol) in absolute ethanol (120 ml) was added 1N NaOH (50 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over $Na_2SO_4$, filtered, concentrated and purified by flash chromatography on a silica gel column (chloroform: methanol 95:5 spiked with acetic acid) to give the title compound as a white solid.

$^1$H NMR (270 MHz, $CDCl_3$): 2.3 (s, 6H); 3.5 (s, 2H); 3.8 (s, 3H); 5.1 (s, 2H); 6.9 (m, 2H); 7.15-7.35 (m, 4H).

Example 8

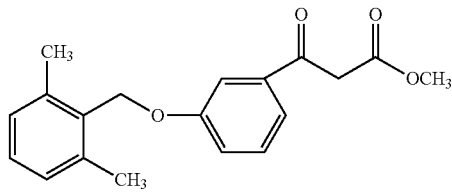 [SMILES: COC(=O)CC(=O)c1cccc(OCc2c(C)cccc2C)c1]

Methyl 3-(3-(2,6-dimethylbenzyloxy)phenyl)-3-oxopropanoate

Step A: Preparation of Methyl 3-(3-(2,6-dimethylbenzyloxy)phenyl)-3-oxopropanoate To a solution of 3-(2,6-Dimethylbenzyloxy)acetophenone (10.40 g, 43.3 mmol) and dimethyl carbonate (64 ml) in DMF (100 ml) was added NaH (60% oil dispersion, 2.38 g, 99 mmol). The resulting mixture was stirred at room temperature for 2 hours, quenched with aqueous HCl and extracted with diethyl ether (2×). The combined organic layers were washed with water, brine, dried over $Na_2SO_4$, filtered, concentrated and purified by flash chromatography eluted with hexane: ethyl acetate (2:1) to give the title compound.

$^1$H NMR (270 MHz, $CDCl_3$): 2.4 (s, 6H); 3.8 (s, 3H); 4.0 (s, 2H); 5.1 (s, 2H); 7.1 (dd, 2H); 7.2 (m, 2H); 7.4 (t, 1H); 7.5-7.6 (m, 2H).

Example 9

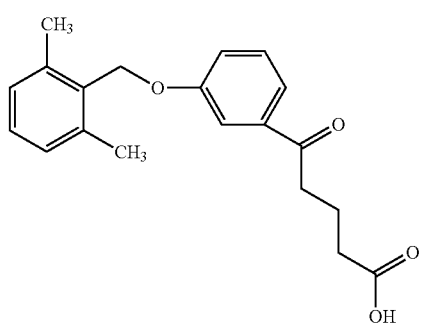 [SMILES: Cc1cccc(C)c1COc1cccc(C(=O)CCCC(=O)O)c1]

5-(3-(2,6-Dimethylbenzyloxy)phenyl)-5-oxopentanoic acid

Step A: Preparation of Ethyl 3-(3-(2,6-dimethylbenzyloxy)phenyl)-3-oxopropanoate To a solution of 3-(2,6-Dimethylbenzyloxy)acetophenone (5.20 g, 21.6 mmol) and diethyl carbonate (43.49 g, 368 mmol) in DMF (50 ml) was added NaH (60% oil dispersion, 1.61 g, 40.2 mmol). The resulting mixture was stirred at room temperature for 2 hours, quenched with aqueous HCl and extracted with diethyl ether (2×). The combined organic layers were washed with water, brine, dried over $Na_2SO_4$, filtered, concentrated and purified by flash chromatography eluted with hexane:ethyl acetate (4:1) to give the title compound.

$^1$H NMR (270 MHz, CDCl$_3$): 1.3 (t, 3H); 2.4 (s, 6H); 4.0 (s, 2H); 4.1 (q, 2H); 5.1 (s, 2H); 7.1 (dd, 2H); 7.2 (m, 2H); 7.4 (t, 1H); 7.5-7.6 (m, 2H).

Step B: Preparation of Diethyl 2-(3-(2,6-dimethylbenzyloxy)benzoyl)pentanedioate To a solution of Ethyl 3-(3-(2,6-dimethylbenzyloxy)phenyl)-3-oxopropanoate (Step A, 5 g, 16.02 mmol) in t-butyl alcohol (50 ml) was added a solution of potassium tert-butoxide (1M in t-butyl alcohol, 1.988 g, 17.7 mmol) and the reaction mixture was stirred for 30 minutes at room temperature. Ethyl 3-bromopropionate was added drop wise to the reaction mixture and stirring continued for another 2 hours and then poured into 1M HCl, extracted with ethyl acetate (2×), washed with brine, dried over Na$_2$SO$_4$, filtered, concentrated and purified by flash chromatography eluted with hexane:ethyl acetate (2:1) to give the title compound.

Step C: Preparation of 5-(3-(2,6-Dimethylbenzyloxy)phenyl)-5-oxopentanoic acid To a solution of Diethyl 2-(3-(2,6-dimethylbenzyloxy)benzoyl)pentanedioate (Step B, 1.66 g, 4.0 mmol) in methanol (50 ml) was added 1N NaOH (17 ml) at the room temperature. The reaction mixture was stirred for 14 hours or until all the starting material is gone, concentrated, diluted in chloroform, and washed with 1M HCl to bring the pH to 3.5 to 4. The organic layer was washed with brine, dried over Na$_2$SO$_4$, filtered, concentrated and purified by flash chromatography eluted with chloroform:methanol (95:5 spiked with acetic acid) to give the title compound.

$^1$H NMR (270 MHz, CDCl$_3$): 2.1 (m, 2H); 2.4 (s, 6H); 2.5 (t, 2H); 3.1 (t, 2H); 5.1 (s, 2H); 7.1 (dd, 2H); 7.2 (m, 2H); 7.4 (t, 1H); 7.5-7.6 (m, 2H).

Example 10

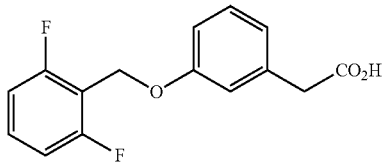 [SMILES: O=C(O)Cc1cccc(OCc2c(F)cccc2F)c1]

2-(3-(2,6-Difluorobenzyloxy)phenyl)acetic acid

Step A: Preparation of Ethyl 2-(3-hydroxyphenyl)acetate

The stirred solution of 2-(3-Hydroxyphenyl)acetic acid (25 g, 164.3 mmol) and p-Toluenesulfonic acid monohydrate (3.49 g, 18.3 mmol) in abs ethanol (250 ml) was refluxed for 4 hours or until all the starting material is consumed. The reaction mixture was concentrated, diluted with ethyl acetate and washed with 1M HCl. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 3.6 (s, 2H); 4.1 (q, 2H); 6.6-6.8 (m, 3H).

Step B: Preparation of Ethyl 2-(3-(2,6-difluorobenzyloxy)phenyl)acetate

To a stirred solution of Ethyl 2-(3-hydroxyphenyl)acetate (4 g, 22.2 mmol) in DMF (20 ml) was added potassium carbonate (4 g, 28.9 mmol) at room temperature followed by drop wise addition of 2,6-Difluorobenzyl bromide (5.06 g, 24.4 mmol). The reaction mixture was stirred for 12 hours and taken in ethyl acetate, washed with water (2×), brine, dried over Na$_2$SO$_4$, filtered, concentrated and purified by flash chromatography on a silica gel column (hex:ethyl acetate 4:1) to give the title compound.

$^1$H NMR (270 MHz, CDCl$_3$): 1.2 (t, 3H); 3.6 (s, 2H); 4.1 (q, 2H); 5.1 (s, 2H); 6.9 (m, 5H); 7.2-7.35 (m, 2H).

Step C: Preparation of 2-(3-(2,6-Difluorobenzyloxy)phenyl)acetic acid

To a stirred solution Ethyl 2-(3-(2,6-difluorobenzyloxy)phenyl)acetate (Step B, 7.86 g, 24 mmol) in absolute ethanol (120 ml) was added 1N NaOH (50 ml) at room temperature. The reaction mixture was stirred for 3 hours, or until all the starting material is gone, concentrated and diluted with chloroform and washed with 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 3.6 (s, 2H); 5.1 (s, 2H); 6.9 (m, 5H); 7.2-7.35 (m, 2H).

Example 11

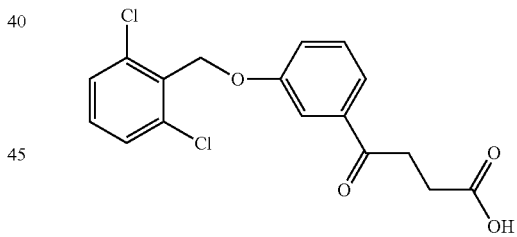

4-(3-(2,6-Dichlorobenzyloxy)phenyl)-4-oxobutanoic acid

Step A: Preparation of 4-(2,6-Dichlorobenzyloxy)acetophenone

A solution of 2,6-Dichlorobenzyl alcohol (15 g, 84.7 mmol) and diisopropyl azodicarboxylate (DIAD, 18.66 g, 92.2 mmol) in THF (50 ml) was added drop wise to a solution of 3-Hydroxyacetophenone (11.53 g, 84.7 mmol) and triphenylphosphine (24.22 g, 92.3 mmol) in THF (200 ml) at 0° C. The reaction mixture was stirred at room temperature for 4 hours, diluted with ether and washed with water, 1N NaOH and brine. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 2.5 (s, 3H); 5.3 (s, 2H); 7.2-7.3 (m, 2H); 7.4 (m, 3H); 7.6 (m, 2H).

Step B: Preparation of Ethyl 4-(3-(2,6-Dichlorobenzyloxy)phenyl)-4-oxobutanoate

To a stirred solution of 4-(2,6-Dichlorobenzyloxy)acetophenone (Step A, 12 g, 40.6 mmol) in dry THF (100 ml) and DMPU (30 ml) was added a solution of lithium bis(trimethylsilyl)amide (1M in THF, 47.21 ml) at –65° C. under argon. After 10 minutes of stirring at –65° C., ethyl bromoacetate (10.18 g, 61 mmol) was added rapidly. The reaction mixture was stirred for an additional 10 minutes and then warmed to room temperature for 4 hours. The crude mixture was taken in ethyl acetate and washed with water and brine. The aqueous layer was extracted one more time with ethyl acetate. The combined organic layers were dried over Na$_2$SO$_4$, filtered, concentrated and purified by flash chromatography on a silica gel column (ethyl acetate:hexane, 1:4) to provide the title compound.
$^1$H NMR (270 MHz, CDCl$_3$): 1.2 (t, 3H); 2.8 (t, 2H); 3.3 (t, 2H); 4.4 (q, 2H); 5.3 (s, 2H); 7.2-7.3 (m, 2H); 7.4 (m, 3H); 7.6 (m, 2H).

Step C: Preparation of 4-(3-(2,6-Dichlorobenzyloxy)phenyl)-4-oxobutanoic acid

A solution of Ethyl 4-(3-(2,6-Dichlorobenzyloxy)phenyl)-4-oxobutanoate (Step B, 14.86 g, 39 mmol) in abs ethanol (100 ml) was treated with 1N NaOH (60 ml) at room temperature. The reaction mixture was stirred for 3 hours, or until all the starting material is gone, concentrated and diluted with chloroform and washed with 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.
$^1$H NMR (270 MHz, CDCl$_3$): 2.8 (t, 2H); 3.3 (t, 2H); 5.3 (s, 2H); 7.2-7.3 (m, 2H); 7.4 (m, 3H); 7.6 (m, 2H).

Example 12

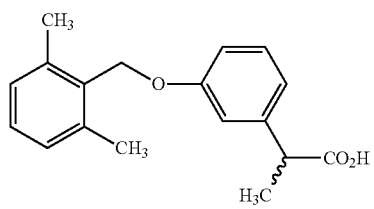 [SMILES: Cc1cccc(C)c1COc1cccc(C(C)C(=O)O)c1]

2-(3-(2,6-Dimethylbenzyloxy)phenyl)propanoic acid

Step A: Preparation of Ethyl 2-(3-(2,6-dimethylbenzyloxy)phenyl)acetate

A solution of 2,6-Dimethylbenzyl alcohol (5.25 g, 38.6 mmol) and diisopropyl azodicarboxylate (DIAD, 8.49 g, 42 mmol) in THF (30 ml) was added drop wise to a solution of Ethyl 3-hydroxyphenylacetate (6.66 g, 37 mmol) and triphenylphosphine (11 g, 42 mmol) in THF (100 ml). The reaction mixture was stirred at room temperature for 4 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.
$^1$H NMR (270 MHz, CDCl$_3$): 1.2 (t, 3H); 2.3 (s, 6H); 3.5 (s, 2H); 4.1 (q, 2H); 5.1 (s, 2H); 6.9 (m, 2H); 7.15-7.35 (m, 5H).

Step B: Preparation of Ethyl 4-(3-(2,6-dimethylbenzyloxy)phenyl)propanoate

To a stirred solution of Ethyl 2-(3-(2,6-dimethylbenzyloxy)phenyl)acetate (Step A, 6.35 g, 21.3 mmol) in dry THF (100 ml) was added a solution of lithium bis(trimethylsilyl)amide (1.0 M in THF, 31.91 ml) at –65° C. under argon. After 10 minutes of stirring at –65° C., iodomethane (15.12 g, 106.5 mmol) was added rapidly. The reaction mixture was warmed to room temperature for 6 hours. The crude mixture was taken in ethyl acetate and washed with water (2×). The aqueous layer was extracted one more time with ethyl acetate. The combined organic layers were washed with brine, dried over Na$_2$SO$_4$, filtered, concentrated and purified by flash chromatography on a silica gel column (ether:hexane, 1:5) to provide the title compound.
$^1$H NMR (270 MHz, CDCl$_3$): 1.2 (t, 3H); 1.5 (m, 3H); 2.4 (s, 6H); 3.7 (m, 1H); 4.1 (q, 2H); 5.1 (s, 2H); 6.9 (m, 2H); 7.15-7.35 (m, 5H).

Step C: Preparation of 4-(3-(2,6-dimethylbenzyloxy)phenyl)propanoic acid

A solution of Ethyl 4-(3-(2,6-dimethylbenzyloxy)phenyl)propanoate (Step B, 1.30 g, 4.2 mmol) in abs ethanol (30 ml) was treated with 1N NaOH (10 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.
$^1$H NMR (270 MHz, CDCl$_3$): 1.5 (m, 3H); 2.4 (s, 6H); 3.7 (m, 1H); 5.1 (s, 2H); 6.9 (m, 2H); 7.15-7.35 (m, 5H).

Example 13

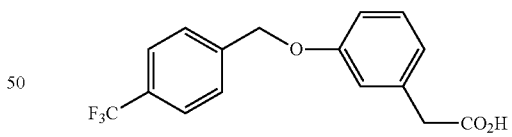

2-(3-(4-(Trifluoromethyl)benzyloxy)phenyl)acetic acid

Step A: Preparation of Ethyl 2-(3-(4-(trifluoromethyl)benzyloxy)phenyl)acetate

To a stirred solution of Ethyl 2-(3-hydroxyphenyl)acetate (7.3 g, 30.5 mmol) in DMF (20 ml) was added potassium carbonate (5.47 g, 39.6 mmol) at room temperature followed by drop wise addition of 4-Trifluoromethylbenzyl bromide (6.04 g, 33.6 mmol). The reaction mixture was stirred for 12 hours and taken in ethyl acetate, washed with water (2×), brine, dried over Na$_2$SO$_4$, filtered, concentrated and purified by flash chromatography on a silica gel column (hex:ether 5:1) to give the title compound.

$^1$H NMR (270 MHz, CDCl$_3$): 1.2 (t, 3H); 3.7 (s, 2H); 4.1 (q, 2H); 5.1 (s, 2H); 6.9 (m, 3H); 7.2 (t, 1H); 7.5-7.7 (m, 4H).

Step B: Preparation of 2-(3-(4-(Trifluoromethyl)benzyloxy)phenyl)acetic acid

To a stirred solution Ethyl 2-(3-(4-(trifluoromethyl)benzyloxy)phenyl)acetate (Step A, 6 g, 17.7 mmol) in absolute ethanol (70 ml) was added 1N NaOH (36 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 3.7 (s, 2H); 5.1 (s, 2H); 6.9 (m, 3H); 7.2 (t, 1H); 7.5-7.7 (m, 4H).

Example 14

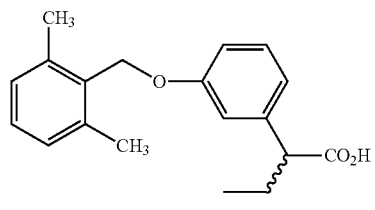 [SMILES: CCC(C(=O)O)c1cccc(OCc2c(C)cccc2C)c1]

2-(3-(2,6-Dimethylbenzyloxy)phenyl)butanoic acid

Step A: Preparation of Ethyl 2-(3-(2,6-dimethylbenzyloxy)phenyl)acetate

A solution of 2,6-Dimethylbenzyl alcohol (5.25 g, 38.6 mmol) and diisopropyl azodicarboxylate (DIAD, 8.49 g, 42 mmol) in THF (30 ml) was added drop wise to a solution of Ethyl 3-hydroxyphenylacetate (6.66 g, 37 mmol) and triphenylphosphine (11 g, 42 mmol) in THF (100 ml). The reaction mixture was stirred at room temperature for 4 hours, diluted with ether and washed with water and brine. The organic layer was dried over Na$_2$SO$_4$, filtered, concentrated, and purified by flash chromatography on a silica gel column (hex:ethyl acetate 4:1) to give the title compound.

$^1$H NMR (270 MHz, CDCl$_3$): 1.2 (t, 3H); 2.3 (s, 6H); 3.5 (s, 2H); 4.1 (q, 2H); 5.1 (s, 2H); 6.9 (m, 2H); 7.15-7.35 (m, 5H).

Step B: Preparation of Ethyl 4-(3-(2,6-dimethylbenzyloxy)phenyl)butanoate

To a stirred solution of Ethyl 2-(3-(2,6-dimethylbenzyloxy)phenyl)acetate (Step A, 4.79 g, 16.0 mmol) in dry THF (60 ml) was added drop wise a solution of lithium diisopropylamide (1.0 M in THF, 25 ml) at −78° C. under argon followed by addition of hexamethylphosphoramide (HMPA, 15 ml). After 15 minutes of stirring at −78° C., Iodoethane (12.53 g, 80.3 mmol) was added rapidly. The reaction mixture was warmed to room temperature for 16 hours. The crude mixture was quenched with sat. NH$_4$Cl and extracted with ether (2×). The combined organic layers were washed with brine, dried over Na$_2$SO$_4$, filtered, concentrated and purified by flash chromatography on a silica gel column (ethyl acetate: hexane, 1:4) to provide the title compound.

$^1$H NMR (270 MHz, CDCl$_3$): 1.0 (t, 3H); 1.2 (m, 3H); 1.8 (m, 1H); 2.1 (m, 1H); 2.4 (s, 6H); 3.4 (m, 1H); 4.1 (q, 2H); 5.1 (s, 2H); 6.9 (m, 2H); 7.15-7.35 (m, 5H).

Step C: Preparation of 4-(3-(2,6-Dimethylbenzyloxy)phenyl)butanoic acid

A solution of Ethyl 4-(3-(2,6-dimethylbenzyloxy)phenyl)butanoate (Step B, 3.26 g, 10 mmol) in abs ethanol (60 ml) was treated with 1N NaOH (20 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

$^1$H NMR (270 MHz, CDCl$_3$): 1.0 (t, 3H); 1.8 (m, 1H); 2.1 (m, 1H); 2.4 (s, 6H); 3.4 (m, 1H); 5.1 (s, 2H); 6.9 (m, 2H); 7.15-7.35 (m, 5H).

Example 15

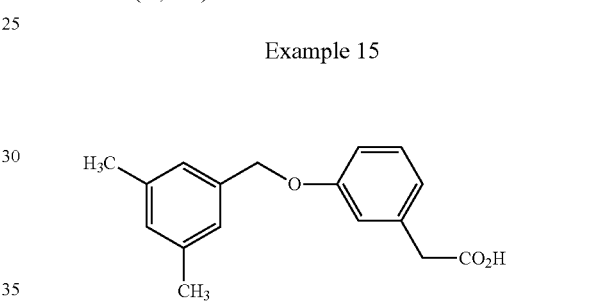

2-(3-(3,5-Dimethylbenzyloxy)phenyl)acetic acid

Step A: Preparation of Ethyl 2-(3-(3,5-dimethylbenzyloxy)phenyl)acetate

To a stirred solution of Ethyl 2-(3-hydroxyphenyl)acetate (3 g, 16.6 mmol) in DMF (20 ml) was added potassium carbonate (2.99 g, 21.6 mmol) at room temperature followed by drop wise addition of 3,5-Dimethylbenzyl bromide (3.30 g, 16.6 mmol). The reaction mixture was stirred for 16 hours and taken in ethyl acetate, washed with water (2×), brine, dried over Na$_2$SO$_4$, filtered, concentrated and purified by flash chromatography on a silica gel column (hex:ethyl acetate 4:1) to give the title compound.

Step B: Preparation of 2-(3-(3,5-Dimethylbenzyloxy)phenyl)acetic acid

To a stirred solution Ethyl 2-(3-(3,5-dimethylbenzyloxy)phenyl)acetate (Step A, 2.38 g, 8.0 mmol) in absolute ethanol (40 ml) was added 1N NaOH (16 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na$_2$SO$_4$, filtered, concentrated and purified by flash chromatography on a silica gel column (chloroform:methanol, 95:5 spiked with acetic acid) to give the title compound as white solid.

¹H NMR (400 MHz, CDCl₃): 2.4 (s, 6H); 3.7 (s, 2H); 5.1 (s, 2H); 6.9 (m, 3H); 7.2 (s, 1H); 7.25-7.35 (m, 3H).

Example 16

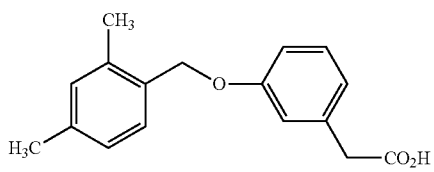 [SMILES: Cc1ccc(COc2cccc(CC(=O)O)c2)c(C)c1]

2-(3-(2,4-Dimethylbenzyloxy)phenyl)acetic acid

Step A: Preparation of Ethyl 2-(3-(2,4-dimethylbenzyloxy)phenyl)acetate

To a stirred solution of Ethyl 2-(3-hydroxyphenyl)acetate (3 g, 16.6 mmol) in DMF (20 ml) was added potassium carbonate (2.99 g, 21.6 mmol) at room temperature followed by drop wise addition of 2,4-Dimethylbenzyl chloride (3.11 g, 18.3 mmol). The reaction mixture was stirred for 16 hours and taken in ethyl acetate, washed with water (2×), brine, dried over Na₂SO₄, filtered, concentrated and purified by flash chromatography on a silica gel column (hex:ethyl acetate 4:1) to give the title compound.

Step B: Preparation of 2-(3-(2,4-Dimethylbenzyloxy)phenyl)acetic acid

To a stirred solution Ethyl 2-(3-(2,4-dimethylbenzyloxy) phenyl)acetate (Step A, 0.900 g, 3.0 mmol) in absolute ethanol (25 ml) was added 1N NaOH (10 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na₂SO₄, filtered, concentrated and purified by flash chromatography on a silica gel column (chloroform:methanol, 95:5 spiked with acetic acid) to give the title compound as white solid.

¹H NMR (400 MHz, CDCl₃): 2.4 (s, 6H); 3.6 (s, 2H); 5.1 (s, 2H); 6.9 (m, 3H); 7.25-7.35 (m, 4H).

Example 17

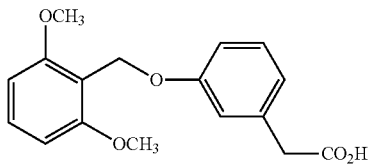 [SMILES: COc1cccc(OC)c1COc1cccc(CC(=O)O)c1]

2-(3-(2,6-Dimethoxybenzyloxy)phenyl)acetic acid

Step A: Preparation of Ethyl 2-(3-(2,6-Dimethoxybenzyloxy)phenyl)acetate

A solution of 2,6-Dimethoxybenzyl alcohol (3.33 g, 19.8 mmol) and diisopropyl azodicarboxylate (DIAD, 4.36 g, 21.6 mmol) in THF (30 ml) was added drop wise to a solution of Ethyl 2-(3-hydroxyphenyl)acetate (4 g, 22.2 mmol) and triphenylphosphine (5.66 g, 21.6 mmol) in THF (80 ml). The reaction mixture was stirred at room temperature for 8 hours, diluted with ether and washed with water and brine. The organic layer was dried over Na₂SO₄, filtered, concentrated, and purified by flash chromatography on a silica gel column (hex:ethyl acetate 4:1) to give the title compound.

Step B: Preparation of 2-(3-(2,6-Dimethoxybenzyloxy)phenyl)acetic acid

To a stirred solution Ethyl 2-(3-(2,6-Dimethoxybenzyloxy)phenyl)acetate (Step A, 6 g, 18.2 mmol) in absolute ethanol (100 ml) was added 1N NaOH (40 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na₂SO₄, filtered, concentrated and purified by flash chromatography on a silica gel column (chloroform:methanol, 95:5 spiked with acetic acid) to give the title compound as white solid.

¹H NMR (400 MHz, CDCl₃): 3.7 (s, 2H); 3.8 (s, 6H); 5.1 (s, 2H); 6.5 (d, 2H); 6.8-7.1 (m, 3H); 7.2 (d, 1H); 7.3 (t, 1H).

Example 18

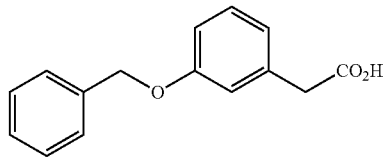 [SMILES: O=C(O)Cc1cccc(OCc2ccccc2)c1]

2-(3-(Benzyloxy)phenyl)acetic acid

Step A: Preparation of Ethyl 2-(3-(benzyloxy)phenyl)acetate

To a stirred solution of Ethyl 2-(3-hydroxyphenyl)acetate (3 g, 16.6 mmol) in DMF (25 ml) was added potassium carbonate (2.99 g, 21.6 mmol) at room temperature followed by drop wise addition of benzyl bromide (3.13 g, 18.3 mmol). The reaction mixture was stirred for 16 hours and taken in ethyl acetate, washed with water (2×) and brine. The organic layer was dried over Na₂SO₄, filtered, concentrated and purified by flash chromatography on a silica gel column (hex: ethyl acetate 4:1) to give the title compound.

Step B: Preparation of 2-(3-(Benzyloxy)phenyl)acetic acid

To a stirred solution Ethyl 2-(3-(benzyloxy)phenyl)acetate (Step A, 5.00 g, 18.5 mmol) in absolute ethanol (100 ml) was added 1N NaOH (40 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na₂SO₄, filtered, concentrated and purified by flash chromatography on a silica gel column (chloroform:methanol, 95:5 spiked with acetic acid) to give the title compound as white solid.

¹H NMR (400 MHz, CDCl₃): 3.6 (s, 2H); 5.1 (s, 2H); 6.8 (m, 2H); 7.1 (s, 1H), 7.2 (t, 1H), 7.35-7.45 (m, 5H).

Example 19

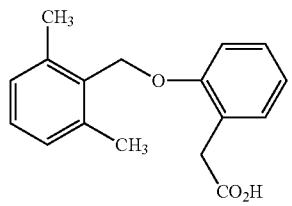 [SMILES: Cc1cccc(C)c1COc1ccccc1CC(=O)O]

2-(2-(2,6-Dimethylbenzyloxy)phenyl)acetic acid

Step A: Preparation of Ethyl 2-(2-hydroxyphenyl)acetate

The stirred solution of 2-(2-Hydroxyphenyl)acetic acid (10 g, 65.7 mmol) and p-Toluenesulfonic acid monohydrate (1.40 g, 7.3 mmol) in abs ethanol (100 ml) was refluxed for 4 hours or until all the starting material is consumed. The reaction mixture was concentrated, diluted with ethyl acetate and washed with 1M HCl and brine. The organic layer was dried over Na₂SO₄, filtered, concentrated, and purified by flash chromatography on a silica gel column (hex:ethyl acetate 2:1) to give the title compound.

Step B: Preparation of Ethyl 2-(2-(2,6-dimethylbenzyloxy)phenyl)acetate

A solution of 2,6-Dimethylbenzyl alcohol (2.72 g, 19.9 mmol) and diisopropyl azodicarboxylate (DIAD, 3.67 g, 18.2 mmol) in THF (30 ml) was added drop wise to a solution of Ethyl 2-(2-hydroxyphenyl)acetate (3 g, 16.6 mmol) and triphenylphosphine (4.76 g, 18.2 mmol) in THF (80 ml). The reaction mixture was stirred at room temperature for 6 hours, diluted with ether and washed with water and brine. The organic layer was dried over Na₂SO₄, filtered, concentrated, and purified by flash chromatography on a silica gel column (hex:ethyl acetate 4:1) to give the title compound.

Step C: Preparation of 2-(2-(2,6-Dimethylbenzyloxy)phenyl)acetic acid

To a stirred solution Ethyl 2-(2-(2,6-dimethylbenzyloxy) phenyl)acetate (Step B, 4.70 g, 15.7 mmol) in absolute ethanol (75 ml) was added 1N NaOH (35 ml) at room temperature. The reaction mixture was stirred for 3 hours, or until all the starting material is gone, concentrated and diluted with chloroform and acidified by 1M HCl to bring the pH to 3.5-4. The organic layer was washed with brine, dried over Na₂SO₄, filtered, concentrated and purified by flash chromatography on a silica gel column (chloroform:methanol, 95:5 spiked with acetic acid) to give the title compound as white solid.

¹H NMR (400 MHz, CDCl₃): 2.35 (s, 6H); 3.6 (s, 2H); 5.1 (s, 2H); 7.0 (t, 1H); 7.1 (s, 1H), 7.2-7.25 (m, 2H), 7.30-7.35 (m, 2H); 7.4 (t, 1H).

Example 20

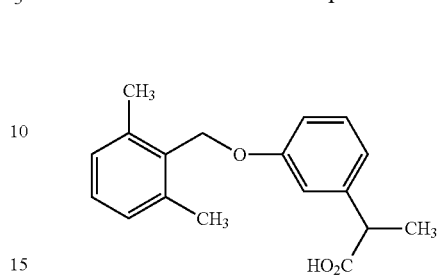

2-(3-(2,6-Dimethylbenzyloxy)phenyl)propanoic acid

Step A: Preparation of Ethyl 2-(3-hydroxyphenyl)acetate

A solution of 2-(3-Hydroxyphenyl)acetic acid (25 g, 164.31 mmol) and p-Toluenesulfonic acid monohydrate (3.49 g, 18.3 mmol) in abs ethanol (250 ml) was refluxed for 4 hours or until all the starting material is consumed. The reaction mixture was concentrated, diluted with ethyl acetate and washed with water. The organic layer was dried over Na₂SO₄, filtered, concentrated, and purified by flash chromatography on a silica gel column (hex:ethyl acetate, 2:1) to give the title compound.

¹H NMR (270 MHz, CDCl₃): 1.2 (t, 3H); 3.5 (s, 2H); 4.1 (q, 2H); 6.6-7.2 (m, 4H).

Step B: Preparation of Ethyl 2-(3-(2,6-dimethylbenzyloxy)phenyl)acetate

A solution of 2,6-Dimethylbenzyl alcohol (5.25 g, 38.6 mmol) and diisopropyl azodicarboxylate (DIAD, 8.49 g, 42 mmol) in THF (30 ml) and DMF (13 ml) was added drop wise to a solution of Ethyl 2-(3-hydroxyphenyl)acetate (Step A, 6.66 g, 37 mmol) and triphenylphosphine (TPP, 11 g, 42 mmol) in THF (100 ml). The reaction mixture was stirred at room temperature for 4 hours, diluted with ether and washed with water. The organic layer was dried over Na₂SO₄, filtered, concentrated, and purified by flash chromatography on a silica gel column (hex:ethyl acetate, 4:1) to give the title compound.

¹H NMR (270 MHz, CDCl₃): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of Ethyl 2-(3-(2,6-dimethylbenzyloxy)phenyl)propanoate

To a stirred solution of Ethyl 2-(3-(2,6-dimethylbenzyloxy)phenyl)acetate (Step B, 4 g, 13.6 mmol) in dry THF (30 ml) at −68° C. under a dry argon atmosphere was added LiHMDS drop wise (1 M solution in THF, 17.45 ml, 17.4 mmol), and the resulting orange solution was stirred at low temperature for 30 minutes before CH₃I (5.71 g, 40.26 mmol) was added. The reaction mixture was slowly warmed to room temperature and stirred for another 15 hours. The reaction was quenched with ice, and the product was extracted with EtOAc (2×), the organic layer was washed with brine, dried over Na₂SO₄, filtered, concentrated and purified by flash chromatography on a silica gel column (hex:ether, 5:1) to give the title compound.

$^1$H NMR (270 MHz, CDCl$_3$): 1.2 (t, 3H); 1.5 (t, 3H); 2.4 (s, 6H); 3.7 (m, 1H); 4.1 (q, 2H); 5.0 (s, 2H); 6.9 (m, 2H); 7.15-7.35 (m, 5H).

Step D: Preparation of 2-(3-(2,6-Dimethylbenzyloxy)phenyl)propanoic acid

To a stirred solution of Ethyl 2-(3-(2,6-dimethylbenzyloxy)phenyl)propanoate (Step C, 3 g, 9.6 mmol) in absolute ethanol (60 ml) was added 1N NaOH (20 ml) at room temperature. The reaction mixture was stirred for 3 hours, acidified to pH 3.5-4.0 by adding 1N HCl and concentrated. The residue was taken into chloroform and washed with 0.1N HCl, brine, dried over Na$_2$SO$_4$, filtered, concentrated and purified by flash chromatography on a silica gel column (chloroform:methanol, 95:5 spiked with acetic acid) to give the title compound.

$^1$H NMR (270 MHz, CDCl$_3$): 1.5 (t, 3H); 2.4 (s, 6H); 3.7 (m, 1H); 5.0 (s, 2H); 6.9 (m, 2H); 7.15-7.35 (m, 5H).

Example 21

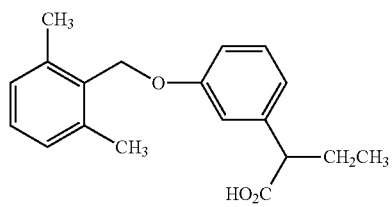

2-(3-(2,6-Dimethylbenzyloxy)phenyl)butanoic acid

Step A: Preparation of Ethyl 2-(3-hydroxyphenyl)acetate

Using the method of Example 20, Step A, the title compound was obtained.

$^1$H NMR (270 MHz, CDCl$_3$): 1.2 (t, 3H); 3.5 (s, 2H); 4.1 (q, 2H); 6.6-7.2 (m, 4H).

Step B: Preparation of Ethyl 2-(3-(2,6-dimethylbenzyloxy)phenyl)acetate

Using the method of Example 20, Step B, the title compound was obtained.

$^1$H NMR (270 MHz, CDCl$_3$): 1.2 (t, 3H); 2.4 (s, 6H); 3.5 (s, 2H); 4.1 (q, 2H); 5.1 (s, 2H); 6.9 (m, 2H); 7.15-7.35 (m, 5H).

Step C: Preparation of Ethyl 2-(3-(2,6-dimethylbenzyloxy)phenyl)butanoate

To a stirred solution of Ethyl 2-(3-(2,6-dimethylbenzyloxy)phenyl)acetate (Step B, 4.84 g, 16.2 mmol) in dry THF (60 ml) and HMPA (15 ml) at −78° C. under dry argon atmosphere was added LDA drop wise (2 M solution in THF, 25 ml, 48.72 mmol), and the resulting orange solution was stirred at low temperature for 30 minutes before C$_2$H$_5$I (10.13 g, 64.96 mmol) was added. The reaction mixture was slowly warmed to room temperature and stirred for another 15 hours. The reaction was quenched with aqueous citric acid, and the product was extracted with EtOAc (2×), the organic phase was washed with brine, dried over Na$_2$SO$_4$, filtered, concentrated and purified by flash chromatography on a silica gel column (hex:ethyl acetate, 4:1) to give the title compound.

$^1$H NMR (270 MHz, CDCl$_3$): 0.9 (t, 3H); 1.2 (t, 3H); 1.8 (m, 1H); 2.1 (m, 1H); 2.4 (s, 6H); 3.4 (t, 1H); 4.1 (q, 2H); 5.0 (s, 2H); 6.9 (m, 2H); 7.15-7.30 (m, 5H).

Step D: Preparation of 2-(3-(2,6-Dimethylbenzyloxy)phenyl)butanoic acid

To a stirred solution of Ethyl 2-(3-(2,6-dimethylbenzyloxy)phenyl)butanoate (Step C, 3.26 g, 10.0 mmol) in absolute ethanol (60 ml) was added 1N NaOH (20 ml) at room temperature. The reaction mixture was stirred for 3 hours, acidified to pH 3.5-4.0 by adding 1N HCl, and concentrated. The residue was taken into chloroform and washed with 0.1N HCl, brine, dried over Na$_2$SO$_4$, filtered, concentrated and purified by flash chromatography on a silica gel column (chloroform:methanol, 95:5 spiked with acetic acid) to give the title compound.

$^1$H NMR (270 MHz, CDCl$_3$): 0.9 (t, 3H); 1.8 (m, 1H); 2.1 (m, 1H); 2.4 (s, 6H); 3.4 (t, 1H); 5.0 (s, 2H); 6.9 (m, 2H); 7.15-7.30 (m, 5H).

Example 22

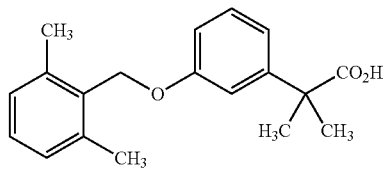 [SMILES: Cc1cccc(C)c1COc1cccc(C(C)(C)C(=O)O)c1]

2-(3-(2,6-Dimethylbenzyloxy)phenyl)-2-methylpropanoic acid

Step A: Preparation of 2-(3-methoxyphenyl)-2-methylpropanenitrile

To a stirred solution of 2-(3-methoxyphenyl)acetonitrile (6.2 g, 42.1 mmol), 40% aq tetrabutylammonium hydroxide (5.1 g, 7.8 mmol) and 50% aq NaOH (30 g, 375 mmol) in toluene (30 ml) was added CH$_3$I (8 ml, 129 mmol) at room temperature. The reaction mixture was stirred for 16 hours, CH$_3$I (4 ml) was further added and the reaction mixture was stirred for another 5 hours at room temperature. The reaction mixture was diluted with EtOAc and washed with water and brine. The organic layer was dried over Na$_2$SO$_4$, filtered, concentrated, and purified by flash chromatography on a short silica gel column (hex:methylene chloride, 2:1) to give the title compound.

$^1$H NMR (400 MHz, d-DMSO): 1.74 (s, 6H); 3.8 (s, 3H); 6.9-7.04 (m, 2H); 7.11 (t, 1H); 7.29-7.31 (m, 1H).

Step B: Preparation of 2-(3-hydroxyphenyl)-2-methylpropanenitrile

To a stirred solution of 2-(3-methoxyphenyl)-2-methylpropanenitrile (Step A, 4.5 g, 25.7 mmol) in methylene chloride (30 ml) was added BBr$_3$ (1M in CH$_2$Cl$_2$, 50 ml) at −78° C. under argon, the cold bath was substituted by ice bath after 30 minutes and the reaction was stirred at the same temperature for 2 hours and then 30 minutes at room temperature. The reaction mixture was quenched by addition of ice and worked up by washing with water and brine. The organic layer was dried over Na$_2$SO$_4$, filtered, concentrated, and purified by flash chromatography on a silica gel column (methylene chloride:ethyl acetate, 5:1) to give the title compound.

Step C: Preparation of 2-(3-(2,6-Dimethylbenzyloxy)phenyl)-2-methylpropanenitrile A solution of 2,6-Dimethylbenzyl alcohol (2.76 g, 20.3 mmol) and diisopropyl azodicarboxylate (DIAD, 4.7 g, 23.2 mmol) in THF (20 ml) was added drop wise to a solution of 2-(3-hydroxyphenyl)-2-methylpropanenitrile (Step B, 3.2 g, 19.8 mmol) and triphenylphosphine (5.28 g, 20.1 mmol) in THF (50 ml) at 0° C. under argon. The reaction mixture was stirred at the same temperature for 16 hours, diluted with ether and washed with water. The organic layer was dried over Na$_2$SO$_4$, filtered, concentrated, and purified by flash chromatography on a silica gel column (hex:ethyl acetate, 9:1) to give the title compound.

Step D: Preparation of 2-(3-(2,6-Dimethylbenzyloxy)phenyl)-2-methylpropanal

To a stirred solution of 2-(3-(2,6-Dimethylbenzyloxy)phenyl)-2-methylpropanenitrile (Step C, 3.5 g, 12.5 mmol) in dry methylene chloride (40 ml) at −78° C. under dry argon atmosphere was added DIBAL-H drop wise (1 M solution in CH$_2$Cl$_2$, 40 ml), and the reaction mixture was stirred at the same temperature for 2 hours or until the reaction is complete as indicated by TLC. The reaction mixture was slowly quenched with ice cold water and the product was extracted with CH$_2$Cl$_2$ (2×), the organic phase was washed with 1M HCl, brine, dried over Na$_2$SO$_4$, filtered, concentrated and purified by flash chromatography on a silica gel column (hex:ether, 9:1) to give the title compound.

Step E: Preparation of 2-(3-(2,6-Dimethylbenzyloxy)phenyl)-2-methylpropanoic acid To a stirred solution of 2-(3-(2,6-Dimethylbenzyloxy)phenyl)-2-methylpropanal (Step D, 1.9 g, 6.7 mmol) in acetone (40 ml) was added drop wise jones reagent (10 ml) at room temperature. The reaction mixture was stirred for 3 hours, and was taken in EtOAc and washed with water, brine, dried over Na$_2$SO$_4$, filtered, concentrated and purified by flash chromatography on a silica gel column (chloroform:methanol, 95:5 spiked with acetic acid) to give the title compound.

$^1$H NMR (400 MHz, d-DMSO): 1.46 (s, 6H); 2.33 (s, 6H); 5.0 (s, 2H); 6.92-6.98 (m, 3H); 7.07 (d, 2H); 7.15-7.18 (t, 1H); 7.27-7.30 (t, 1H).

Example 23

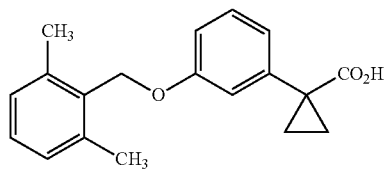 [SMILES: Cc1cccc(C)c1COc1cccc(C2(C(=O)O)CC2)c1]

1-(3-(2,6-Dimethylbenzyloxy)phenyl)cyclopropanecarboxylic acid

Step A: Preparation of 1-(3-methoxyphenyl)cyclopropanecarbonitrile

To a stirred solution of 2-(3-methoxyphenyl)acetonitrile (6.5 g, 44.1 mmol), 40% aq tetrabutylammonium hydroxide (4.5 ml) and 50% aq NaOH (30 ml) in toluene (30 ml) was added 1,2-dibromoethane (10 ml, 116 mmol) at room temperature. The reaction mixture was stirred for 16 hours, diluted with EtOAc and washed with water and brine. The organic layer was dried over Na$_2$SO$_4$, filtered, concentrated, and purified by flash chromatography on a short silica gel column (hex:ethyl acetate, 9:1) to give the title compound.

$^1$H NMR (400 MHz, CDCl$_3$): 1.41-1.43 (m, 2H); 1.70-1.71 (m, 2H); 3.8 (s, 3H); 6.84-6.88 (m, 3H); 7.25 (t, 1H).

Step B: Preparation of 1-(3-hydroxyphenyl)cyclopropanecarbonitrile

To a stirred solution of 1-(3-methoxyphenyl)cyclopropanecarbonitrile (Step A, 6.4 g, 37 mmol) in methylene chloride (30 ml) was added BBr$_3$ (1M in CH$_2$Cl$_2$, 80 ml) at −78° C. under argon, the cold bath was substituted by ice bath after 30 minutes and reaction was stirred at the same temperature for 2 hours and then 30 minutes at room temperature. The reaction mixture was quenched by addition of ice and worked up by washing with water and brine. The organic layer was dried over Na$_2$SO$_4$, filtered, concentrated, and purified by flash chromatography on a silica gel column (methylene chloride: ethyl acetate, 5:1) to give the title compound.

Step C: Preparation of 1-(3-(2,6-Dimethylbenzyloxy)phenyl)cyclopropanecarbonitrile A solution of 2,6-Dimethylbenzyl alcohol (2.81 g, 20.6 mmol) and diisopropyl azodicarboxylate (DIAD, 4.69 g, 23.2 mmol) in THF (20 ml) was added drop wise to a solution of 1-(3-hydroxyphenyl)cyclopropanecarbonitrile (Step B, 3.2 g, 20.1 mmol) and triphenylphosphine (5.37 g, 20.5 mmol) in THF (50 ml) at 0° C. under argon. The reaction mixture was stirred at the same temperature for 16 hours, diluted with ether and washed with water. The organic layer was dried over Na$_2$SO$_4$, filtered, concentrated, and purified by flash chromatography on a silica gel column (hex:ethyl acetate, 9:1) to give the title compound.

Step D: Preparation of 1-(3-(2,6-Dimethylbenzyloxy)phenyl)cyclopropanecarbaldehyde To a stirred solution of 1-(3-(2,6-Dimethylbenzyloxy)phenyl)cyclopropanecarbonitrile (Step C, 4.6 g, 16.6 mmol) in dry methylene chloride (40 ml) at −78° C. under argon was added DIBAL-H drop wise (1 M solution in CH$_2$Cl$_2$, 40 ml), and the reaction mixture was stirred at the same temperature for 6 hours or until the reaction is complete as indicated by TLC. The reaction mixture was slowly quenched with ice cold water and the product was extracted with CH$_2$Cl$_2$ (2×), the organic phase was washed with 1M HCl, brine, dried over Na$_2$SO$_4$, filtered, concentrated and purified by flash chromatography on a silica gel column (hex:ether, 9:1) to give the title compound.

Step E: Preparation of 1-(3-(2,6-Dimethylbenzyloxy)phenyl)cyclopropanecarboxylic acid To a stirred solution of 1-(3-(2,6-Dimethylbenzyloxy)phenyl)cyclopropanecarbaldehyde (Step D, 3.5 g, 12.5 mmol) in acetone (50 ml) was added drop wise jones reagent (15 ml) at room temperature. The reaction mixture was stirred for 6 hours, diluted in EtOAc and washed with water, brine, dried over $Na_2SO_4$, filtered, concentrated and purified by flash chromatography on a silica gel column (chloroform:methanol, 95:5 spiked with acetic acid) to give the title compound.

$^1$H NMR (400 MHz, d-DMSO): 1.12-1.15 (m, 2H); 1.40-1.43 (m, 2H); 2.32 (s, 6H); 5.0 (s, 2H); 6.90-6.96 (m, 3H); 7.05 (d, 2H); 7.13-7.17 (m, 1H); 7.20-7.24 (t, 1H).

Example 24

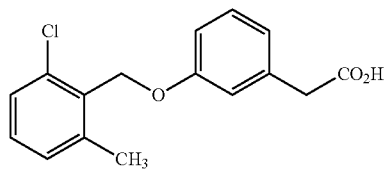

2-(3-(2-Chloro-6-methylbenzyloxy)phenyl)acetic acid

Step A: Preparation of (2-chloro-6-methylphenyl)methanol

To a stirred solution of 2-chloro-6-methylbenzaldehyde (6.11 g, 39.5 mmol) in THF(2): methanol(3) (30 ml) was added in portion $NaBH_4$ (2.24 g, 59.28 mmol) at 0° C. under argon. The reaction mixture was stirred at the same temperature for 1.3 hours and then quenched with cold sat. $NH_4Cl$ solution, extracted with EtOAc, dried over $Na_2SO_4$, filtered, concentrated, and purified by flash chromatography on a silica gel column (hex:ethyl acetate, 2:1) to give the title compound.

Step B: Preparation of Ethyl 2-(3-(2-chloro-6-methylbenzyloxy)phenyl)acetate

A solution of (2-chloro-6-methylphenyl)methanol (Step A, 3 g, 19.1 mmol) and diisopropyl azodicarboxylate (DIAD, 4.13 ml, 21 mmol) in THF (20 ml) was added drop wise to a solution of ethyl 2-(3-hydroxyphenyl)acetate (3.79 g, 21 mmol) and triphenylphosphine (5.48 g, 21 mmol) in THF (30 ml) at 0° C. under argon. The reaction mixture was stirred at the same temperature for 4 hours, diluted with ether and washed with water. The organic layer was dried over $Na_2SO_4$, filtered, concentrated, and purified by flash chromatography on a silica gel column (hex:ethyl acetate, 2:1) to give the title compound.

Step C: Preparation of 2-(3-(2-Chloro-6-methylbenzyloxy)phenyl)acetic acid

To a stirred solution of Ethyl 2-(3-(2-chloro-6-methylbenzyloxy)phenyl)acetate (Step B, 4.94 g, 15.5 mmol) in absolute ethanol (80 ml) was added 1N NaOH (40 ml) at room temperature. The reaction mixture was stirred for 3 hours, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound.

$^1$H NMR (400 MHz, $CDCl_3$): 2.4 (s, 3H); 3.7 (s, 2H); 5.2 (s, 2H); 6.9 (m, 3H); 7.2-7.3 (m, 3H); 7.4 (m, 1H).

Example 25

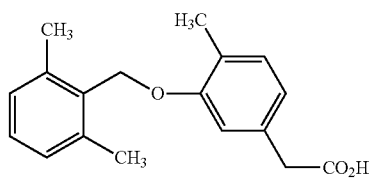 [SMILES: Cc1cccc(C)c1COc1cc(CC(=O)O)ccc1F]

2-(3-(2,6-dimethylbenzyloxy)-4-methylphenyl)acetic acid

Step A: Preparation of 2-(3-methoxy-4-methylphenyl)acetic acid

To a stirred solution of 2-(3-methoxy-4-methylphenyl)acetonitrile (5 g, 31 mmol) in abs ethanol (25 ml) was added 2M NaOH (20 ml) at room temperature and reaction mixture was refluxed for 16 hours or until starting material is gone. The reaction mixture was concentrated, diluted in chloroform and pH was adjusted to 4 by addition of 1N HCl, The organic layer was washed with brine, dried over $Na_2SO_4$, filtered, concentrated, to give off white solid. The solid was washed with hexane, filtered, dried under vacuum and purified by flash chromatography on a silica gel column (chloroform:methanol, 95:5) to give the title compound.

$^1$H NMR (400 MHz, $CDCl_3$): 2.19 (s, 3H); 3.62 (s, 2H); 3.82 (s, 3H); 6.74 (m, 3H); 7.14 (d, 1H).

Step B: Preparation of Ethyl 2-(3-methoxy-4-methylphenyl)acetate

To a stirred solution of 2-(3-methoxy-4-methylphenyl)acetic acid (Step A, 4.64 g, 25.7 mmol) in ethanol (100 ml) was added p-TsOH (0.7 g, 3.7 mmol) at room temperature under argon and the reaction mixture was refluxed for 12 hours or until all the starting material is consumed, concentrated, diluted in EtOAc and washed with 0.1N HCl, brine, dried over $Na_2SO_4$, filtered, concentrated and purified by flash chromatography on a silica gel column (hexane:ethyl acetate, 2:1) to give the title compound.

$^1$H NMR (400 MHz, $CDCl_3$): 1.25 (t, 3H); 2.10 (s, 3H); 3.57 (s, 2H); 3.82 (s, 3H); 4.14 (q, 2H); 6.76 (m, 3H); 7.14 (d, 1H).

Step C: Preparation of Ethyl 2-(3-hydroxy-4-methylphenyl)acetate

To a stirred solution of Ethyl 2-(3-methoxy-4-methylphenyl)acetate (Step B, 4.12 g, 19.8 mmol) in methylene chloride (30 ml) was added $BBr_3$ (1M in $CH_2Cl_2$, 25 ml) at −78° C. under argon, the cold bath was substituted by ice bath after 30 minutes and the reaction mixture was stirred at the same temperature for 2 hours and then 30 minutes at room temperature. The reaction mixture was quenched by addition of ice and worked up by washing with water and brine. The organic layer was dried over $Na_2SO_4$, filtered, concentrated, and purified by flash chromatography on a silica gel column (hexane:ethyl acetate, 2:1) to give the title compound.

Step D: Preparation of Ethyl 2-(3-(2,6-dimethylbenzyloxy)-4-methylphenyl)acetate To a stirred solution of Ethyl 2-(3-hydroxy-4-methylphenyl)acetate (Step C, 1.84 g, 9.5 mmol), $K_2CO_3$ (1.96 g, 14.2 mmol) in DMF (10 ml) was added 2,6-Dimethylbenzyl chloride (1.61 g, 10.4 mmol) at room temperature under argon. The reaction mixture was stirred for 16 hours at the room temperature, diluted with ethyl acetate and washed with water (2×), and brine. The organic layer was dried over $Na_2SO_4$, filtered, concentrated, and purified by flash chromatography on a silica gel column (hexane:ethyl acetate, 4:1) to give the title compound.

Step E: Preparation of 2-(3-(2,6-dimethylbenzyloxy)-4-methylphenyl)acetic acid To a stirred solution of Ethyl 2-(3-(2,6-dimethylbenzyloxy)-4-methylphenyl)acetate (Step D, 1.1 g, 3.5 mmol) in absolute ethanol (20 ml) was added 1N NaOH (7 ml) at room temperature. The reaction mixture was stirred for 3 hours, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound.

$^1$H NMR (400 MHz, $CDCl_3$): 2.15 (s, 3H); 2.38 (s, 6H); 3.67 (s, 2H); 5.02 (s, 2H); 6.8 (d, 1H); 6.9 (s, 1H); 7.0-7.2 (m, 4H).

Example 26

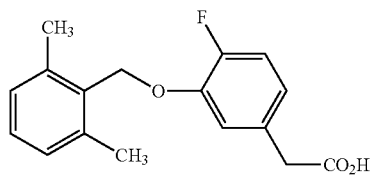

2-(3-(2,6-dimethylbenzyloxy)-4-fluorophenyl)acetic acid

Step A: Preparation of Ethyl 3-(2,6-dimethylbenzyloxy)-4-fluorobenzoate

To a stirred solution of Ethyl 4-fluoro-3-hydroxybenzoate (2.814 g, 15.3 mmol), $K_2CO_3$ (1.95 g, 14.1 mmol) in DMF (15 ml) was added 2,6-Dimethylbenzyl chloride (2.21 g, 14.3 mmol) at room temperature under argon. The reaction mixture was stirred for 16 hours at the room temperature, diluted with ethyl acetate and washed with water (2×), and brine. The organic layer was dried over $Na_2SO_4$, filtered, concentrated, and purified by flash chromatography on a silica gel column (hexane:ethyl acetate, 4:1) to give the title compound.

Step B: Preparation of (3-(2,6-dimethylbenzyloxy)-4-fluorophenyl)methanol

The solution of Ethyl 3-(2,6-dimethylbenzyloxy)-4-fluorobenzoate (Step A, 4.2 g, 13.9 mmol) in dry THF (20 ml) was added slowly to a suspension of $LiAlH_4$ (0.72 g) in dry THF (20 ml) at −78° C. under argon. The cold bath was replaced by ice bath and the reaction mixture was left to stir for 3 hours or until reaction is complete, quenched very slowly with ice and diluted with ethyl acetate. The organic layer was washed with 0.1N HCl, brine, dried over $Na_2SO_4$, filtered, concentrated and purified by flash chromatography on a silica gel column (hexane:ethyl acetate, 5:1) to give the title compound.

Step C: Preparation of 2-((5-(chloromethyl)-2-fluorophenoxy)methyl)-1,3-dimethylbenzene To a stirred solution of (3-(2,6-dimethylbenzyloxy)-4-fluorophenyl)methanol (Step B, 3.7 g, 14.21 mmol), triethylamine (5 g, 50 mmol) in $CH_2Cl_2$ (50 ml) was added mesyl chloride (10.34 g, 90.2 mmol) at 0° C. under argon. The reaction mixture was stirred for 6 hours, washed with 10% $Na_2CO_3$, dried over $Na_2SO_4$, filtered, concentrated and purified by flash chromatography on a silica gel column (hexane:ethyl acetate, 5:1) to give the title compound.

Step D: Preparation of 2-(3-(2,6-Dimethylbenzyloxy)-4-fluorophenyl)acetonitrile To a stirred solution of 2-((5-(chloromethyl)-2-fluorophenoxy)methyl)-1,3-dimethylbenzene (Step C, 4 g, 14.3 mmol), KI (0.33 g) in DMF (30 ml) was added NaCN (1.02 g, 20.8 mmol). The reaction mixture was heated at 100° C. for 4 hours, concentrated, diluted with EtOAc and washed with water (2×), dried over $Na_2SO_4$, filtered, concentrated and purified by flash chromatography on a silica gel column (hexane:methylene chloride, 1:1) to give the title compound.

Step E: Preparation of 2-(3-(2,6-dimethylbenzyloxy)-4-fluorophenyl)acetic acid To a stirred solution of 2-(3-(2,6-Dimethylbenzyloxy)-4-fluorophenyl)acetonitrile (Step D, 1.44 g, 5.34 mmol) in ethanol (30 ml) was added 2N NaOH (15 ml) and reaction mixture was refluxed for 16 hours, cooled by adding ice and acidified with 1N HCl to pH 4, and diluted with chloroform. The organic layer was dried over $Na_2SO_4$, filtered, concentrated and purified by flash chromatography on a silica gel column (chloroform:methanol, 95:5) to give the title compound.

$^1$H NMR (400 MHz, $CDCl_3$): 2.43 (s, 6H); 3.65 (s, 2H); 5.12 (s, 2H); 6.8 (m, 1H); 7.0-7.15 (m, 4H); 7.17 (m, 1H).

Example 27

Rat oral single-dose pharmacokinetic study with Compound EH

Protocol:

A. Plasma.
1. Male Sprague-Dowley rats received single oral gavage of Compound EH, 100 mg/kg, and plasma was collected at certain times.
2. Rat plasma was stored at −80° C. until the day of analysis.
3. Samples were thawed on 37° C. bath for 5 min and vortexed at top speed for 10 sec.
4. Rat plasma, 0.1 mL was mixed with 0.2 mL Acetonitrile, vortexed 1 min, spun down 14000 rpm, 17000 g, at 4° C., for 25 min.
5. Supernatants were filtered through 0.45 micron, 4 mm, PTFE membrane syringe filter (Phenomenex #AF0-3102-52), and 15 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 mL/min, 107 bar, 37° C. column temperature, method 406975M1, Sequence 0226-09A, Agilent 1100 LC-MS.

All samples were run in duplicate, 210 nm and 230 nm Absorbances, Negative and Positive ionization spectrograms recorded.

B. Calibration Curve.

Step 1. Rat plasma from V2 and V3 animals ("vehicle", pooled), 0.19 mL, was mixed with 0.01 mL 20× stock of Compound EH in Methanol to make 500 microM, 250 microM, 125 microM, . . . , concentrations of Compound EH in plasma.

For example: 190 microL plasma+10 microL of 10 mM Compound EH in methanol=0.2 mL plasma with 500 microM Compound EH.

Step 2. Samples from step 1 were vortexed for 10 sec at top speed.

Step 3. 0.4 mL of acetonitrile was added to all samples from Step 2, and all vials were vortexed at top speed for 1 min.

Step 4. All samples from step 3 were spun down 14000 rpm, 17000 g, at 4° C., for 25 min.

Step 5. Supernatants were filtered through 0.45 micron, 4 mm, PTFE membrane syringe filter (Phenomenex #AF0-3102-52), 15 microL were injected and resolved on Luna 3 micron, 100 A pore, C8(2), 150×3 mm, reverse phase column (Phenomenex#00F-4248-YO, SN#259151-7) in 50 min linear gradient from 40% to 69% of (0.1% Formic Acid, 89.9% Acetonitrile, 10% Methanol) at 0.25 ml/min, 107 bar, 37° C. column temp, method 406975M1, Agilent 1100 LC-MS.

All samples were run in duplicate, 210 nm and 230 nm Absorbances, Negative and Positive ionization spectrograms recorded.

HPLC Conditions:

TABLE 7

| HLPC gradient | | |
|---|---|---|
| time min | solvent C % | solvent D % |
| 0 | 60 | 40 |
| 2 | 60 | 40 |
| 52 | 31 | 69 |
| 58 | 31 | 69 |
| 60 | 60 | 40 |
| 75 | 60 | 40 |

Figure 4:
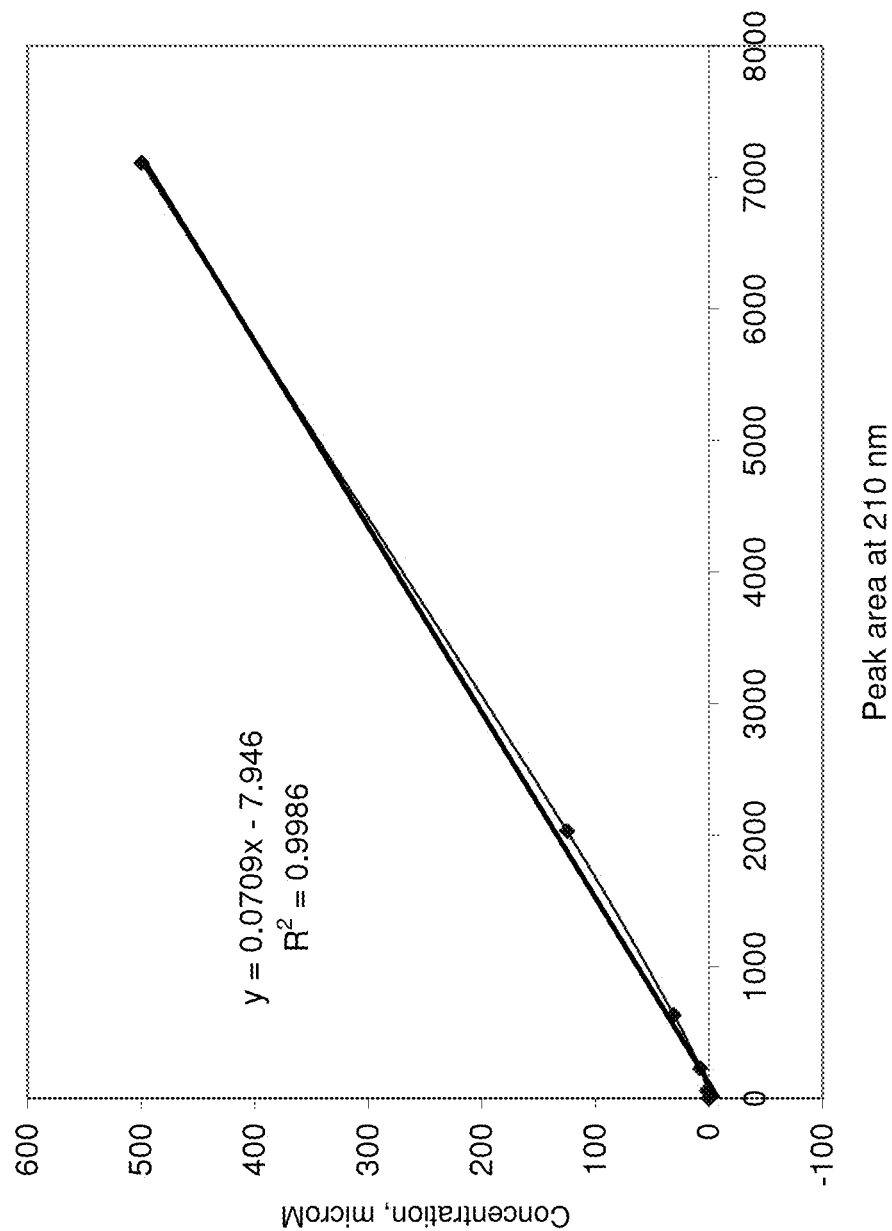
FIG. 4: Compound EH Calibration curve, AGILENT LC-MS.

Solvent C: 0.1% Formic Acid in water
Solvent D: 0.1% Formic Acid, 89.9% Acetonitrile, 10% Methanol Results:

1. Calibration curve (FIG. 4) was built with $R^2$ fit to linearity=0.9986.

TABLE 8

| AGILENT LC-MS | | | |
|---|---|---|---|
| Compound EH Peak area at 210 nm | | | Compound EH in plasma Concentr. |
| run 1 | run 2 | Mean | MicroM |
| 7030 | 7193 | 7111.5 | 500 |
| 2022 | 2039 | 2030.5 | 125 |
| 583.9 | 686.4 | 635.15 | 31.25 |
| 249.6 | 205.9 | 227.75 | 7.8125 |
| 67.12 | 51.43 | 59.275 | 1.9531 |
| 0 | 0 | 0 | 0 |

Figure 5:
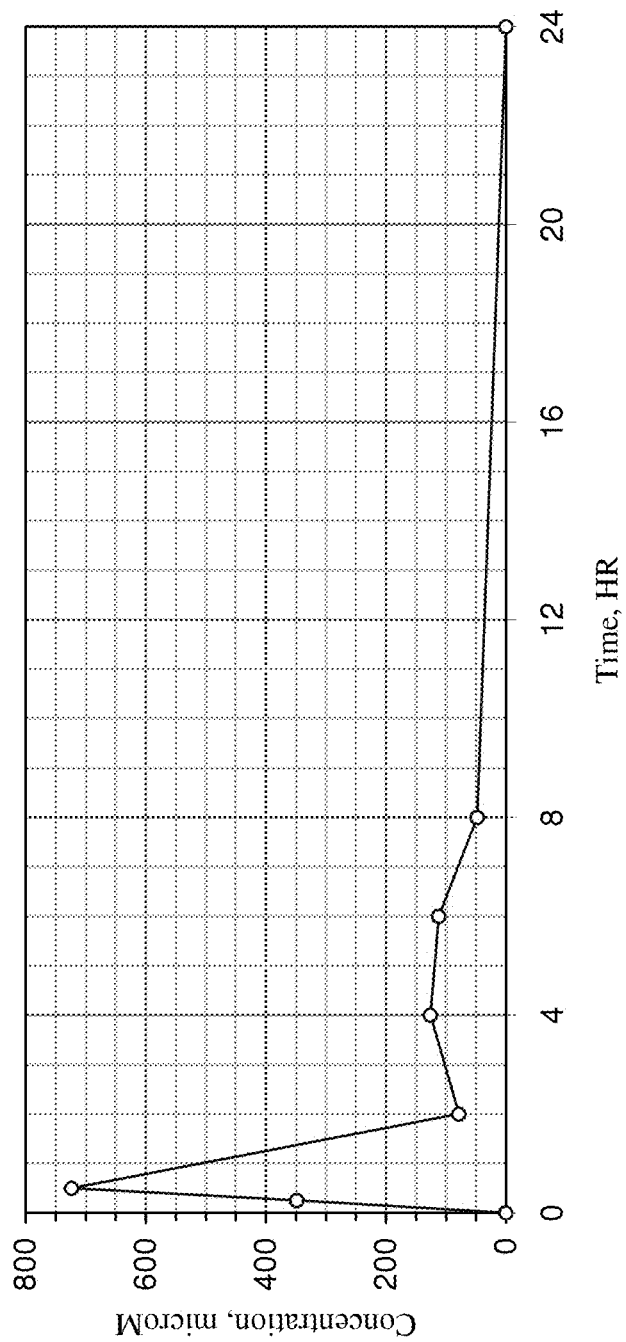
FIG. 5: Compound EH concentration in rat plasma.

2. Compound EH was readily detected in rat plasma, Retention times and mass confirmed in both Positive and Negative ionization modes. (FIG. 5). "M−"=283.2, 100%; 567.2, 73%.

"M+"=302.4 (+H2O) 95%; 214.4 100%; 307.2 75%; 179.2 70%. Formula weight 284.

TABLE 9

| Time (HR) | Compound EH (μM) |
|---|---|
| 0 | 0 |
| 0.25 | 349 |
| 0.5 | 723 |
| 2 | 79 |
| 4 | 126 |
| 6 | 112 |
| 8 | 48 |
| 24 | 0 |
| AUC(0-24): | 1765 microM * HR |
| Cmax: | 723 microM |

Example 28

Mouse Oral Single-Dose Pharmacokinetic Study with Compound EH

Protocol:

A. Plasma.

1. Mice received single oral gavage of Compound EH, 100 mg/kg, and plasma was collected at certain times.
2. Plasma was stored at −80° C. until the day of analysis.
3. Samples were thawed on 37° C. bath for 5 min and vortexed at top speed for 10 sec.
4. Mouse plasma, 0.1 mL was mixed with 0.2 mL Acetonitrile, vortexed 1 min, spun down 14000 rpm, 17000 g, at 4° C., for 25 min.
5. Supernatants were filtered through 0.45 micron, 4 mm, PTFE membrane syringe filter (Phenomenex #AF0-3102-52), and 15 microL were injected and resolved on Luna 3 micron, 100 A pore, C8(2), 150×3 mm, reverse phase column (Phenomenex#00E-4248-YO, SN#259151-7) in 50 min linear gradient from 40% to 69% of (0.1% Formic Acid, 89.9% Acetonitrile, 10% Methanol) at 0.25 mL/min, 100 bar, 37° C. column temperature, method 406975M1, Sequence 0205-09A, Agilent 1100 LC-MS.

All samples were run in duplicate, 210 nm and 230 nm Absorbances, Negative and Positive ionization spectrograms recorded.

B. Calibration Curve.

Step 1. Plasma from "Vehicle" animals (pooled), 0.19 mL, was mixed with 0.01 mL 20× stock of Compound EH in Methanol to make 500 microM, 250 microM, 125 microM, . . . , concentrations of Compound EH in plasma.

For example: 190 microL plasma+10 microL of 10 mM Compound EH in methanol=0.2 mL plasma with 500 microM Compound EH.

Step 2. Samples from step 1 were vortexed for 10 sec at top speed.

Step 3. 0.4 mL of acetonitrile was added to all samples from Step 2, and all vials were vortexed at top speed for 1 min Step 4. All samples from step 3 were spun down 14000 rpm, 17000 g, at 4° C., for 25 min.

Step 5. Supernatants were filtered through 0.45 micron, 4 mm, PTFE membrane syringe filter (Phenomenex #AF0-3102-52), 15 microL were injected and resolved on Luna 3 micron, 100 A pore, C8(2), 150×3 mm, reverse phase column (Phenomenex#00E-4248-YO, SN#259151-7) in 50 min linear gradient from 40% to 69% of (0.1% Formic Acid, 89.9% Acetonitrile, 10% Methanol) at 0.25 ml/min, 100 bar, 37° C. column temp, method 406975M1, Agilent 1100 LC-MS.

All samples were run in duplicate, 210 nm and 230 nm Absorbances, Negative and Positive ionization spectrograms recorded.

HPLC Conditions:

TABLE 10

HLPC gradient

| time min | solvent C % | solvent D % |
|---|---|---|
| 0 | 60 | 40 |
| 2 | 60 | 40 |
| 52 | 31 | 69 |
| 58 | 31 | 69 |
| 60 | 60 | 40 |
| 75 | 60 | 40 |

Figure 6:
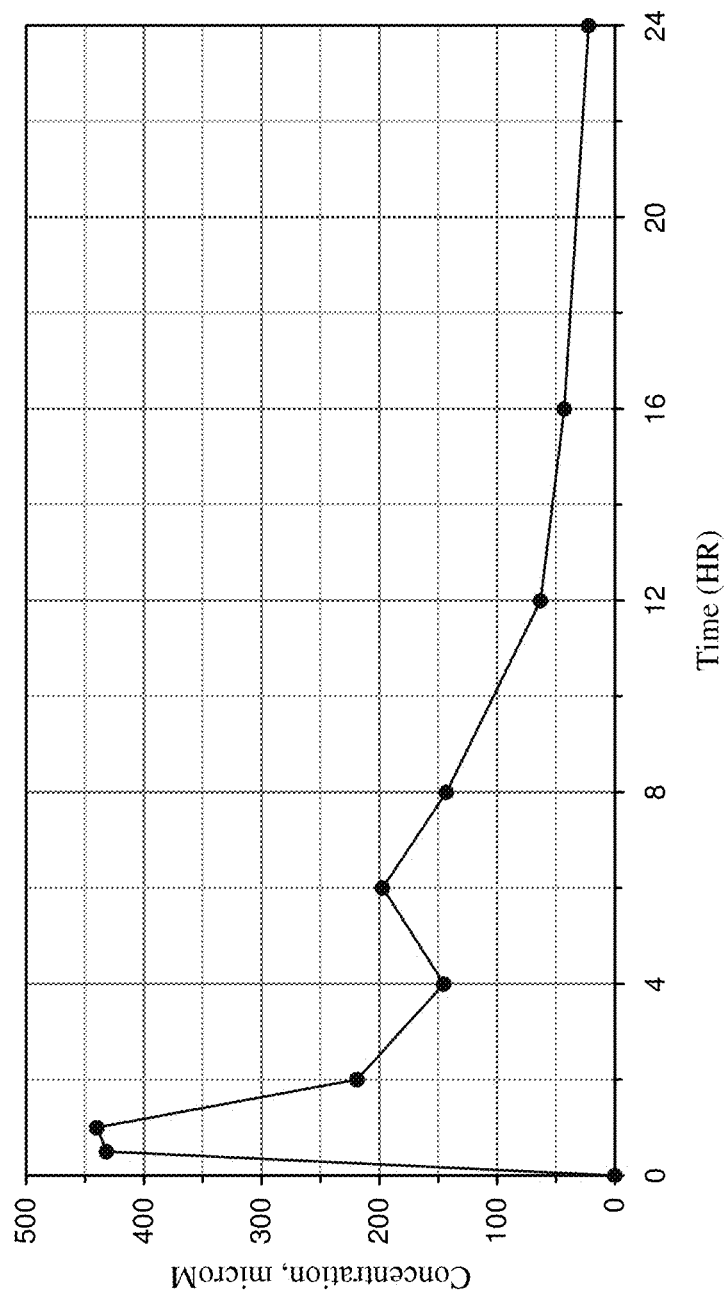
FIG. 6: Compound EH concentration in mouse plasma

Solvent C: 0.1% Formic Acid in water
Solvent D: 0.1% Formic Acid, 89.9% Acetonitrile, 10% Methanol Results:

1. Compound EH was readily detected in mouse plasma, Retention times and mass confirmed in Positive and Negative ionization modes. AGILENT LC-MS sequence 0205-09A. (FIG. 6).

"M−"=283.2 100%, 567.2 47%.

"M+"=214.0 100%, 179.2 97%, 214.4 95%, 302.4 85% (Compound H+H2O=302) Formula weight 284, Retention Time average=35 min.

TABLE 11

| Mouse plasma # | Bleed time | Compound EH Concentration in mouse PLASMA, microM |
|---|---|---|
| 6 | 0.5 HR | 430 |
| 7 | 0.5 HR | 342 |
| 8 | 0.5 HR | 523 |
| 9 1 hr | 1 HR | 447 |
| 10 1 hr | 1 HR | 406 |
| 11 1 hr | 1 HR | 467 |
| 12 2 hr | 2 HR | 178 |
| 13 2 hr | 2 HR | 238 |
| 14 2 hr | 2 HR | 241 |
| 15 | 4 HR | 148 |
| 16 | 4 HR | 154 |
| 17 | 4 HR | 134 |
| 24 | 6 HR | 93 |
| 25 | 6 HR | 268 |
| 26 | 6 HR | 231 |
| 27 | 8 HR | 95 |
| 28 | 8 HR | 147 |
| 29 | 8 HR | 187 |
| 18 | 12 HR | 79 |
| 19 | 12 HR | 36 |
| 20 | 12 HR | 74 |
| 22 | 16 HR | 25 |
| 23 | 16 HR | 61 |
| 30 | 24 HR | 40 |
| 31 | 24 HR | 26 |
| 32 | 24 HR | 0.74 |
| 33 | 48 HR | 0 |
| 34 | 48 HR | 0 |
| 35 | 48 HR | 0 |

TABLE 12

Data from Sigma Stat

| Time bleed HR | Compound EH concentr., microM mean | Std. Error |
|---|---|---|
| 0 | 0 | 0 |
| 0.5 | 431.7 | 52 |
| 1 | 440 | 18 |
| 2 | 219 | 20.5 |
| 4 | 145.3 | 5.9 |
| 6 | 197.3 | 53 |
| 8 | 143 | 27 |
| 12 | 63 | 13.58 |
| 16 | 43 | 18 |
| 24 | 22.247 | 11.5 |
| 48 | 0 | 0 |

TABLE 13

| Time (HR) | Cpd. EH (µM) |
|---|---|
| 0 | 0 |
| 0.5 | 432 |
| 1 | 440 |
| 2 | 219 |
| 4 | 145 |
| 6 | 197 |
| 8 | 143 |
| 12 | 63 |
| 16 | 43 |
| 24 | 22 |
| 48 | 0 |
| t½: | 8.05 |
| AUC$_{0-24}$: | 2588 |

Cmax = 440 microM
t½ = 8.05 HR
AUC = 2588 microM * HR

What is claimed is:

1. A method of reducing the uric acid concentration in blood of, or increasing uric acid excretion from, a mammalian subject in need thereof, comprising administering to the subject a compound of Formula IA or a pharmaceutically acceptable salt thereof

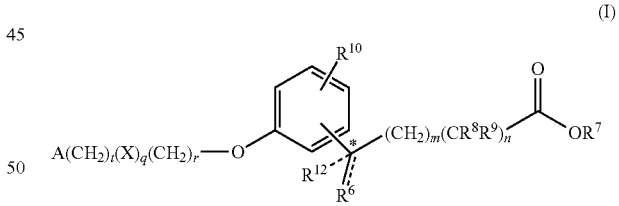

wherein:
m is 0, 1, 2, 3 or 4;
n is 0 or 1;
m+n is not more than 4;
t is 0;
q is 0 or 1;
r is 0 or 1;
$R^6$ is hydrogen, methyl or ethyl and $R^{12}$ is hydrogen or methyl, or $R^6$ is hydroxy and $R^{12}$ is hydrogen, or $R^6$ is O and $R^{12}$ is absent, or $R^6$ and $R^{12}$ together are —CH$_2$CH$_2$—;
$R^7$ is hydrogen or alkyl having from 1 to 3 carbon atoms;
one of $R^8$ and $R^9$ is alkyl having from 1 to 3 carbon atoms, and the other is hydrogen or alkyl having from 1 to 3 carbon atoms;

$R^{10}$ is hydrogen, halo, alkyl having from 1 to 3 carbon atoms or alkoxy having from 1 to 3 carbon atoms;

when q is 1, X is C(O) and r is 0;

A is phenyl, unsubstituted or substituted by 1 or 2 groups selected from halo, hydroxy, methyl, ethyl, perfluoromethyl, methoxy, ethoxy, and perfluoromethoxy.

2. The method of claim 1, wherein the Compound is represented by Formula IA1

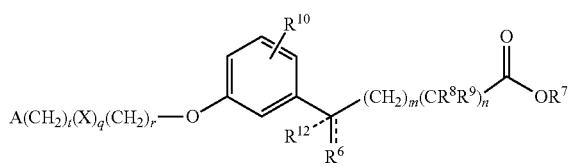

(IA)

wherein
two of $R^1$, $R^2$, $R^3$, $R^4$ and $R^5$ are selected from the group consisting of hydrogen, halo, hydroxy, methyl, ethyl, perfluoromethyl, methoxy, ethoxy and perfluoromethoxy, and the remainder are hydrogen;

m is 0, 1, 2, 3 or 4;
n is 0 or 1;
m+n is not more than 4;
$R^6$ is hydrogen, methyl or ethyl and $R^{12}$ is hydrogen or methyl, or $R^6$ is hydroxy and $R^{12}$ is hydrogen, or $R^6$ is O and $R^{12}$ is absent, or $R^6$ and $R^{12}$ together are —CH$_2$CH$_2$—;
$R^7$ is hydrogen or alkyl having from 1 to 3 carbon atoms;
one of $R^8$ and $R^9$ is alkyl having from 1 to 3 carbon atoms, and the other is hydrogen or alkyl having from 1 to 3 carbon atoms;
$R^{10}$ is hydrogen, halo, alkyl having from 1 to 3 carbon atoms or alkoxy having from 1 to 3 carbon atoms.

3. The method of claim 2, wherein $R^1$ is methyl and $R^5$ is methyl.

4. The method of claim 3, wherein the Compound is selected from the group consisting of:
4-(3-(2,6-Dimethylbenzyloxy)phenyl)-4-oxobutyric acid;
3-(2,6-Dimethylbenzyloxy)-phenylacetic acid; and
4-3-(2,6-Dimethylbenzyloxy)-phenyl)-4-hydroxybutanoic acid.

5. The method of claim 1, wherein the Compound is selected from the group consisting of:
2-(3-(2,6-Dimethylbenzyloxy)-4-methoxyphenyl)acetic acid;
4-(3-(2-Methylbenzyloxyl)phenyl)-4-oxobutanoic acid;
4-(3-(2,6-Difluorobenzyloxyl)phenyl)-4-oxobutanoic acid;
4-(3-(2-Fluoro-6-methylbenzyloxy)phenyl)-4-oxobutanoic acid;
4-(3-(2,6-Dimethylbenzyloxyl)phenyl)-2,2-dimethyl-4-oxobutanoic acid;
4-(3-(2,6-Dimethylbenzyloxyl)phenyl)butanoic acid;
Methyl 3-(3-(2,6-dimethylbenzyloxyl)phenyl)-3-oxopropanoate;

5-(3-(2,6-Dimethylbenzyloxyl)phenyl)-5-oxopentanoic acid;
2-(3-(2,6-Dimethylbenzyloxyl)phenyl)-2-oxoacetic acid;
5-(3-(2,6-Dimethylbenzyloxyl)phenyl)pentanoic acid;
3-(3-(2,6-Dimethylbenzyloxyl)phenyl)propanoic acid;
2-(3-(2,6-Difluorobenzyloxyl)phenyl)acetic acid;
4-(3-(2,6-Dichlorobenzyloxyl)phenyl)-4-oxobutanoic acid;
2-(3-(2,6-Dimethylbenzyloxyl)phenyl)propanoic acid;
2-(3-(4-Trifluoromethyl)benzyloxy)phenyl)acetic acid;
2-(3-(2,4-bis(trifluoromethyl)benzyloxy)phenyl)acetic acid;
2-(3-(2,6-Dimethylbenzyloxyl)phenyl)butanoic acid;
2-(3-(3,5-Dimethylbenzyloxyl)phenyl)acetic acid;
2-(3-(2,4-Dimethylbenzyloxyl)phenyl)acetic acid;
2-(3-(2,6-Dimethoxylbenzyloxyl)phenyl)acetic acid;
2-(3-(Benzyloxy)phenyl)acetic acid;
2-(3-(2,6-Dimethylbenzyloxyl)phenyl)propanoic acid;
2-(3-(2,6-Dimethylbenzyloxyl)phenyl)butanoic acid;
2-(3-(2,6-Dimethylbenzyloxyl)phenyl)-2-methylpropanoic acid;
1-(3-(2,6-Dimethylbenzyloxyl)phenyl)cyclopropanecarboxylic acid; and
2-(3-(2,6-Dimethylbenzyloxy)-4-fluorophenyl)acetic acid.

6. The method of claim 1, wherein the Compound is selected from the group consisting of:
4-(3-(2,6-Dimethylbenzoyloxyl)phenyl)-4-oxobutanoic acid; and
2-(3-(2-Chloro-6-methylbenzyloxy)phenyl)acetic acid.

7. The method of claim 1 wherein the subject has a condition selected from the group consisting of gout, hyperuricemia, elevated levels of uric acid that do not meet the levels customarily justifying a diagnosis of hyperuricemia, and tumor-lysis syndrome.

8. The method of claim 1, wherein the subject is a human.

9. The method of claim 1, further comprising administering to the subject one or more other uric acid lowering drugs in a combined amount effective to reduce the uric acid concentration in blood of, or increase uric acid excretion from, the subject.

10. The method of claim 9, wherein the other uric acid lowering drug is selected from the group consisting of a xanthine oxidase inhibitor, a uricosuric agent, a urate transporter-1 inhibitor, a uricase, and a statin.

11. The method of claim 9, wherein the other uric acid lowering drug is administered in an amount that is less than the usual therapeutic dose when administered alone.

12. The method of claim 9, wherein the Compound of Formula IA or salt thereof and the one or more other uric acid lowering drugs are mixed together to form an admixture and the admixture is administered to the subject.

13. The method of claim 9, wherein the Compound of Formula IA or salt thereof and the one or more other uric acid lowering drugs are not mixed together to form an admixture but are administered independently to the subject.

14. The method of claim 1, wherein the Compound of Formula IA or salt thereof is formulated for oral administration.

* * * * *